US011473150B2

(12) United States Patent
Sia et al.

(10) Patent No.: US 11,473,150 B2
(45) Date of Patent: Oct. 18, 2022

(54) METHODS FOR THE DETECTION AND TREATMENT OF CLASSES OF HEPATOCELLULAR CARCINOMA RESPONSIVE TO IMMUNOTHERAPY

(71) Applicant: Icahn School of Medicine at Mount Sinai, New York, NY (US)

(72) Inventors: Daniela Sia, New York, NY (US); Josep Maria Llovet I Bayer, New York, NY (US); Augusto Villanueva-Rodriguez, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 197 days.

(21) Appl. No.: 16/621,983

(22) PCT Filed: Jun. 14, 2018

(86) PCT No.: PCT/US2018/037579
§ 371 (c)(1),
(2) Date: Dec. 12, 2019

(87) PCT Pub. No.: WO2018/232142
PCT Pub. Date: Dec. 20, 2018

(65) Prior Publication Data
US 2021/0277480 A1    Sep. 9, 2021

Related U.S. Application Data

(60) Provisional application No. 62/629,231, filed on Feb. 12, 2018, provisional application No. 62/519,711, filed on Jun. 14, 2017.

(51) Int. Cl.
*C12Q 1/6886* (2018.01)
*C07K 16/28* (2006.01)

(52) U.S. Cl.
CPC ........ *C12Q 1/6886* (2013.01); *C07K 16/2818* (2013.01); *C07K 16/2827* (2013.01); *C12Q 2600/106* (2013.01); *C12Q 2600/158* (2013.01)

(58) Field of Classification Search
CPC .................................................. C12Q 1/6886
USPC ...................................................... 424/143.1
See application file for complete search history.

(56) References Cited

U.S. PATENT DOCUMENTS

| 2008/0139801 A1 | 6/2008 | Umansky, Sr. et al. |
| 2015/0203919 A1 | 7/2015 | Inserm et al. |
| 2017/0080070 A1 | 3/2017 | Weinschenk et al. |

FOREIGN PATENT DOCUMENTS

| WO | WO 2009/055480 | 4/2009 |
| WO | WO 2009/152300 | 12/2009 |
| WO | WO 2012/096631 | 7/2012 |
| WO | WO 2016/0109546 | 7/2016 |

OTHER PUBLICATIONS

Roessler et al (Cancer Res, 2010, 70(24): 10202-10212).*
Longo et al (Oncotarget, 2017, 8(20): 33897-33901).*
Elia Moreno-Cubero et al: "Specific CD8 + T cell response immunotherapy for hepatocellular carcinoma and viral hepatitis", World Journal of Gastroenterology, vol. 22, No. 28, Jan. 1, 2016 (Jan. 1, 2016), p. 6469, XP055561848, CN ISSN: 1007-9327, DOI: 10.3748/wjg.v22.i28.6469 * the whole document *.
Sacha Gnjatic et al.: "Identifying baseline immune-related biomarkers to predict clinical outcome of immunotherapy", Journal for Immunotherapy of Cancer, Biomed Central Ltd, London, UK, vol. 5, No. I, May 16, 2017 (May 16, 2017), pp. 1-18, XP021245142, DOI: 10.1186/540425-017-0243-4 * the whole document *.
Alistar, et al., "Dual roles for immune metagenes in breast cancer prognosis and therapy prediction", (Jun. 6, 2014) Genome Med 6:80.
Bald, et al., "Immune Cell-Poor Melanomas Benefit from PD-1 Blockade after Targeted Type I IFN Activation", (Mar. 3, 2014) Cancer Discov 4:674-87.
Balli, et al., "Immune Cytolytic Activity Stratifies Molecular Subsets of Human Pancreatic Cancer", (Dec. 22, 2016) Clin Cancer Res 23(12):3129-38.
Bindea, et al., "Spatiotemporal Dynamics of Intratumoral Immune Cells Reveal the Immune Landscape in Human Cancer", (Oct. 17, 2013) Immunity 39:782-95.
Borghaei, et al., "Nivolumab versus Docetaxel in Advanced Nonsquamous Non-Small-Cell Lung Cancer", (Oct. 22, 2015) N Engl J Med 373:1627-39.
Boyault, et al., "Transcriptome Classification of HCC Is Related to Gene Alterations and to New Therapeutic Targets", (2007) Hepatology 45:42-52. Received Jul. 13, 2006.
Brunnstrom et al., "PD-L1 immunohistochemistry in clinical diagnostics of lung cancer: inter-pathologist variability is higher than assay variability", (Jun. 30, 2017) Modern Pathology 30(10):1411-21.
Breiman, "Random Forests", (2001) Machine Learning, 45(1):5-32. Received Nov. 30, 1999.
Brunet, et al., "Metagenes and molecular pattern discovery using matrix factorization", (2004) Proc Natl Acad Sci U S A 101:4164-9. Received Nov. 1, 2003.
Calderaro, et al. "Programmed Death Ligand 1 Expression in Hepatocellular Carcinoma: Relationship With Clinical and Pathological Features", (Mar. 14, 2016) Hepatology 64:2038-2046.
Calon, et al., "Dependency of colorectal cancer on a TGF-beta-driven programme in stromal cells for metastasis initiation". (Nov. 13, 2012) Cancer Cell 22:571-84.
Cancer Genome Atlas N. Genomic Classification of Cutaneous Melanoma. (Jun. 18, 2015) Cell 161:1681-96.

(Continued)

*Primary Examiner* — Sean E Aeder
(74) *Attorney, Agent, or Firm* — Leason Ellis LLP

(57) ABSTRACT

The present invention relates to methods for detecting, diagnosing, prognosing, monitoring, and treating a patient with hepatocellular carcinoma. In particular, the invention provides diagnostic markers for the detection and treatment of patients who would benefit from immunotherapy, i.e., patient who would be most responsive to immunotherapy.

12 Claims, 42 Drawing Sheets

(56) References Cited

OTHER PUBLICATIONS

Charoentong, et al., "Pan-cancer Immunogenomic Analyses Reveal Genotype-Immunophenotype Relationships and Predictors of Response to Checkpoint Blockade", (Jan. 3, 2017) Cell Rep 18:248-262.
Chen, et al., "Analysis of immune signatures in longitudinal tumor samples yields insight into biomarkers of response and mechanisms of resistance to immune checkpoint blockade", (Aug. 2016) Cancer Discov 6:827-37.
Chen, et al., "Gene Expression Patterns in Human Liver Cancers", (Jun. 2002) Mol Biol Cell 13:1929-39.
Chiang, et al., "Focal Gains of Vascular Endothelial Growth Factor A and Molecular Classification of Hepatocellular Carcinoma", (Aug. 15, 2008) Cancer Res 68:6779-88.
Chow, et al., "Biomarkers and Response to Pembrolizumabin Recurrent/Metastatic Head and NeckSquamous Cell Carcinoma (R/M HNSCC)", (May 2016) J Clin Oncol 34, (suppl; abstr 6010).
Coates, et al., "Indirect Macrophage Responses to Ionizing Radiation: Implications for Genotype-Dependent Bystander Signaling", (Jan. 15, 2008) Cancer Res 68:450-6.
Coulouar, et al., "Transforming Growth Factor-β Gene Expression Signature in Mouse Hepatocytes Predicts Clinical Outcome in Human Cancer", (Jun. 2008) Hepatology 47:2059-67.
Davoli, et al., "Tumor aneuploidy correlates with markers of immune evasion and with reduced response to immunotherapy", (Jan. 20, 2017) Science 355(6322).
Deng, et al., "Irradiation and anti-PD-L1 treatment synergistically promote antitumor immunity in mice", (Feb. 2014) J. Clin. Invest. 124(2):687-695.
Finkin, et al., "Ectopic lymphoid structures function as microniches for tumor progenitor cells in hepatocellular carcinoma", (Dec. 2015) Nat Immunol 16:1235-44.
Flavell, et al., "The polarization of immune cells in the tumour environment by TGFβ", (Aug. 2010) Nat Rev Immunol 10:554-67.
Garon, et al., "Pembrolizumab for the Treatment of Non-Small-Cell Lung Cancer", (Apr. 19, 2015) N Engl J Med 372:2018-28.
Hanahan and Weinberg, "Hallmarks of Cancer: The Next Generation", (March 4, 2011) Cell 144:646-74.
Hoshida, et al., "Integrative Transcriptome Analysis Reveals Common Molecular Subclasses of Human Hepatocellular Carcinoma", (Sep. 15, 2009) Cancer Res 69:7385-92.
Hoshida, et al., "Gene Expression in Fixed Tissues and Outcome in Hepatocellular Carcinoma", (Nov. 6, 2008) N Engl J Med 359:1995-2004.
Hoshida, et al., "Subclass Mapping: Identifying Common Subtypes in Independent Disease Data Sets", (Nov. 2007) PLoS One 2:e1195.
Hoshida, et al., "Prognostic Gene-Expression Signature for Patients with Hepatitis C-Related Early-Stage Cirrhosis", (May 2013) Gastroenterology 144(5):1024-30.
Jiang, et al., "Targeting Focal Adhesion Kinase Renders Pancreatic Cancers Responsive to Checkpoint Immunotherapy", (Aug. 2016) Nat Med 22:851-60.
Khalil, et al., "The future of cancer treatment: immunomodulation, CARs and combination immunotherapy", (May 2016) Nat Rev Clin Oncol 13:394.
Lachenmayer, et al., "Wnt-pathway activation in two molecular classes of hepatocellular carcinoma and experimental modulation by sorafenib", (Sep. 15, 2012) Clin Cancer Res 18:4997-5007.
Le, et al., "PD-1 Blockade in Tumors with Mismatch-Repair Deficiency", (May 30, 2015) N Engl J Med 372:2509-20.
Llovet, et al., "Sorafenib in Advanced Hepatocellular Carcinoma", (Jul. 24, 2008) N Engl J Med 359:378-90.
McGranahan, et al., "Clonal neoantigens elicit T cell immunoreactivity and sensitivity to immune checkpoint blockade", (Mar. 25, 2016) Science 351:1463-9.
Mermel, et al., "GISTIC2.0 facilitates sensitive and confident localization of the targets of focal somatic copy-number alteration in human cancers", (2011) Genome Biol 12:R41. Received Aug. 18, 2010.

Messina, et al., "12-Chemokine Gene Signature Identifies Lymph Node-like Structures in Melanoma: Potential for Patient Selection for Immunotherapy?", (Jun. 19, 2012) Sci Rep 2:765.
Moffitt, et al., "Virtual microdissection identifies distinct tumor- and stroma-specific subtypes of pancreatic ductal adenocarcinoma", (Oct. 2015) Nat Genet 47:1168-78.
Nielsen, et al., "NetMHCpan, a Method for Quantitative Predictions of Peptide Binding to Any HLA-A and -B Locus Protein of Known Sequence", (Aug. 2007) PLoS One 2:e796.
Park, et al., "TGFβ1-Mediated SMAD3 Enhances PD-1 Expression on Antigen-Specific T Cells in Cancer", (Sep. 28, 2016) Cancer Discov 6:1366-81.
Peng, et al., "Loss of PTEN promotes resistance to T cell-mediated Immunotherapy", (Feb. 2016) Cancer Discov 6:202-16.
Porta-Pardo and Godzik, "Mutation Drivers of Immunological Responses to Cancer", (Jul. 11, 2016) Cancer Immunol Res 4:789-98.
Rajasagi, et al., "Systematic identification of personal tumor-specific neoantigens in chronic lymphocytic leukemia", (Jul. 17, 2014) Blood 124:453-62.
Robert, et al., "Pembrolizumab versus Ipilimumab in Advanced Melanoma", (Apr. 19, 2015) N Engl J Med 372:2521-32.
Roh, et al., "Integrated molecular analysis of tumor biopsies on sequential CTLA-4 and PD-1 blockade reveals markers of response and resistance", (Mar. 1, 2017) Sci Transl Med 9.
Rooney, et al., "Molecular and Genetic Properties of Tumors Associated with Local Immune Cytolytic Activity", (Jan. 15, 2015) Cell 60:48-61.
Schulze, et al., "Exome sequencing of hepatocellular carcinomas identifies new mutational signatures and potential therapeutic targets", (May 2015) Nat Genet 47:505-11.
Slavuljica, et al., "Manipulation of NKG2D ligands by cytomegaloviruses: impact on innate and adaptive immune response", (Dec. 28, 2011) Front Immunol 2:85.
Stephen, et al., "Transforming Growth Factor b-Mediated Suppression of Antitumor T Cells Requires FoxP1 Transcription Factor Expression", (Sep. 18, 2014) Immunity 41:427-39.
Topalian, et al., "Safety, Activity, and Immune Correlates of Anti-PD-1 Antibody in Cancer", (Jun. 28, 2012) N Engl J Med 366:2443-54.
Villanueva, et al., "DNA Methylation-Based Prognosis and Epidrivers in Hepatocellular Carcinoma", (2015) Hepatology 61:1945-56. Received Aug. 6, 2014.
Villanueva, et al., "Combining Clinical, Pathology, and Gene Expression Data to Predict Recurrence of Hepatocellular Carcinoma", (May 2011) Gastroenterology 140:1501-12 e2.
Wang et al., "PD-L1 expression in human cancers and its association with clinical outcomes", (Aug. 12, 2016) OncoTargets and Therapy 9:5023-39.
Yoshihara, et al., "Inferring tumour purity and stromal and immune cell admixture from expression data", (Jul. 12, 2013) Nat Commun 4:2612.
Zou et al., "PD-L1 (B7-H1) and PD-1 Pathway Blockade for Cancer Therapy: Mechanisms, Response Biomarkers and Combinations", (Mar. 2, 2016) Sci Transl. Med 8:328rv4.
El-Khoueiry, et al., "Nivolumab in patients with advanced hepatocellular carcinoma (CheckMate 040): an open-label, non-comparative, phase 1/2 dose escalation and expansion trial", (Apr. 20, 2017) Lancet 389:2492-2502.
Herbst, et al., "Pembrolizumab versus docetaxel for previously treated, PD-L1-positive, advanced non-small-cell lung cancer (KEYNOTE-010): a randomised controlled trial", (2016) Lancet 387:1540-50. Published Online Dec. 19, 2015.
Iizuka, et al., "Oligonucleotide microarray for prediction of early intrahepatic recurrence of hepatocellular carcinoma after curative resection", (Mar. 15, 2003) Lancet 361:923-9.
Lee, et al., "Application of comparative functional genomics to identify best-fit mouse models to study human cancer", (Dec. 2004) Nat Genet 36:1306-11.
Reich, et al., "GenePattern 2.0", (May 2006) Nat Genet 38:500-1.
Spranger, et al., "Melanoma-intrinsic β-catenin signalling prevents anti-tumour immunity", (Jul. 9, 2015) Nature 523:231-5.
Weir, et al., "Characterizing the cancer genome in lung adenocarcinoma", (Dec. 6, 2007) Nature 450:893-8.

(56) References Cited

OTHER PUBLICATIONS

Zucman-Rossi, et al., "Genetic Landscape and Biomarkers of Hepatocellular Carcinoma", (Oct. 2015) Gastroenterology 149:1226-1239 e4.

Gnjatic, S et al., Identifying Baseline Immune-Related Biomarkers to Predict Clinical Outcome of Immunotherapy. Journal for Immunotherapy of Cancer. May 16, 2017; vol. 5, No. 44; pp. 1-18; p. 5, col. 1, paragraph 1; DOI: 10.1186/S40425-017-0243-4.

Cubero, Me et al., Specific COB(+) T cell Response Immunotherapy for Hepatocellular Carcinoma and Viral Hepatitis. World Journal of GastroEnterology. Jul. 28, 2016; vol. 22, No. 28; pp. 6469-6483; p. 6475, col. 2, paragraph 1.

Sia, D et al., Identification of an Immune-specific Class of Hepatocellular Carcinoma, Based on Molecular Features. GastroEnterology. Jun. 15, 2017; vol. 153, No. 3; pp. 812-826; whole document; DOI: 10.1053/j.gastro.2017.06.007.

\* cited by examiner

FIGURE 2

| Signature Name | Study |
|---|---|
| Immune enrichment score | Yoshihara K, et al. Nat Commun 2013;4:2612 |
| Stromal enrichment score | Yoshihara K, et al. Nat Commun 2013;4:2612 |
| T cells | Bindea G, et al. Immunity 2013;39:782-95 |
| Cytotox | Bindea G, et al. Immunity 2013;39:782-95 |
| Macrophages | Bindea G, et al. Immunity 2013;39:782-95 |
| TLS | Finkin S, et al. Nat Immunol 2015;16:1235-44 |
| TLS | Messina JL, et al. Sci Rep 2012;2:765 |
| B.P. Metagene | Alistar A, et al. Genome Med 2014;6:80 |
| T.NK Metagene | Alistar A, et al. Genome Med 2014;6:80 |
| 28-gene IFN signature | Ribas A, et al. J Clin Oncol 33, 2015 (suppl; abstr 3001) |
| 6-gene IFN signature | Chow LQM, et al. J Clin Oncol 34, (suppl; abstr 6010) 2016 |
| PD-1 signaling | Quigley M, et al. Nat Med 2010;16:1147-51 |
| IFN subclass of HCC | Chiang DY, et al. Cancer Res 2008;68:6779-88 |
| S1 subclass of HCC | Hoshida Y, et al. Cancer Res 2009;69:7385-92 |
| CTNNB1 subclass of HCC | Chiang DY, et al. Cancer Res 2008;68:6779-88 |
| S2 subclass of HCC | Hoshida Y, et al. Cancer Res 2009;69:7385-92 |
| Activated stroma | Moffitt RA, et al. Nat Genet 2015;47:1168-78 |
| T cell exhaustion signature | Quigley M, et al. Nat Med 2010;16:1147-51 |
| WNT/TGB signature | Lachenmayer A, et al. Clin Cancer Res 2012;18:4997-5007 |
| M1/M2 macrophages | Coates PJ, et al. Cancer Res 2008;68:450-6 |
| Late TGFB signature | Coulouarn C, et al. Hepatology. 2008 Jun;47(6):2059-67 |
| T cells-TBRS | Calon A, et al. Cancer Cell 2012;22:571-84 |
| Fibroblast-TBRS | Calon A, et al. Cancer Cell 2012;22:571-84 |
| Immune cell subsets | Cancer Genome Atlas N. Cell 2015;161:1681-96 |
| Immune signaling molecules | Cancer Genome Atlas N. Cell 2015;161:1681-96 |
| B cells | Bindea G, et al. Immunity 2013;39:782-95 |
| CD8 T cells | Bindea G, et al. Immunity 2013;39:782-95 |
| Tem cells | Bindea G, et al. Immunity 2013;39:782-95 |
| Th1 cells | Bindea G, et al. Immunity 2013;39:782-95 |
| 186 gene signature | Hoshida Y, et al. N Engl J Med 2008;359:1995-2004 |
| cytolytic activity | Rooney MS, et al. Cell 2015;160:48-61 |

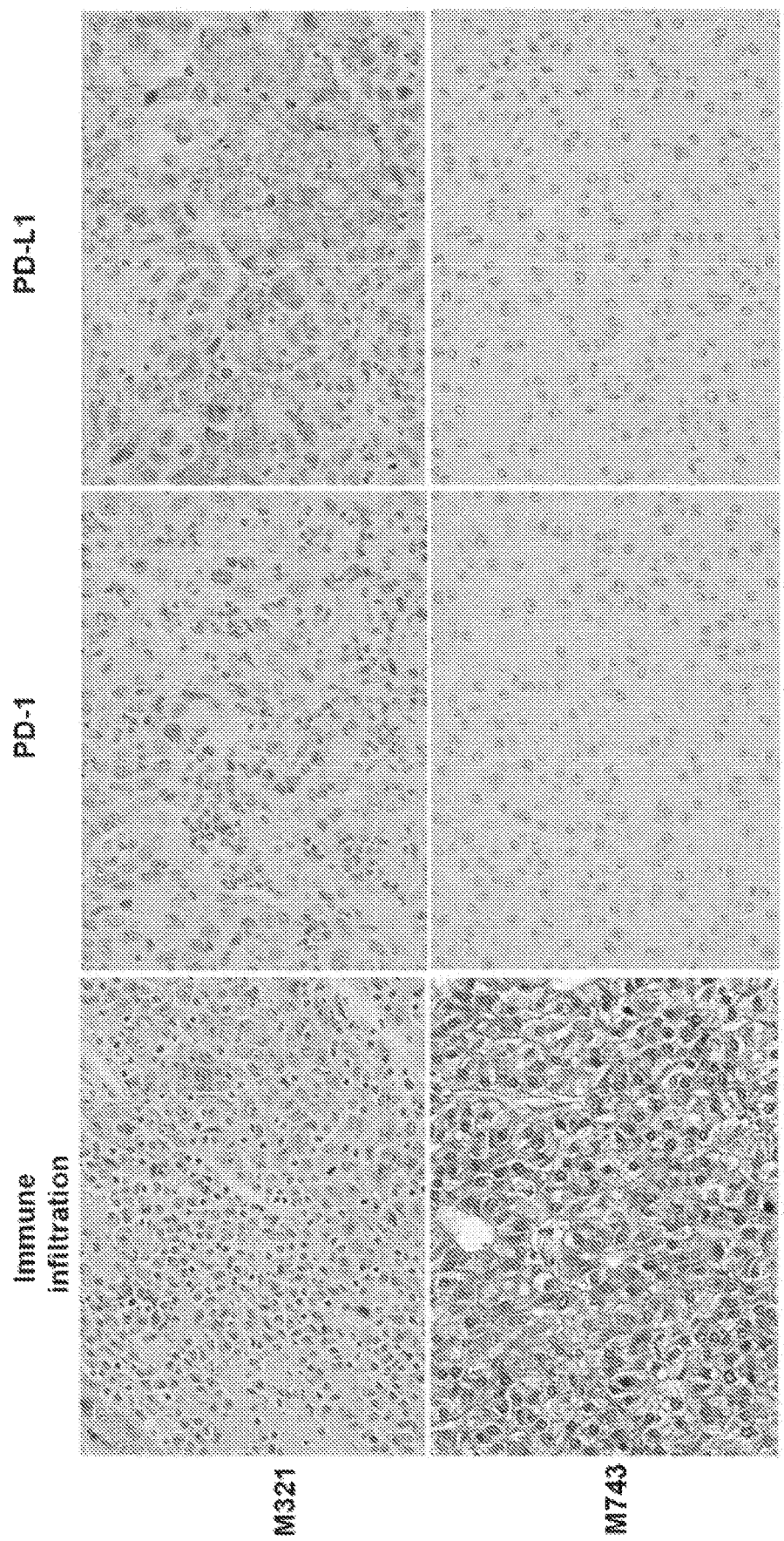

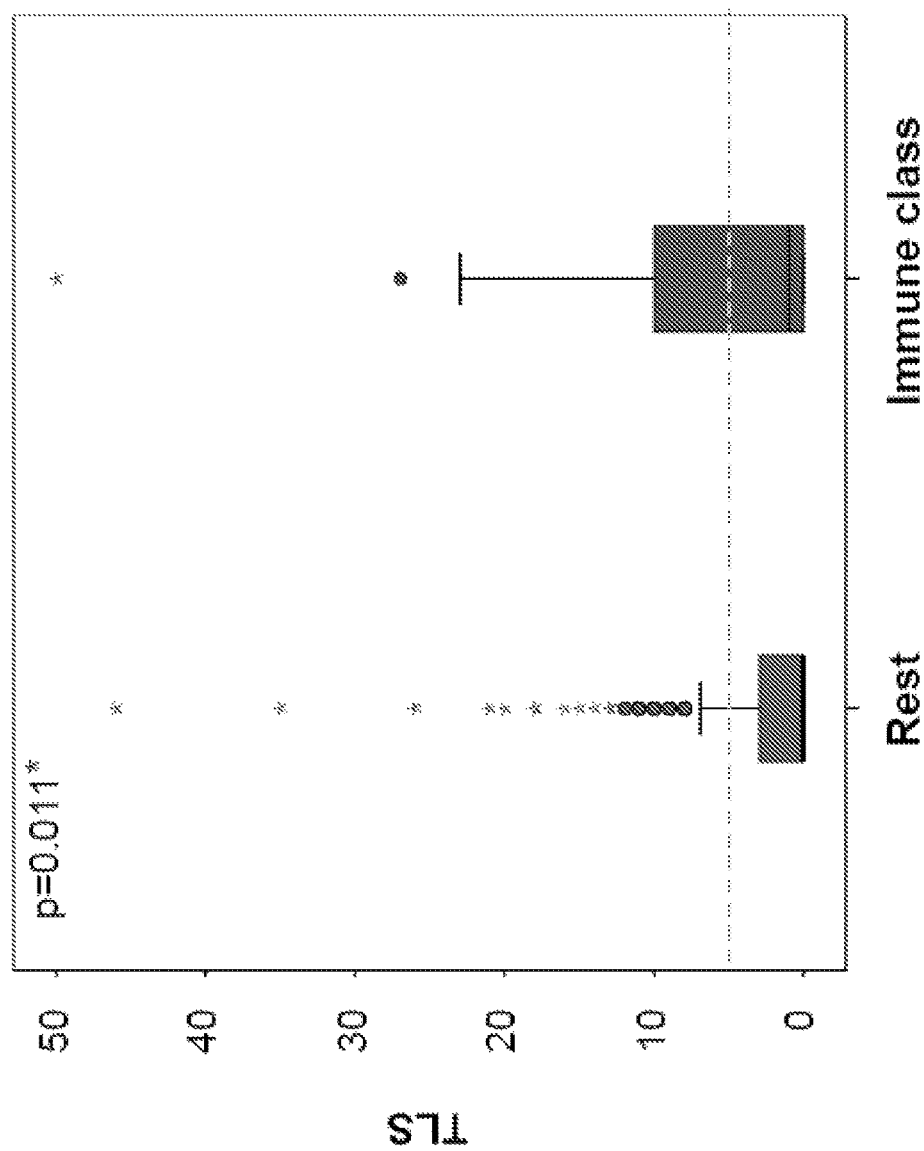

FIGURE 5
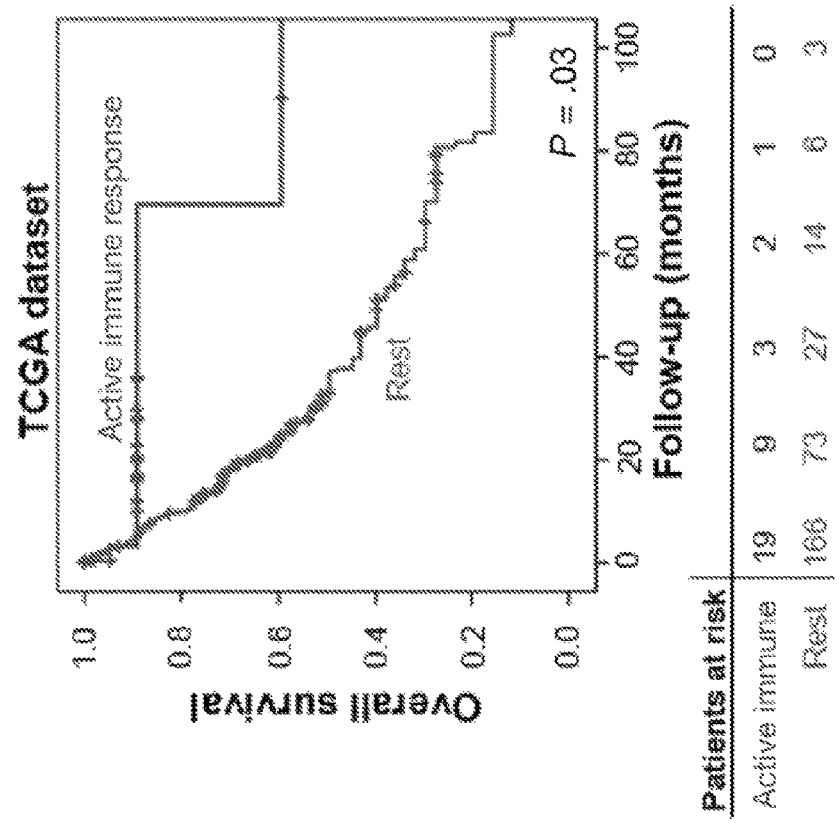
FIGURE 5B
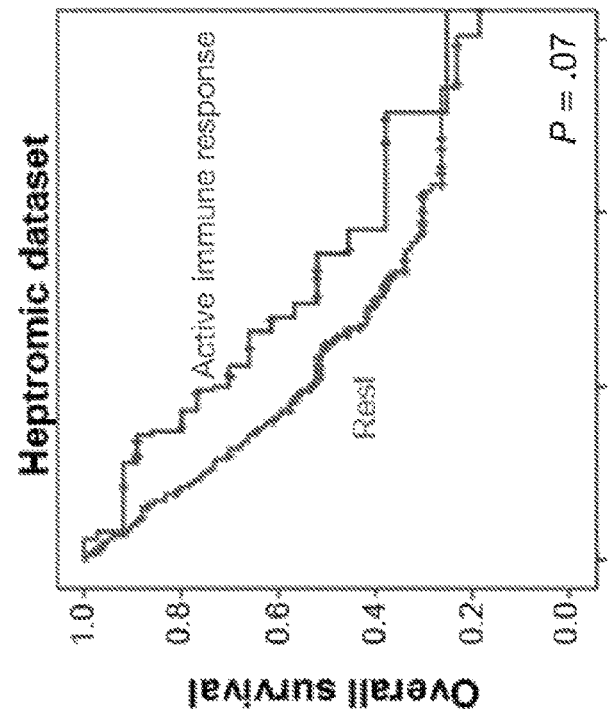
FIGURE 5A

FIGURE 6
FIGURE 6A
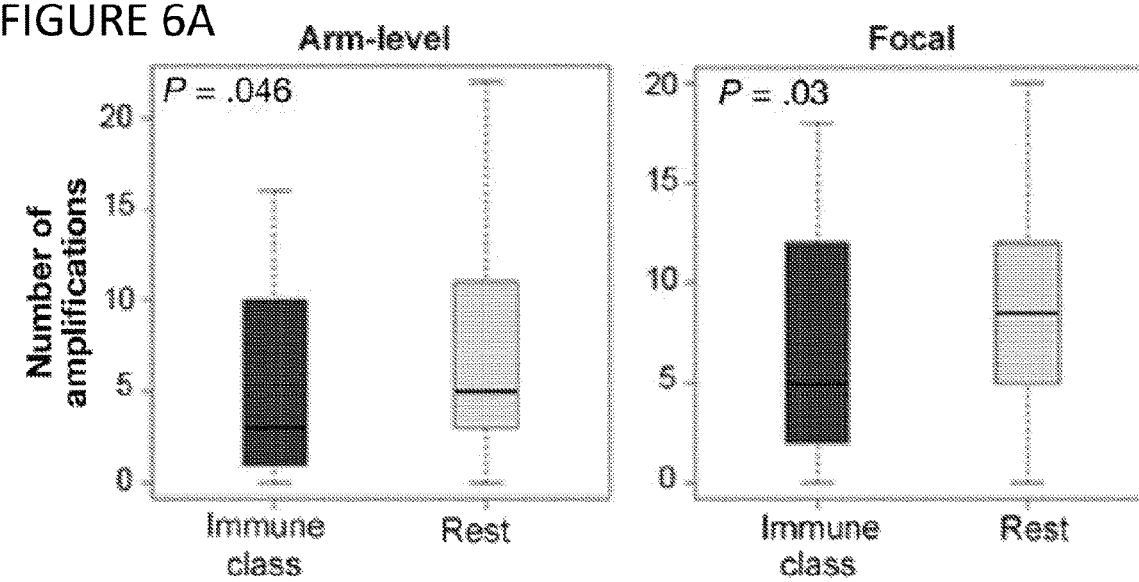
FIGURE 6B
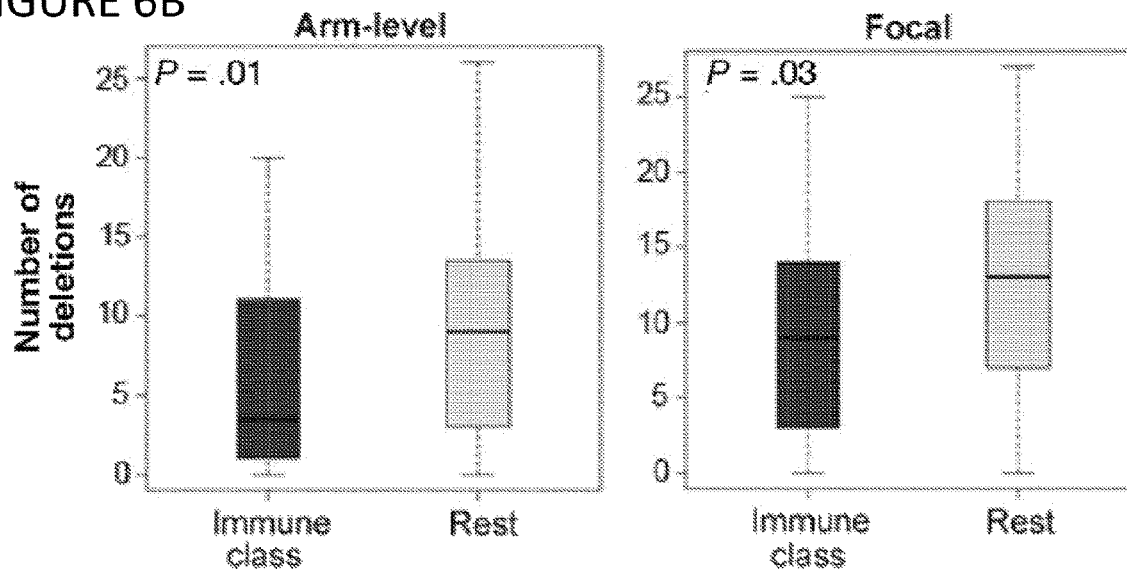

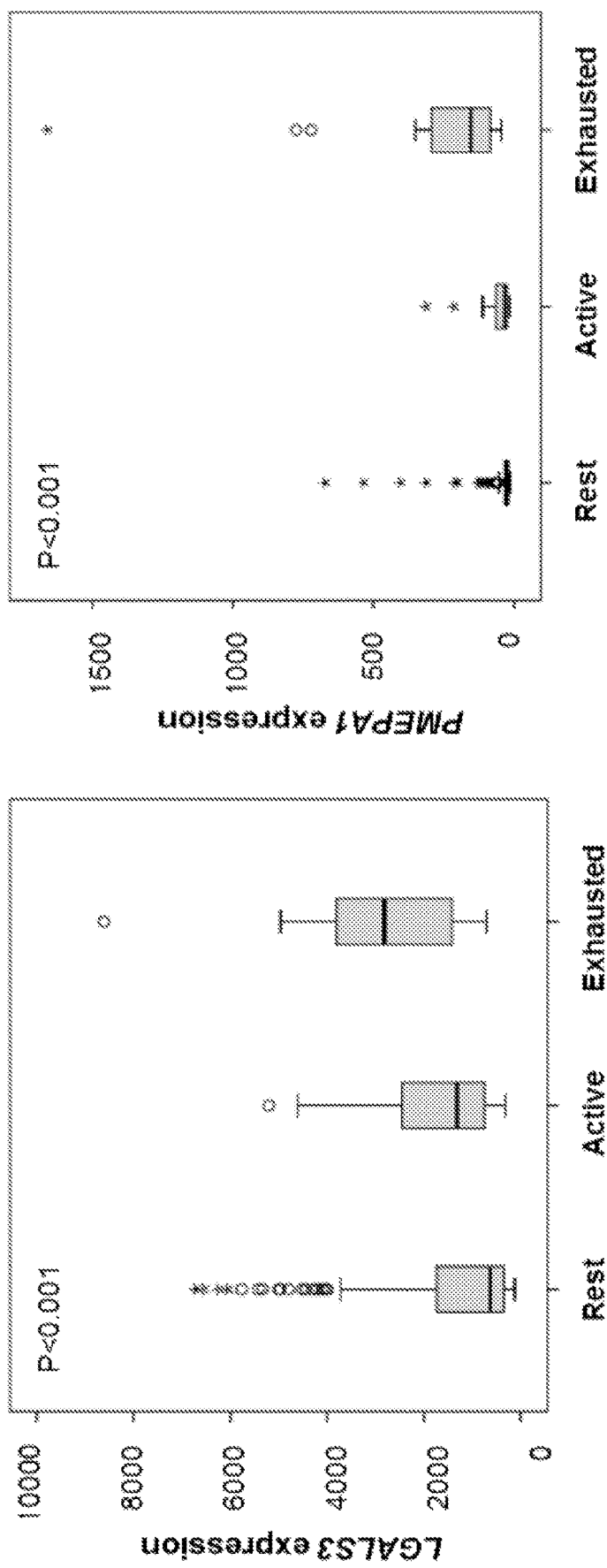

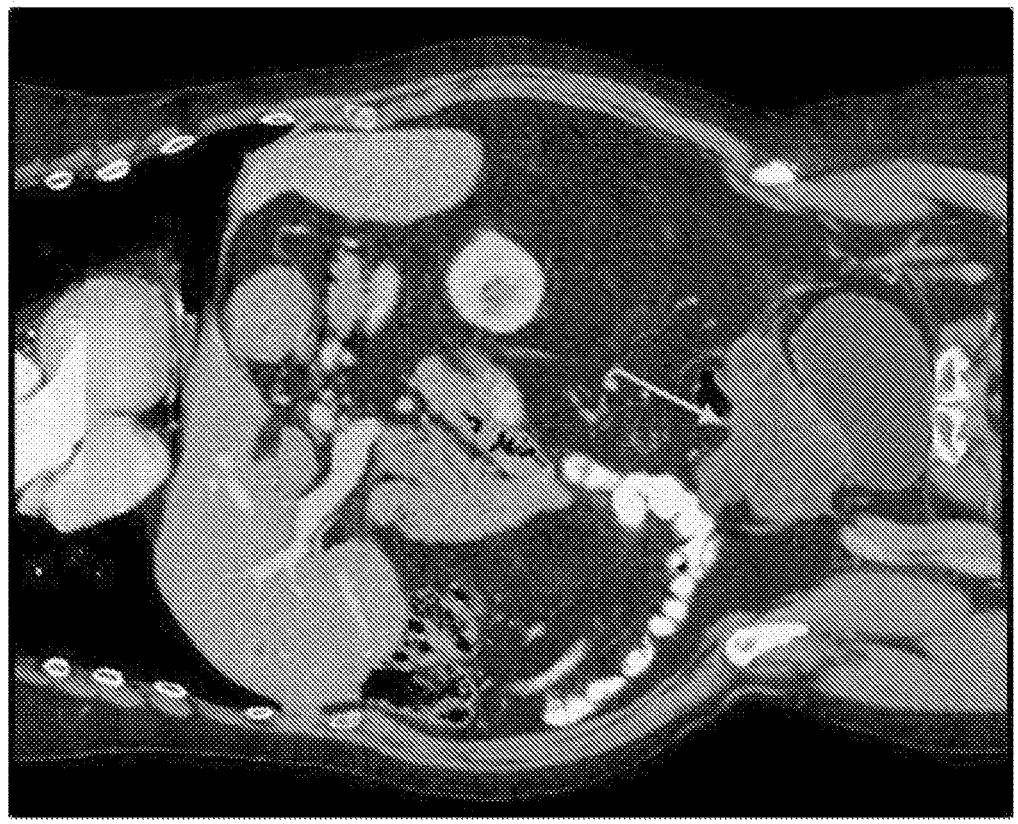
FIGURE 8B
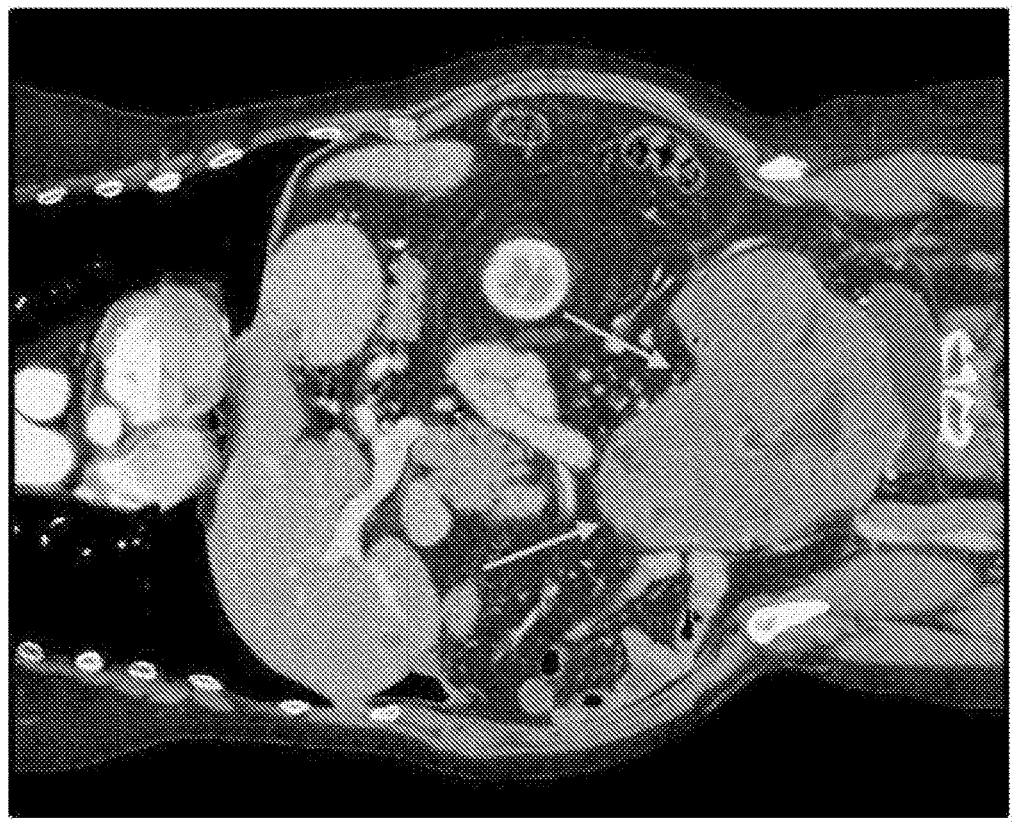
FIGURE 8
FIGURE 8A

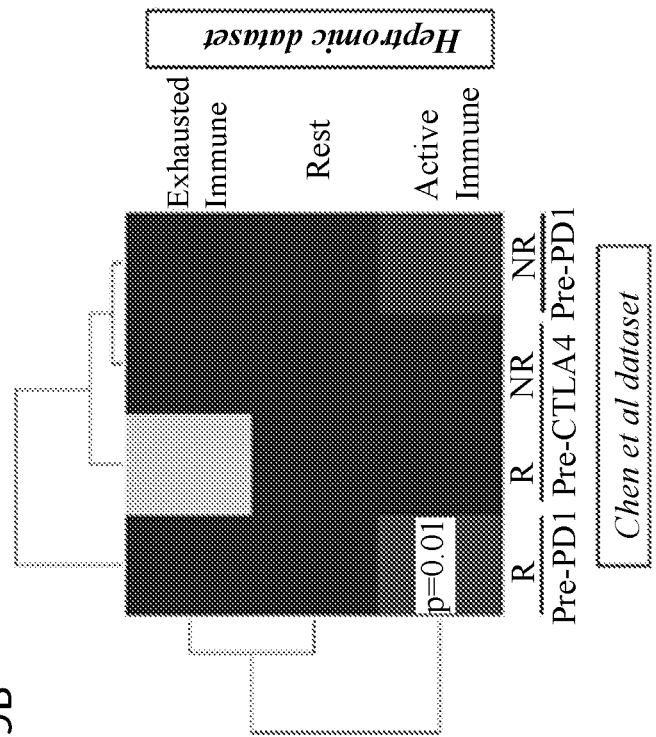
FIGURE 9A
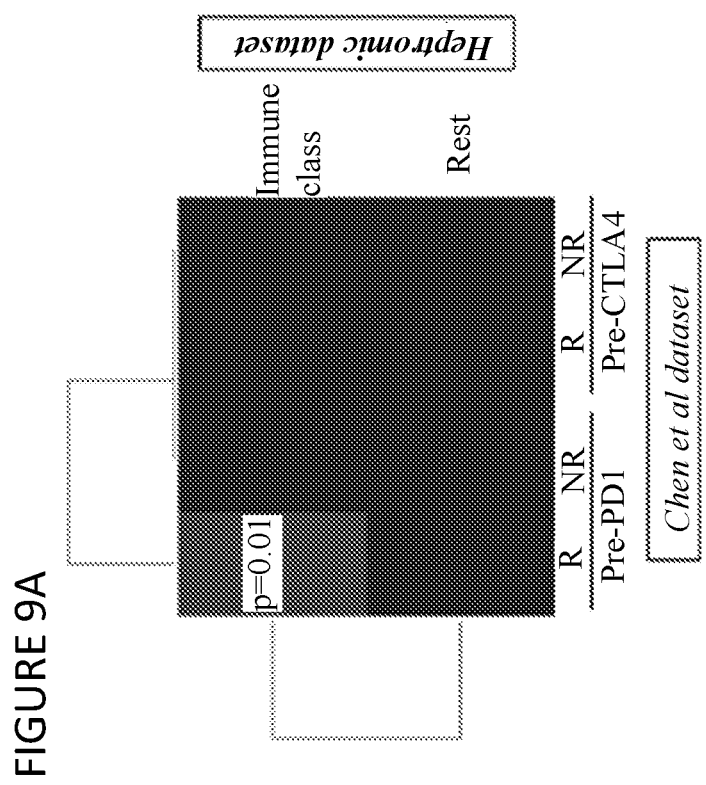
FIGURE 9B
FIGURE 9

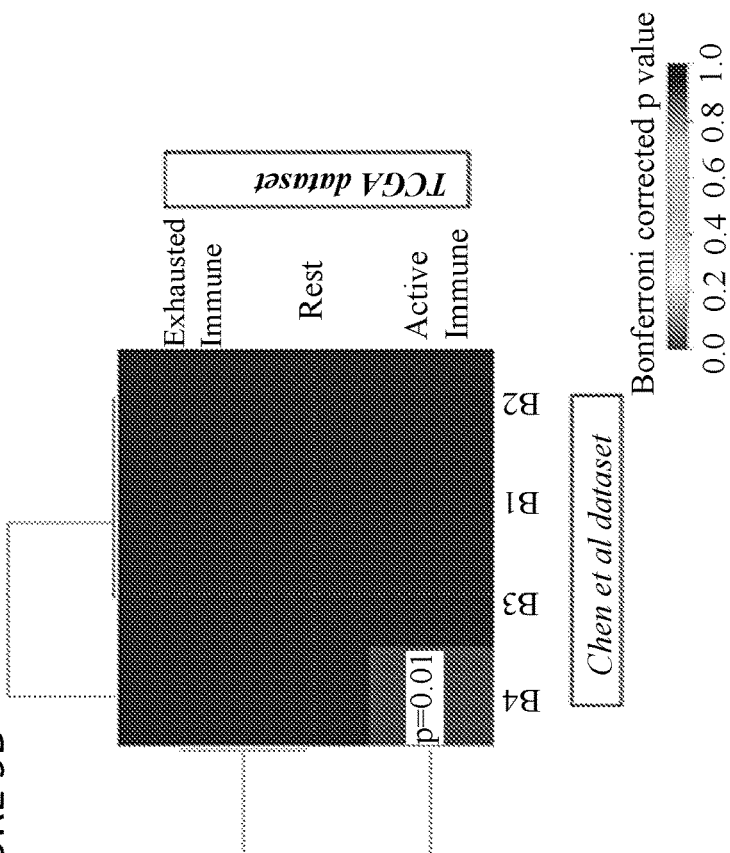
FIGURE 9D
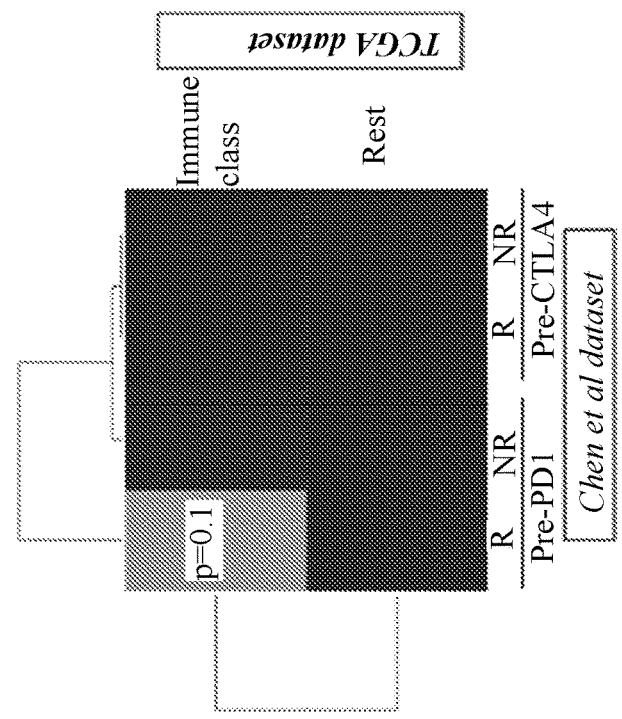
FIGURE 9C
FIGURE 9

FIGURE 10 A

| Gene name | class |
|---|---|
| PAGE4 | Rest |
| UGT2B17 | Rest |
| C1QTNF3 | Rest |
| DHRS2 | Rest |
| FAM133A | Rest |
| ASCL1 | Rest |
| NTN3 | Immune class |
| IGKC | Immune class |
| IGKV3D-11 | Immune class |
| IGLV1-44 | Immune class |
| IGJ | Immune class |
| CCL19 | Immune class |
| IGHG3 | Immune class |
| IGHA1 | Immune class |
| IGHM | Immune class |
| IGHG2 | Immune class |
| IGHG1 | Immune class |
| IGHA2 | Immune class |
| IGHM | Immune class |
| PTGDS | Immune class |
| POU2AF1 | Immune class |
| MMP7 | Immune class |
| MGC29506 | Immune class |
| CCL18 | Immune class |
| GBP5 | Immune class |
| CD52 | Immune class |
| TRBC1 | Immune class |
| GPR171 | Immune class |
| GEM | Immune class |
| CCL21 | Immune class |
| TARP | Immune class |
| CXCL9 | Immune class |

FIGURE 10B

| Gene | Class |
|---|---|
| CCL2 | Immune class |
| TRBC1 | Immune class |
| IGLJ3 | Immune class |
| CHIT1 | Immune class |
| MMP9 | Immune class |
| IGL@ | Immune class |
| HLA-DRB5 | Immune class |
| CXCR4 | Immune class |
| CD8A | Immune class |
| GZMB | Immune class |
| LUM | Immune class |
| TRBC2 | Immune class |
| CFTR | Immune class |
| GZMK | Immune class |
| CD53 | Immune class |
| PTX3 | Immune class |
| DCN | Immune class |
| CD48 | Immune class |
| PTPRC | Immune class |
| TRAC | Immune class |
| FYB | Immune class |
| AIM2 | Immune class |
| DUSP2 | Immune class |
| CYTIP | Immune class |
| CCL5 | Immune class |
| EFEMP1 | Immune class |
| LXN | Immune class |
| MMP12 | Immune class |
| AEBP1 | Immune class |
| IL7R | Immune class |
| CD38 | Immune class |
| POSTN | Immune class |
| CXCL14 | Immune class |
| FAM150B | Immune class |

FIGURE 10C

| Gene | Class |
|---|---|
| CCL4 | Immune class |
| STMN2 | Immune class |
| C11orf96 | Immune class |
| ID4 | Immune class |
| CR2 | Immune class |
| CXCL6 | Immune class |
| FNDC1 | Immune class |
| THBS2 | Immune class |
| LTB | Immune class |
| CLIC6 | Immune class |
| ITGB2 | Immune class |
| GZMH | Immune class |
| CCR7 | Immune class |
| LCP2 | Immune class |
| RGS1 | Immune class |
| CD2 | Immune class |
| SMOC2 | Immune class |
| LTBP2 | Immune class |
| GZMA | Immune class |
| COL1A2 | Immune class |
| MGP | Immune class |
| TAGLN | Immune class |
| CD3D | Immune class |
| RAC2 | Immune class |
| CD27 | Immune class |
| C16orf54 | Immune class |
| S100A4 | Immune class |
| CYR61 | Immune class |
| PTGIS | Immune class |
| COL6A3 | Immune class |
| SLA | Immune class |
| COL1A1 | Immune class |
| MTHFD2 | Immune class |
| SAMSN1 | Immune class |

FIGURE 10D

| | |
|---|---|
| PMP22 | Immune class |
| SRGN | Immune class |
| TIMP1 | Immune class |
| IGLV1-40 | Immune class |
| GABRP | Immune class |
| CTGF | Immune class |
| PMEPA1 | Immune class |
| C7 | Immune class |
| CORO1A | Immune class |
| MS4A1 | Immune class |
| FAM26F | Immune class |
| LAPTM5 | Immune class |

FIGURE 11A

| Feature | Fold Change |
|---|---|
| LCP2 | 3.35 |
| PTPRC | 4.06 |
| IGHG1 /// IGHV4-31 | 8.40 |
| IGHG1 /// IGHG2 /// IGHG3 /// IGHM /// IGHV4-31 | 9.08 |
| TRAC /// TRAJ17 /// TRAV20 | 4.04 |
| CCL5 | 3.76 |
| IGHG1 /// IGHG3 /// IGHM /// IGHV4-31 | 9.00 |
| LAPTM5 | 3.03 |
| GZMA | 3.26 |
| IGHG1 /// IGHM /// IGHV4-31 | 9.37 |
| TRBC2 | 4.42 |
| SLA | 3.15 |
| FYB | 3.88 |
| CD53 | 4.22 |
| IGHG3 /// IGHM | 10.04 |
| CD3D | 3.20 |
| GZMK | 4.30 |
| CD48 | 4.11 |
| CD2 | 3.29 |
| CD52 | 5.37 |
| TRBC1 | 5.27 |
| S100A4 | 3.18 |
| ITGB2 | 3.40 |
| TRBC1 /// TRBC2 | 4.91 |
| RAC2 | 3.19 |
| CORO1A | 3.05 |
| IL7R | 3.69 |
| CYTIP | 3.76 |
| SRGN | 3.09 |
| SAMSN1 | 3.11 |

FIGURE 11B

| | |
|---|---|
| FAM26F | 3.11 |
| GPR171 | 3.04 |
| CD27 | 5.20 |
| MTHFD2 | 3.18 |
| CXCR4 | 3.12 |
| TIMP1 | 4.51 |
| C16orf54 | 3.09 |
| CD8A | 3.18 |
| LUM | 4.50 |
| DUSP2 | 4.47 |
| POU2AF1 | 3.80 |
| EFEMP1 | 6.54 |
| CXCL9 | 3.74 |
| PMP22 | 4.94 |
| IGHM | 3.10 |
| LXN | 7.12 |
| TARP /// TRGC2 | 3.73 |
| DCN | 5.05 |
| RGS1 | 4.14 |
| THBS2 | 3.30 |
| PTGIS | 3.41 |
| SMOC2 | 3.16 |
| MMP9 | 3.29 |
| GZMH | 4.68 |
| AEBP1 | 3.39 |
| COL6A3 | 3.69 |
| GEM | 3.15 |
| CTGF | 5.18 |
| CCL19 | 3.06 |
| MGP | 10.33 |
| | 3.23 |

FIGURE 11C

| | |
|---|---|
| IGKC /// NTN3 | 16.82 |
| LTB | 3.40 |
| AIM2 | 3.86 |
| PTGDS | 6.69 |
| IGJ | 10.42 |
| C11orf96 | 3.61 |
| ID4 | 3.61 |
| CYR61 | 3.17 |
| TAGLN | 3.22 |
| LTBP2 | 3.28 |
| C7 | 3.05 |
| STMN2 | 3.61 |
| COL1A2 | 3.26 |
| CCL4 /// CCL4L1 /// CCL4L2 | 3.61 |
| CCR7 | 3.39 |
| MGC29506 | 6.28 |
| FNDC1 | 3.48 |
| COL1A1 | 3.14 |

FIGURE 11D

| | |
|---|---|
| MS4A1 | 3.04 |
| IGL@ | 4.59 |
| IGLV1-40 | 3.07 |
| CCL21 | 5.17 |
| CD38 | 3.68 |
| CCL18 | 5.93 |
| IGHA2 //// LOC100126583 | 7.81 |
| IGKC //// LOC652694 | 15.85 |
| GZMB | 4.47 |
| IGHA1 //// IGHA2 //// LOC100126583 | 9.83 |
| CCL2 | 4.92 |
| IGKV3D-11 | 12.06 |
| CHIT1 | 4.70 |
| PMEPA1 | 3.06 |
| IGHA1 //// LOC100126583 | 8.98 |
| GBP5 | 5.53 |
| IGLV1-44 | 11.38 |
| POSTN | 3.66 |
| HLA-DRB5 | 4.53 |
| CXCL14 | 3.65 |
| CFTR | 4.39 |
| FAM150B | 3.63 |
| CLIC6 | 3.40 |
| CXCL6 | 3.56 |
| CR2 | 3.59 |
| GABRP | 3.06 |
| PTX3 | 4.22 |
| MMP12 | 3.69 |
| MMP7 | 6.41 |
| IGLJ3 //// IGLV3-19 | 4.83 |

FIGURE 12A

| NAME |
|---|
| GU_PDEF_TARGETS_UP |
| MCBRYAN_PUBERTAL_BREAST_4_5WK_UP |
| PID_AVB3_INTEGRIN_PATHWAY |
| PID_SYNDECAN_1_PATHWAY |
| LIU_SMARCA4_TARGETS |
| WANG_SMARCE1_TARGETS_UP |
| LEE_NEURAL_CREST_STEM_CELL_UP |
| CERVERA_SDHB_TARGETS_1_UP |
| REACTOME_COLLAGEN_FORMATION |
| URS_ADIPOCYTE_DIFFERENTIATION_DN |
| CHIARADONNA_NEOPLASTIC_TRANSFORMATION_KRAS_DN |
| TURASHVILI_BREAST_LOBULAR_CARCINOMA_VS_DUCTAL_NORMAL_UP |
| BOQUEST_STEM_CELL_UP |
| ZHU_CMV_ALL_DN |
| WU_CELL_MIGRATION |
| CHARAFE_BREAST_CANCER_BASAL_VS_MESENCHYMAL_DN |
| NABA_CORE_MATRISOME |
| KANG_AR_TARGETS_DN |
| NAKAMURA_CANCER_MICROENVIRONMENT_UP |
| ZHU_CMV_24_HR_DN |
| PID_INTEGRIN1_PATHWAY |
| SENMJA_ISLET_HNF1A_TARGETS_UP |
| WESTON_VEGFA_TARGETS_6HR |
| PASINI_SUZ12_TARGETS_DN |
| KEGG_ECM_RECEPTOR_INTERACTION |
| REACTOME_EXTRACELLULAR_MATRIX_ORGANIZATION |
| PICCALUGA_ANGIOIMMUNOBLASTIC_LYMPHOMA_UP |
| NEWMAN_ERCC6_TARGETS_DN |
| WILCOX_RESPONSE_TO_PROGESTERONE_DN |
| LI_WILMS_TUMOR_VS_FETAL_KIDNEY_2_DN |
| ROZANOV_MMP14_TARGETS_SUBSET |
| BURTON_ADIPOGENESIS_7 |
| REN_ALVEOLAR_RHABDOMYOSARCOMA_DN |
| TURASHVILI_BREAST_LOBULAR_CARCINOMA_VS_LOBULAR_NORMAL_DN |
| VECCHI_GASTRIC_CANCER_ADVANCED_VS_EARLY_UP |
| NABA_ECM_GLYCOPROTEINS |
| VANTVEER_BREAST_CANCER_BRCA1_DN |
| VERRECCHIA_EARLY_RESPONSE_TO_TGFB1 |
| LIU_PROSTATE_CANCER_DN |
| BRUECKNER_TARGETS_OF_MIRLET7A3_DN |
| CHIANG_LIVER_CANCER_SUBCLASS_CTNNB1_DN |
| BERTUCCI_MEDULLARY_VS_DUCTAL_BREAST_CANCER_DN |
| KAAB_HEART_ATRIUM_VS_VENTRICLE_UP |
| ISSAEVA_MLL2_TARGETS |
| PID_INTEGRIN3_PATHWAY |
| GOTZMANN_EPITHELIAL_TO_MESENCHYMAL_TRANSITION_UP |

FIGURE 12B

| |
|---|
| VANHARANTA_UTERINE_FIBROID_UP |
| LIM_MAMMARY_LUMINAL_MATURE_DN |
| LINDVALL_IMMORTALIZED_BY_TERT_DN |
| RODWELL_AGING_KIDNEY_NO_BLOOD_UP |
| MANALO_HYPOXIA_UP |
| NABA_COLLAGENS |
| IZADPANAH_STEM_CELL_ADIPOSE_VS_BONE_DN |
| WESTON_VEGFA_TARGETS |
| ZWANG_CLASS_2_TRANSIENTLY_INDUCED_BY_EGF |
| REACTOME_NCAM1_INTERACTIONS |
| SANA_TNF_SIGNALING_DN |
| BASSO_HAIRY_CELL_LEUKEMIA_DN |
| PETROVA_ENDOTHELIUM_LYMPHATIC_VS_BLOOD_DN |
| CHIARADONNA_NEOPLASTIC_TRANSFORMATION_KRAS_CDC25_DN |
| WATANABE_ULCERATIVE_COLITIS_WITH_CANCER_UP |
| KAYO_CALORIE_RESTRICTION_MUSCLE_UP |
| ONDER_CDH1_TARGETS_2_UP |
| GERHOLD_ADIPOGENESIS_DN |
| JECHLINGER_EPITHELIAL_TO_MESENCHYMAL_TRANSITION_UP |
| DELYS_THYROID_CANCER_UP |
| ZHANG_TLX_TARGETS_60HR_UP |
| KINSEY_TARGETS_OF_EWSR1_FLI1_FUSION_DN |
| SWEET_KRAS_TARGETS_UP |
| NABA_PROTEOGLYCANS |
| HALMOS_CEBPA_TARGETS_DN |
| DAVICIONI_MOLECULAR_ARMS_VS_ERMS_DN |
| MIYAGAWA_TARGETS_OF_EWSR1_ETS_FUSIONS_DN |
| CHIBA_RESPONSE_TO_TSA_UP |
| SUNG_METASTASIS_STROMA_UP |
| BURTON_ADIPOGENESIS_B |
| CHIARADONNA_NEOPLASTIC_TRANSFORMATION_CDC25_DN |
| SASAI_RESISTANCE_TO_NEOPLASTIC_TRANSFROMATION |
| SCHUETZ_BREAST_CANCER_DUCTAL_INVASIVE_UP |
| TONKS_TARGETS_OF_RUNX1_RUNX1T1_FUSION_SUSTAINDED_IN_ERYTHROCYTE_UP |
| LEE_LIVER_CANCER_E2F1_UP |
| LEE_LIVER_CANCER_DENA_UP |
| WESTON_VEGFA_TARGETS_12HR |
| CROMER_TUMORIGENESIS_UP |
| KEEN_RESPONSE_TO_ROSIGLITAZONE_DN |
| VART_KSHV_INFECTION_ANGIOGENIC_MARKERS_DN |
| REACTOME_INTEGRIN_CELL_SURFACE_INTERACTIONS |
| DAVICIONI_TARGETS_OF_PAX_FOXO1_FUSIONS_UP |
| WOO_LIVER_CANCER_RECURRENCE_UP |
| IGLESIAS_E2F_TARGETS_UP |
| LINDGREN_BLADDER_CANCER_HIGH_RECURRENCE |
| HELLEBREKERS_SILENCED_DURING_TUMOR_ANGIOGENESIS |
| VALK_AML_CLUSTER_10 |
| REACTOME_NCAM_SIGNALING_FOR_NEURITE_OUT_GROWTH |

FIGURE 12C

- LEE_LIVER_CANCER_ACOX1_UP
- KEGG_FOCAL_ADHESION
- CLASPER_LYMPHATIC_VESSELS_DURING_METASTASIS_DN
- VERRECCHIA_RESPONSE_TO_TGFB1_C1
- YAMAZAKI_TCEB3_TARGETS_UP
- CUI_TCF21_TARGETS_UP
- SENESE_HDAC1_TARGETS_DN
- SCHRAETS_MLL_TARGETS_DN
- MOROSETTI_FACIOSCAPULOHUMERAL_MUSCULAR_DYSTROPHY_UP
- DACOSTA_ERCC3_ALLELE_XPCS_VS_TTD_DN
- JI_CARCINOGENESIS_BY_KRAS_AND_STK11_DN
- TSENG_ADIPOGENIC_POTENTIAL_UP
- VERRECCHIA_RESPONSE_TO_TGFB1_C2
- LANDIS_BREAST_CANCER_PROGRESSION_DN
- REACTOME_DEGRADATION_OF_THE_EXTRACELLULAR_MATRIX
- DELPUECH_FOXO3_TARGETS_UP
- WONG_ENDMETRIUM_CANCER_DN
- PANGAS_TUMOR_SUPPRESSION_BY_SMAD1_AND_SMAD5_UP
- CHARAFE_BREAST_CANCER_LUMINAL_VS_MESENCHYMAL_DN
- TORCHIA_TARGETS_OF_EWSR1_FLI1_FUSION_TOP20_UP
- REACTOME_AXON_GUIDANCE
- WIEDERSCHAIN_TARGETS_OF_BMI1_AND_PCGF2
- ZHAN_MULTIPLE_MYELOMA_MS_UP
- SIMBULAN_PARP1_TARGETS_UP
- CAIRO_LIVER_DEVELOPMENT_UP
- GAJATE_RESPONSE_TO_TRABECTEDIN_UP
- LABBE_TGFB1_TARGETS_UP
- HENDRICKS_SMARCA4_TARGETS_UP
- HOELZEL_NF1_TARGETS_DN
- MCBRYAN_PUBERTAL_TGFB1_TARGETS_UP
- LIM_MAMMARY_STEM_CELL_UP
- LIEN_BREAST_CARCINOMA_METAPLASTIC
- ANASTASSIOU_CANCER_MESENCHYMAL_TRANSITION_SIGNATURE
- BIOCARTA_UCALPAIN_PATHWAY
- XU_HGF_TARGETS_INDUCED_BY_AKT1_48HR_UP
- ONDER_CDH1_SIGNALING_VIA_CTNNB1
- NAKAMURA_ADIPOGENESIS_EARLY_DN
- LABBE_TARGETS_OF_TGFB1_AND_WNT3A_UP
- HUMMERICH_SKIN_CANCER_PROGRESSION_UP
- NABA_BASEMENT_MEMBRANES
- TURASHVILI_BREAST_DUCTAL_CARCINOMA_VS_DUCTAL_NORMAL_DN
- VALK_AML_CLUSTER_9
- TIMOFEEVA_GROWTH_STRESS_VIA_STAT1_DN
- PID_INTEGRIN_A4B1_PATHWAY
- FONTAINE_PAPILLARY_THYROID_CARCINOMA_UP
- YAO_TEMPORAL_RESPONSE_TO_PROGESTERONE_CLUSTER_16
- TONKS_TARGETS_OF_RUNX1_RUNX1T1_FUSION_HSC_UP
- CHANDRAN_METASTASIS_DN

FIGURE 12D

- LY_AGING_MIDDLE_UP
- BORLAK_LIVER_CANCER_EGF_UP
- TONKS_TARGETS_OF_RUNX1_RUNX1T1_FUSION_ERYTHROCYTE_UP
- BERENJENO_TRANSFORMED_BY_RHOA_DN
- KANG_AR_TARGETS_UP
- VERRECCHIA_DELAYED_RESPONSE_TO_TGFB1
- ROY_WOUND_BLOOD_VESSEL_UP
- CROONQUIST_STROMAL_STIMULATION_UP
- DELACROIX_RARG_BOUND_MEF
- SWEET_LUNG_CANCER_KRAS_DN
- TRAYNOR_RETT_SYNDROM_DN
- MISHRA_CARCINOMA_ASSOCIATED_FIBROBLAST_UP
- TERAMOTO_OPN_TARGETS_CLUSTER_4
- MISHRA_CARCINOMA_ASSOCIATED_FIBROBLAST_DN
- SENESE_HDAC1_AND_HDAC2_TARGETS_DN
- APRELIKOVA_BRCA1_TARGETS
- CHIARADONNA_NEOPLASTIC_TRANSFORMATION_CDC25_UP
- RUIZ_TNC_TARGETS_UP
- MEINHOLD_OVARIAN_CANCER_LOW_GRADE_UP
- WAMUNYOKOLI_OVARIAN_CANCER_GRADES_1_2_DN
- STEGER_ADIPOGENESIS_DN
- GENTILE_UV_LOW_DOSE_DN
- VALK_AML_CLUSTER_2
- INGRAM_SHH_TARGETS_DN
- DUTERTRE_ESTRADIOL_RESPONSE_24HR_DN
- FRIDMAN_SENESCENCE_UP
- REACTOME_DEVELOPMENTAL_BIOLOGY
- BAELDE_DIABETIC_NEPHROPATHY_UP
- ZHENG_GLIOBLASTOMA_PLASTICITY_DN
- XU_GH1_AUTOCRINE_TARGETS_DN
- RIGGI_EWING_SARCOMA_PROGENITOR_DN
- REACTOME_CHONDROITIN_SULFATE_DERMATAN_SULFATE_METABOLISM
- KIM_WT1_TARGETS_12HR_UP
- YAWASHITA_LIVER_CANCER_STEM_CELL_UP
- VALK_AML_WITH_EVI1
- BURTON_ADIPOGENESIS_9
- HARRIS_BRAIN_CANCER_PROGENITORS
- KHETCHOUMIAN_TRIM24_TARGETS_UP
- PEDERSEN_METASTASIS_BY_ERBB2_ISOFORM_1
- PID_INTEGRIN_A9B1_PATHWAY
- WANG_BARRETTS_ESOPHAGUS_UP
- PEDERSEN_TARGETS_OF_611CTF_ISOFORM_OF_ERBB2
- MARCHINI_TRABECTEDIN_RESISTANCE_DN
- DAZARD_UV_RESPONSE_CLUSTER_G4
- BROWNE_HCMV_INFECTION_24HR_DN
- CHANG_POU5F1_TARGETS_UP
- HOSHIDA_LIVER_CANCER_SURVIVAL_UP
- BROWNE_HCMV_INFECTION_18HR_DN

FIGURE 12E

| |
|---|
| REACTOME_SIGNALING_BY_PDGF |
| DELASERNA_MYOD_TARGETS_DN |
| JECHLINGER_EPITHELIAL_TO_MESENCHYMAL_TRANSITION_DN |
| BURTON_ADIPOGENESIS_PEAK_AT_0HR |
| REACTOME_SIGNAL_TRANSDUCTION_BY_L1 |
| NAKAMURA_ADIPOGENESIS_LATE_DN |
| KORKOLA_TERATOMA_UP |
| LEE_LIVER_CANCER_MYC_E2F1_UP |
| FRIDMAN_IMMORTALIZATION_DN |
| DANG_REGULATED_BY_MYC_DN |
| BOYAULT_LIVER_CANCER_SUBCLASS_G56_DN |
| DURAND_STROMA_S_UP |
| NIELSEN_GIST_VS_SYNOVIAL_SARCOMA_UP |
| CERVERA_SDHB_TARGETS_2 |
| KOYAMA_SEMA3B_TARGETS_UP |
| TURASHVILI_BREAST_DUCTAL_CARCINOMA_VS_LOBULAR_NORMAL_DN |
| GUENTHER_GROWTH_SPHERICAL_VS_ADHERENT_DN |
| LIU_IL13_PRIMING_MODEL |
| COLIN_PILOCYTIC_ASTROCYTOMA_VS_GLIOBLASTOMA_DN |
| BERENJENO_ROCK_SIGNALING_NOT_VIA_RHOA_DN |
| GAUSSMANN_MLL_AF4_FUSION_TARGETS_F_UP |
| VART_KSHV_INFECTION_ANGIOGENIC_MARKERS_UP |
| HUMMERICH_SKIN_CANCER_PROGRESSION_DN |
| BERENJENO_TRANSFORMED_BY_RHOA_REVERSIBLY_DN |
| KEGG_TGF_BETA_SIGNALING_PATHWAY |
| GAUSSMANN_MLL_AF4_FUSION_TARGETS_E_UP |
| FARMER_BREAST_CANCER_CLUSTER_4 |
| BEGUM_TARGETS_OF_PAX3_FOXO1_FUSION_DN |
| ROZANOV_MMP14_TARGETS_UP |
| MCBRYAN_PUBERTAL_BREAST_3_4WK_UP |
| DORN_ADENOVIRUS_INFECTION_24HR_UP |
| TSUNODA_CISPLATIN_RESISTANCE_UP |
| NING_CHRONIC_OBSTRUCTIVE_PULMONARY_DISEASE_UP |
| HAN_JNK_SINGALING_DN |
| SCHLINGEMANN_SKIN_CARCINOGENESIS_TPA_DN |
| PID_UPA_UPAR_PATHWAY |
| PID_ALK1_PATHWAY |
| PAPASPYRIDONOS_UNSTABLE_ATEROSCLEROTIC_PLAQUE_DN |
| SESTO_RESPONSE_TO_UV_C8 |
| SENESE_HDAC2_TARGETS_DN |
| PID_WNT_SIGNALING_PATHWAY |
| REACTOME_A_TETRASACCHARIDE_LINKER_SEQUENCE_IS_REQUIRED_FOR_GAG_SYN |
| FOURNIER_ACINAR_DEVELOPMENT_LATE_UP |
| BIOCARTA_NDKDYNAMIN_PATHWAY |
| ASTON_MAJOR_DEPRESSIVE_DISORDER_UP |
| WANG_LSD1_TARGETS_UP |
| ABBUD_LIF_SIGNALING_2_UP |
| CLASPER_LYMPHATIC_VESSELS_DURING_METASTASIS_UP |

FIGURE 12F

| |
|---|
| BOQUEST_STEM_CELL_CULTURED_VS_FRESH_UP |
| VERNELL_RETINOBLASTOMA_PATHWAY_DN |
| JI_METASTASIS_REPRESSED_BY_STK11 |
| SCHAEFFER_PROSTATE_DEVELOPMENT_48HR_DN |
| QI_PLASMACYTOMA_DN |
| POMEROY_MEDULLOBLASTOMA_DESMOPLASIC_VS_CLASSIC_DN |
| KYNG_ENVIRONMENTAL_STRESS_RESPONSE_UP |
| WEINMANN_ADAPTATION_TO_HYPOXIA_DN |
| CHEBOTAEV_GR_TARGETS_DN |
| PETRETTO_CARDIAC_HYPERTROPHY |
| TANG_SENESCENCE_TP53_TARGETS_UP |
| KIM_GLIS2_TARGETS_UP |
| BROWNE_HCMV_INFECTION_16HR_DN |
| PID_TRKR_PATHWAY |
| HUANG_FOXA2_TARGETS_DN |
| SIMBULAN_UV_RESPONSE_NORMAL_DN |
| JOHNSTONE_PARVB_TARGETS_3_UP |
| VERRECCHIA_RESPONSE_TO_TGFB1_C3 |
| BURTON_ADIPOGENESIS_1 |
| GERHOLD_RESPONSE_TO_TZD_DN |
| DASU_IL6_SIGNALING_SCAR_DN |
| REACTOME_CHONDROITIN_SULFATE_BIOSYNTHESIS |
| VERRECCHIA_RESPONSE_TO_TGFB1_C6 |
| PID_A6B1_A6B4_INTEGRIN_PATHWAY |
| WAMUNYOKOLI_OVARIAN_CANCER_LMP_DN |
| VERHAAK_GLIOBLASTOMA_MESENCHYMAL |
| KANNAN_TP53_TARGETS_UP |
| HUANG_DASATINIB_RESISTANCE_UP |
| TONKS_TARGETS_OF_RUNX1_RUNX1T1_FUSION_SUSTAINED_IN_GRANULOCYTE_UP |
| HAEGERSTRAND_RESPONSE_TO_IMATINIB |
| NADLER_OBESITY_UP |
| OXFORD_RALB_TARGETS_UP |
| GILDEA_METASTASIS |
| LI_WILMS_TUMOR_VS_FETAL_KIDNEY_1_UP |
| REACTOME_OTHER_SEMAPHORIN_INTERACTIONS |
| BURTON_ADIPOGENESIS_PEAK_AT_2HR |
| NAKAJIMA_MAST_CELL |
| DAVICIONI_RHABDOMYOSARCOMA_PAX_FOXO1_FUSION_DN |
| INGRAM_SHH_TARGETS_UP |
| SCHRAETS_MLL_TARGETS_UP |
| BIOCARTA_PTDINS_PATHWAY |
| JOHANSSON_BRAIN_CANCER_EARLY_VS_LATE_DN |
| TOMLINS_METASTASIS_DN |
| ZHONG_SECRETOME_OF_LUNG_CANCER_AND_FIBROBLAST |
| LEE_AGING_MUSCLE_UP |

| |
|---|
| HALLMARK_EPITHELIAL_MESENCHYMAL_TRANSITION |
| HALLMARK_ANGIOGENESIS |

FIGURE 12G

| |
|---|
| HALLMARK_TGF_BETA_SIGNALING |
| HALLMARK_MYOGENESIS |
| HALLMARK_APICAL_JUNCTION |
| HALLMARK_UV_RESPONSE_DN |
| HALLMARK_HYPOXIA |
| HALLMARK_NOTCH_SIGNALING |
| EXTRACELLULAR_MATRIX |
| PROTEINACEOUS_EXTRACELLULAR_MATRIX |
| SKELETAL_DEVELOPMENT |
| EXTRACELLULAR_MATRIX_PART |
| EXTRACELLULAR_MATRIX_STRUCTURAL_CONSTITUENT |
| ESC_V6.5_UP_EARLY.V1_DN |
| ESC_J1_UP_LATE.V1_UP |
| CRX_DN.V1_DN |
| ATF2_S_UP.V1_DN |
| CAHOY_ASTROGLIAL |
| MEK_UP.V1_UP |
| ESC_V6.5_UP_LATE.V1_UP |
| P53_DN.V1_UP |
| ATF2_UP.V1_DN |
| HINATA_NFKB_MATRIX |
| ERB2_UP.V1_UP |
| CORDENONSI_YAP_CONSERVED_SIGNATURE |
| E2F1_UP.V1_DN |
| BMI1_DN.V1_UP |
| TGFB_UP.V1_UP |

FIGURE 13

| Focal high-level amplifications (HLA) | | Immune class (# of samples) | | | | | | Rest (# of samples) | | STATISTICS | | | |
|---|---|---|---|---|---|---|---|---|---|---|---|---|---|
| | | Exhausted | | Active | | Total | | Rest | | Exhausted vs Active | Exhausted vs Rest | Active vs Rest | Immune vs Rest |
| Region | Gene | HLA | No HLA | HLA | No HLA | HLA | No HLA | HLA | No HLA | p_value | p_value | p_value | p_value |
| 5p15.33 | TERT | 1 | 20 | 0 | 21 | 1 | 41 | 7 | 141 | 1.000 | 1.000 | 0.60 | 0.69 |
| 6p21.1 | VEGFA | 0 | 21 | 2 | 19 | 2 | 40 | 12 | 136 | 0.488 | 0.355 | 0.69 | 0.74 |
| 7q31.2 | MET | 0 | 21 | 0 | 21 | 0 | 42 | 5 | 143 | 1.000 | 1.000 | 1.00 | 0.59 |
| 6q24.21 | MYC | 0 | 21 | 2 | 19 | 2 | 40 | 12 | 136 | 0.488 | 0.355 | 0.69 | 0.74 |
| 11q13.3 | CCND1 | 2 | 19 | 6 | 15 | 8 | 34 | 6 | 142 | 0.238 | 0.260 | 0.00 | 0.00 |

| Homozygous Deletion (HD) | | Exhausted | | Active | | Total | | Rest | | Exhausted vs Active | Exhausted vs Rest | Active vs Rest | Immune vs Rest |
|---|---|---|---|---|---|---|---|---|---|---|---|---|---|
| Region | Gene | HD | No HD | HD | No HD | HD | No HD | HD | No HD | p_value | p_value | p_value | p_value |
| 4q35.1 | IRF2 | 0 | 21 | 0 | 21 | 0 | 42 | 8 | 140 | 1.00 | 0.60 | 0.60 | 0.20 |
| 9p21.3 | CDKN2A | 0 | 21 | 0 | 21 | 0 | 42 | 10 | 138 | 1.00 | 0.61 | 0.61 | 0.12 |
| 9q31.3 | PTPN3 | 0 | 21 | 1 | 20 | 1 | 41 | 4 | 144 | 1.00 | 1.00 | 0.49 | 1.00 |
| 10q23.31 | PTEN | 0 | 21 | 1 | 20 | 1 | 41 | 8 | 140 | 1.00 | 0.60 | 1.00 | 0.69 |

FIGURE 14
FIGURE 14A
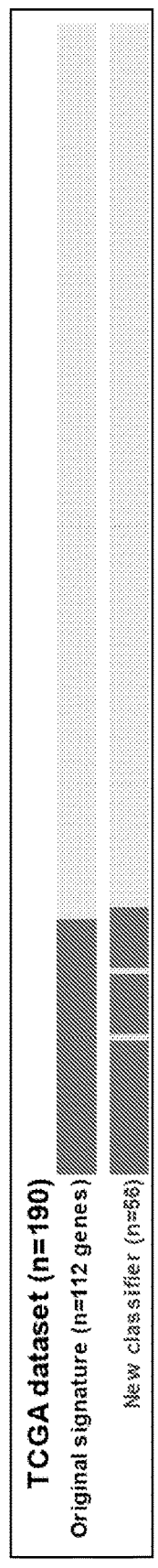
FIGURE 14B
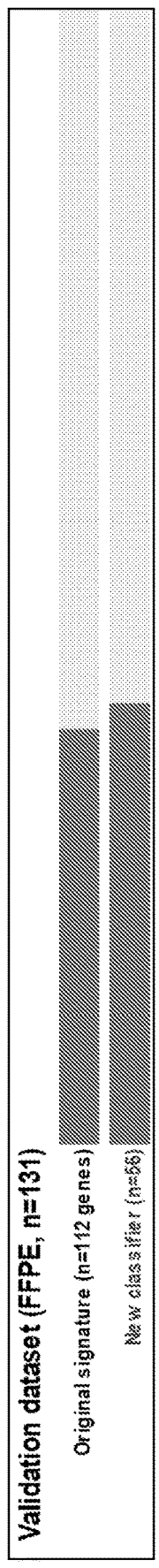
FIGURE 14C
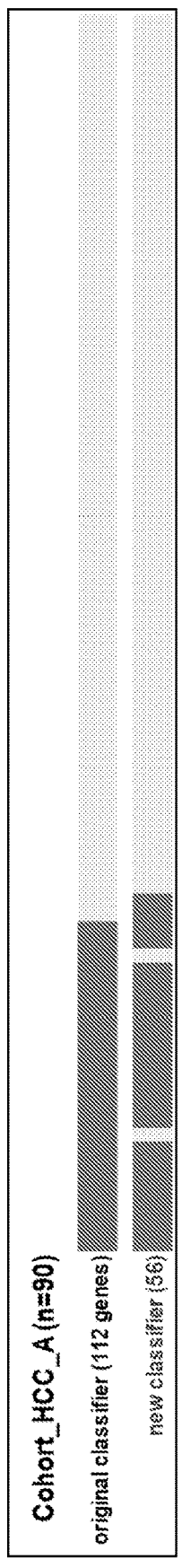

METHODS FOR THE DETECTION AND TREATMENT OF CLASSES OF HEPATOCELLULAR CARCINOMA RESPONSIVE TO IMMUNOTHERAPY

CROSS REFERENCE TO RELATED APPLICATION

The present application is a U.S. National Phase Application under 35 U.S.C. § 371 of International Patent Application No. PCT/US2018/037579, filed Jun. 14, 2018, which claims priority to U.S. Patent Application Ser. No. 62/519,711 filed Jun. 14, 2017 and U.S. Patent Application Ser. No. 62/629,231 filed Feb. 12, 2018, both of which are hereby incorporated by reference in their entirety.

FIELD OF THE INVENTION

The present invention relates to methods for detecting, diagnosing, prognosing, monitoring, and treating a patient with hepatocellular carcinoma. In particular, the invention provides diagnostic markers for the detection and treatment of patients who would benefit from immunotherapy, i.e., patient who would be most responsive to immunotherapy.

BACKGROUND OF THE INVENTION

Hepatocellular carcinoma (HCC) is the second leading cause of cancer-related mortality worldwide. The number of HCC deaths (approximately 800,000 per year) overlap with that of new cases, a testament to its high lethality (Murray, et al. 2012; Llovet, et al. 2016). This malignancy often occurs in the setting of chronic inflammatory liver disease (e.g., cirrhosis) and is associated with well-defined risk factors such as hepatitis B virus (HBV), hepatitis C virus (HCV), alcohol abuse, metabolic syndrome and diabetes (Llovet, et al. 2016). Over the past decade, major advancements have elucidated the molecular pathogenesis of HCC (Zucman-Rossi, et al. 2015), and yet, current therapeutic options remain very limited. Only a minority of HCC patients are diagnosed at early stages when curative approaches, such as surgical resection, transplantation or local ablation, are effective. In patients at advanced stages, the only systemic therapies that increase survival are the multi-tyrosine kinase inhibitors sorafenib (first line) (Llovet, et al. 2008) and regorafenib (second line) (Bruix, et al. 2017). Nonetheless, even with the survival benefits provided by these agents, the median life expectancy is of less than 2 years.

HCCs comprise a mixture of cell types, including malignant hepatocytes, immune cells, and endothelial cells dispersed within the extracellular matrix and supporting stroma. Previous studies have established a set of analytical approaches to virtually dissect the molecular signals deriving from these distinct compartments (Moffitt, et al. 2013).

In recent years, immune checkpoint inhibitors, which unleash the body's own immune response to attack tumors by targeting regulatory pathways in T cells, have shown remarkable efficacy in different solid cancers. This has led to the Food and Drug Administration (FDA) approval of four immune-based agents, which include monoclonal antibodies directed against the cytotoxic T-lymphocyte protein (CTLA-4), the programmed cell death protein 1 (PD-1) and its ligand PD-L1, for the treatment of advanced stage malignancies such as melanoma or lung cancer. These agents, ipilimumab, nivolumab, pembrolizumab, and atezolimumab, have significantly improved survival of these patients (Llovet, et al. 2015). These compounds elicit durable clinical responses and long-term remissions in a fraction of patients with metastatic disease (Zou, et al. 2016; Khalil, et al. 2016). Given that these therapies are directed to immune cells rather than tumor cells, they can be effective in a broad range of cancer types, with important activity recently reported in both solid and hematologic malignancies including bladder and colorectal cancer (Topalian, et al. 2012; Le, et al. 2015). Intriguingly, though, not all patients have the same likelihood of responding to these regimens (Zou, et al., 2016).

Given the promise of these therapies and the conflicting evidence of which patients may benefit from them, there has been a push for finding reliable biomarkers to predict positive outcomes of immunotherapy. One such biomarker is the expression of the protein PD-L1. Initial trials with non-small cell lung cancer have suggested that patients who are positive for PD-L1 expression have a greater overall response compared to patients negative for PD-L1 (Herbst, et al. 2016; Garon, et al. 2015; Topalian, et al. 2012).

However, due to its low accuracy and mixed results, immunohistochemistry (IHC)-based detection of PD-L1 is not reliable in determining and predicting a patient's response to immunotherapy. To start, there are technical issues with the procedure. IHC-based detection is subjective in terms of defining a "positive" tumor PD-L1 staining and the use of different cut-off values for positive staining There is also evidence of variability in pathologists' findings using the same assays (Brunnstrom, et al. 2017; Wang, et al. 2016).

Additionally, antibodies used in different studies have different sensitivities. At least seven different antibodies have been used in various studies of PD-L1 using IHC. The use of the different PD-L1 antibodies is a further reason that there is a variation of PD-L1 expression in tumors across various studies. See generally Wang, et al. 2016.

Accuracy of IHC protocols also depend upon biological, e.g., temporal and spatial, factors. In other words, PD-L1 expression in tumors is not uniform over time and area. For example, specimens obtained when PD-L1 overexpression in the tumor has already taken place (temporal) or a sample obtained from the patient missed the pertinent tumor-immune interface (spatial) leads to inaccuracies in measuring PD-L1 by IHC (Latchman, et al. 2001). The accuracy of IHC for PD-L1 detection thus depends on the timing of a biopsy and is also related to previous therapies including radiation and chemotherapy. Studies have shown that tumor PD-L1 expression is upregulated after radiation treatment (Deng, et al. 2014)

Spatial factors need also be considered as PD-L1 expression may differ in primary tumors versus metastatic lesions. Even within one sample, different patterns of PD-L1 expression, focal and diffuse, can result in bias (Wang, et al. 2016). Also different locations on the same tumor are heterogeneous, and PD-L1 positive results are defined by membrane or cytoplasmic staining, when it has been shown that only positive membrane staining has biological significance (Wang, et al. 2016).

In addition, accurate scoring of PD-L1 protein expression by IHC is difficult due to other considerations such as data being retrospective, patients have different clinical characteristics, and comparing samples from different tumor types.

Immune therapy is starting to be used in treating HCC. Results of the phase II extended clinical trial testing nivolumab indicated an objective response rate of 16%, and median survival of 14 months among the 214 patients treated (El-Khoueiry, et al. 2015). However, in this trial, objective responses (21/145 cases, 15%) were not related to PD-L1 expression on tumor cells. Little is known about the immunological profile of HCC tumors and how to leverage this information to maximize response to immune-based therapies.

For these reasons and the fact that as shown above, PD-L1 expression is not a reliable biomarker for selecting ideal candidates for immunotherapy, there is a need for the identification of accurate predictive biomarkers for detecting patients with HCC who would benefit from immunotherapy.

SUMMARY OF THE INVENTION

The current invention solves the problem of using PD-L1 expression as a biomarker for detecting immunotherapy responsiveness by using a set of gene expression biomarkers that accurately detect a phenotype of immunotherapy responsiveness in patients with hepatocellular carcinoma (HCC).

The biomarkers described herein provide not only a novel and unique way to definitively identify, and predict a patient's response to immunotherapy, but also provide targets for use in drug screening and basic research on HCC as well as other cancers.

Using non-negative matrix factorization (NMF), the embodiments described herein, deconvolute the gene expression data of 956 human HCC samples and isolated the signal released from the inflammatory infiltrates to characterize the immunological landscape of HCC. This has allowed the identification an immune-specific class of HCC with specific biological traits, designated "Immune" class. Key features of this class include actual presence and activation of immune cells, enhanced cytolytic activity, and protein expression of PD-1 and PD-L1. Further evaluation of this class using the expression of 112 genes (FIG. 10A-D) found a gene signature profile indicative of response to immunotherapies. The gene expression profile of this Immune class was compared to a patient with HCC being treated with immunotherapy as well patients with other cancers who were responsive to HCC.

In these cases, the gene expression profile of the Immune class correlated with immunotherapy responsiveness.

The 112 gene panel was successfully reduced to 56 gene selecting those gene with the highest score. As indicated below, the 56-genes Immune classifier had a sensitivity of 97%, specificity of 98% and an accuracy of 97% (Table 3).

Thus, the use of the gene expression biomarkers provides for accurate detection of patients with HCC who will be responsive to immunotherapy.

Additionally, a subset of the 112 genes in FIGS. 10A-D, comprising 108 genes upregulated in the Immune class, is listed in FIGS. 11A-D.

Further dissection of the Immune class revealed two robust microenvironment-based types with either active immune activity or exhausted immune activity. These further classifications aid in determining therapy choices for patients with HCC as well as providing a comprehensive understanding of the immunological milieu of HCC. The exhausted immune activity class can be identified by the gene pathways in FIGS. 12A-G. These gene expression biomarkers are of particular relevance in identifying these subclasses as there was no significant difference in these two classes in terms of PD-L1 and PD-1 expression (Example 4).

Thus, one embodiment of the current invention is a method and/or assay for detecting a phenotype that is responsive to immunotherapy in a subject diagnosed with hepatocellular carcinoma comprising:

a. assaying gene expression levels of one or more genes in Table 3 in a sample from the subject with hepatocellular carcinoma to obtain a test expression profile;
b. comparing the test expression profile of the genes with a reference expression profile, wherein the reference expression profile comprises a reference expression level of the same genes in a sample from a control; and
c. detecting the gene expression levels of one or more genes in the test expression profile are the same as compared to expression level of the same genes in the reference expression profile that is indicative of immunotherapy responsive phenotype and further detecting that the subject would be responsive to immunotherapy.

A further embodiment of the present invention is a method of treating a subject with HCC, comprising:

a. assaying gene expression levels of one or more genes in Table 3 in a sample from the subject with hepatocellular carcinoma to obtain a test expression profile;
b. comparing the test expression profile of the genes with a reference expression profile, wherein the reference expression profile comprises a reference expression level of the same genes in a sample from a control;
c. detecting the gene expression levels of one or more genes in the test expression profile are the same as compared to expression level of the same genes in the reference expression profile that is indicative of immunotherapy responsive phenotype; and
d. treating the subject with immunotherapy.

In some embodiments, immunotherapy includes but is not limited to monoclonal antibodies directed against the cytotoxic T-lymphocyte protein (CTLA-4) (e.g., ipilimumab), the programmed cell death protein 1 (PD-1) (e.g., nivolumab and pembrolizumab) and its ligand PD-L1 (e.g., atezolizumab), and combinations thereof.

In some embodiments, the subject has been recently diagnosed with hepatocellular carcinoma (HCC). In some embodiments, the subject has been previously treated for HCC.

In some embodiments, the sample is tumor tissue. In some embodiments, multiple samples from the tumor are assayed for gene expression.

Determining the expression of any of the genes can be done by any method known in the art, including, but not limited to, microarrays; Southern blots; Northern blots; dot blots; primer extension; nuclease protection; subtractive hybridization and isolation of non-duplexed molecules using, for example, hydroxyapatite; solution hybridization; filter hybridization; amplification techniques such as RT-PCR and other PCR-related techniques such as PCR with melting curve analysis, and PCR with mass spectrometry; fingerprinting, such as with restriction endonucleases; and the use of structure specific endonucleases. mRNA expression can also be analyzed using mass spectrometry techniques (e.g., MALDI or SELDI), liquid chromatography, and capillary gel electrophoresis. Any additional method known in the art can be used to detect the presence or absence of the transcripts.

The expression of the genes from the subject with HCC can be compared to a reference level of the expression of the same genes in a control. The control can be a subject with HCC who has responded to immunotherapy. The control can be a subject who has responded to immunotherapy who has another form of cancer. The control can be a subject who has responded to immunotherapy who has lung cancer or melanoma. The levels of expressed genes may be measured as absolute or relative. Absolute quantitation measure concentrations of specific RNA and requires a calibration curve.

Relative quantification measures fold change differences of specific RNA in comparison to housekeeping genes. Relative quantification is usually adequate to investigate physiological changes in gene expression levels.

Either of these methods could be performed using one or more genes listed in FIGS. 10A-D and 11A-D.

The invention also provides methods for further detecting and identifying responsiveness to immunotherapy by the sub-classifications of the Immune class of Active Immune Response class or Exhausted Immune Response class. These sub-classifications are based upon the activation of the stroma. Those with lack of activated stroma are considered in the Active Immune Response class. Those with activated stroma are considered in the Exhausted Immune Response class. These classes while both part of the Immune class warrant slightly different treatment protocols.

Thus, a further embodiment of the present invention is a method of treating a subject with HCC, comprising
  a. assaying gene expression levels of one or more genes in Table 3 in a sample from the subject with hepatocellular carcinoma to obtain a first test expression profile;
  b. comparing the first test expression profile of the one or more genes in Table 3 with a first reference expression profile, wherein the first reference expression profile comprises a reference expression level of the same genes in a sample from a control;
  c. detecting the gene expression levels of one or more genes in the test expression profile are the same as compared to expression level of the same genes in the reference expression profile that is indicative of immunotherapy responsive phenotype and further detecting that the subject would be responsive to immunotherapy;
  d. assaying the gene expression levels of one or more genes in the pathways in FIGS. 12A-G in a sample from the subject with hepatocellular carcinoma to obtain a second test expression profile;
  e. comparing the second test expression profile of the one or more genes in the pathways in FIGS. 12A-G with a second reference expression profile, wherein the second expression profile comprises a reference expression level of the same genes in a sample from a control;
  f. detecting the gene expression levels of one or more genes in the second test expression profile are the same as compared to expression level of the same genes in the second reference expression profile that is indicative of Exhausted Immune Response phenotype; and
  g. treating the subject with a combination of immunotherapy and a second agent.

In some embodiments, the subject has been recently diagnosed with hepatocellular carcinoma (HCC). In some embodiments, the subject has been previously treated for HCC.

In some embodiments, the sample is tumor tissue. In some embodiments, multiple samples from the tumor are assayed for gene expression.

Determining the expression of any of the genes can be done by any method known in the art, including, but not limited to, microarrays; Southern blots; Northern blots; dot blots; primer extension; nuclease protection; subtractive hybridization and isolation of non-duplexed molecules using, for example, hydroxyapatite; solution hybridization; filter hybridization; amplification techniques such as RT-PCR and other PCR-related techniques such as PCR with melting curve analysis, and PCR with mass spectrometry; fingerprinting, such as with restriction endonucleases; and the use of structure specific endonucleases. mRNA expression can also be analyzed using mass spectrometry techniques (e.g., MALDI or SELDI), liquid chromatography, and capillary gel electrophoresis. Any additional method known in the art can be used to detect the presence or absence of the transcripts.

The expression of the genes from the subject with HCC can be compared to a reference level of the expression of the same genes in a control. The control can be the same for both step (b) and step (e) or the controls can be different. The control can be a subject with HCC who has responded to immunotherapy. The control can be a subject who has responded to immunotherapy who has another form of cancer. The control can be a subject who has responded to immunotherapy who has lung cancer or melanoma. The levels of expressed genes may be measured as absolute or relative. Absolute quantitation measure concentrations of specific RNA and requires a calibration curve. Relative quantification measures fold change differences of specific RNA in comparison to housekeeping genes. Relative quantification is usually adequate to investigate physiological changes in gene expression levels.

Steps a-c can be performed using one or more of the genes listed in FIGS. 10A-D and 11A-D.

In some embodiments, immunotherapy includes but is not limited to monoclonal antibodies directed against the cytotoxic T-lymphocyte protein (CTLA-4) (e.g., ipilimumab), the programmed cell death protein 1 (PD-1) (e.g., nivolumab and pembrolizumab) and its ligand PD-L1 (e.g., atezolizumab), and combinations thereof.

In some embodiments, the gene of which the expression level is assayed in step (d) is PMEPA1, LGALS1, LGALS3, TGF-β or from the CTNNB1 signaling pathway including CXCL12 and CCL2.

In some embodiments, the second agent includes but is not limited to a TGF-β inhibitor and a CTNNB1 signaling pathway inhibitor. In some embodiments, the second agent is a chemotherapeutic agent or radiation.

A further embodiment of the present invention is a method of treating a subject with HCC, comprising
  a. assaying gene expression levels of one or more genes in Table 3 in a sample from the subject with hepatocellular carcinoma to obtain a first test expression profile;
  b. comparing the first test expression profile of the one or more genes in Table 3 with a first reference expression profile, wherein the first reference expression profile comprises a reference expression level of the same genes in a sample from a control;
  c. detecting the gene expression levels of one or more genes in the test expression profile are the same as compared to expression level of the same genes in the reference expression profile that is indicative of immunotherapy responsive phenotype and further detecting that the subject would be responsive to immunotherapy;
  d. assaying the gene expression levels of one or more genes chosen from the group consisting of PMEPA1, LGALS1, LGALS3, TGF-β, genes from the CTNNB1 signaling pathway and combinations thereof in a sample from the subject with hepatocellular carcinoma to obtain a second test expression profile;
  e. comparing the second test expression profile of the one or more genes chosen from the group consisting of PMEPA1, LGALS1, LGALS3, TGF-β, genes from the CTNNB1 signaling pathway and combinations thereof with a second reference expression profile, wherein the second expression profile comprises a reference expression level of the same genes in a sample from a control;

f. detecting the gene expression levels of one or more genes in the second test expression profile are the same as compared to expression level of the same genes in the second reference expression profile that is indicative of Exhausted Immune Response phenotype; and g. treating the subject with a combination of immunotherapy and a second agent.

In some embodiments, the genes from the CTNNB1 signaling pathway are CXCL12 and CCL2.

The invention also provides for kits.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

FIG. 2 shows a table of publicly available gene signatures used in the study in order of appearance in the text.

FIG. 3B shows representative images of immune cell infiltration, PD-1 and PD-L1 staining in a patient of the Immune class (M321) and a patient outside of the Immune class (M743). Images were captured with 20×. FIG. 3C is a graph showing tertiary lymphoid structures (TLS) count in patients of the Immune class compared to the rest of the cohort. Vertical axis is TLS count is indicated as a continuum variable and horizontal axis, patients within (right) versus those outside the Immune class (left).

FIG. 5 shows Kaplan-Meier estimates of overall survival and recurrence rate according to the immune response type status and robustness of the Immune class. FIG. 5A shows Kaplan-Meier estimates of overall survival according to the Active Immune Response status in the Heptromic cohort (Active Immune Response vs rest plus Exhausted Immune Response). FIG. 5B shows Kaplan-Meier estimates of overall survival according to the Active Immune Response status 1 in the TCGA cohort.

FIG. 6 shows the association of the Immune class with copy number aberrations, presence of neo-antigens, mutations in driver genes, and alterations in methylation. FIG. 6A shows the burden of gains in patients of the Immune class versus the rest of the cohort. FIG. 6B shows the burden of losses in patients of the Immune class versus the rest of the cohort. In both FIGURES, both broad (left panels) and focal (right panels) are shown. FIG. 6I is a graph of LGALS3 expression in the Immune Response Subtypes and the rest of the cohort (left) and PMEPA1 expression (right).

FIG. 8 shows anti-tumor activity of nivolumab in patient #1 positively predicted by the immune classifier. Initially, patient #1 presented with intrahepatic recurrence and a metastatic pelvis mass of 16 cm after resection for single 3 cm HCC. FIG. 8A shows CT images of patient #1 before start of treatment with nivolumab. FIG. 8B shows CT images of patient #1 showing 75% reduction in tumor mass after 2 months of treatment with nivolumab. The white arrows point to the tumor in each image.

FIG. 9 shows the genetic similarity between patients of the Immune class and melanoma patients responsive to PD-1 therapy. FIG. 9A is submap analysis for Heptromic as applied considering 2 groups in HCC cohorts (Immune class vs rest) and 4 groups [pre-PD1 responders (pre-PD1 R) and non-responders (pre-PD1 NR); pre-CTLA4 responders (pre-CTLA4 R) and non-responders (pre-CTLA-4 NR)] in Chen et al. dataset. FIG. 9B is a submap analysis for Heptromic as applied considering 3 groups in HCC cohorts (Active Immune, Exhausted Immune and rest) and 4 groups [pre-PD1 responders (pre-PD1 R) and non-responders (pre-PD1 NR); pre-CTLA4 responders (pre-CTLA4 R) and non-responders (pre-CTLA-4 NR)] in Chen et al. dataset. FIG. 9C is submap analysis for TCGA as applied considering 2 groups in HCC cohorts (Immune class vs rest) and 4 groups [pre-PD1 responders (pre-PD1 R) and non-responders (pre-PD1 NR); pre-CTLA4 responders (pre-CTLA4 R) and non-responders (pre-CTLA-4 NR)] in Chen et al. dataset. FIG. 9D is a submap analysis for TCGA as applied considering 3 groups in HCC cohorts (Active Immune, Exhausted Immune and rest) and 4 groups [pre-PD1 responders (pre-PD1 R) and non-responders (pre-PD1 NR); pre-CTLA4 responders (pre-CTLA4 R) and non-responders (pre-CTLA-4 NR)] in Chen et al. dataset. Similarity was observed between the Immune class and anti-PD1 responders (p=0.01 in Heptromic and non-significant trend in TCGA) and between the Active Immune subtype and anti-PD1 responders in both cohorts (Bonferroni-corrected p-value=0.01).

FIGS. 10A-10D is a table of the genes in the Immune subclass gene classifier.

FIGS. 11A-11D is a table of genes significantly overexpressed in the Immune class.

FIGS. 12A-12G is a table of enriched gene pathways in the Exhausted Immune Response subtype.

FIG. 13 is a table of the distribution of focal high-level amplifications (HLA) and homozygous deletions in driver genes between the Immune class and the rest of patients.

FIG. 14 shows the heatmap visualization of the predictive capacity of the 56-genes Immune classifier compared to the original 112-genes Immune classifier. In the heatmap each column represents a sample whereas each row represents the 112-genes classifier or the 56-genes Immune classifier (bottom row). Samples positively predicted to belong to the Immune class are represented as dark boxes to the left whereas patients predictive to be negative for the Immune classifier are represented as light boxes to the right. FIG. 14A shows the results for the TGCA dataset (n=190 samples). FIG. 14B shows the results for the Validation cohort (n=132). FIG. 14C shows the results for the HCC-I dataset (n=90).

DETAILED DESCRIPTION OF THE INVENTION

Definitions

Figure 1:
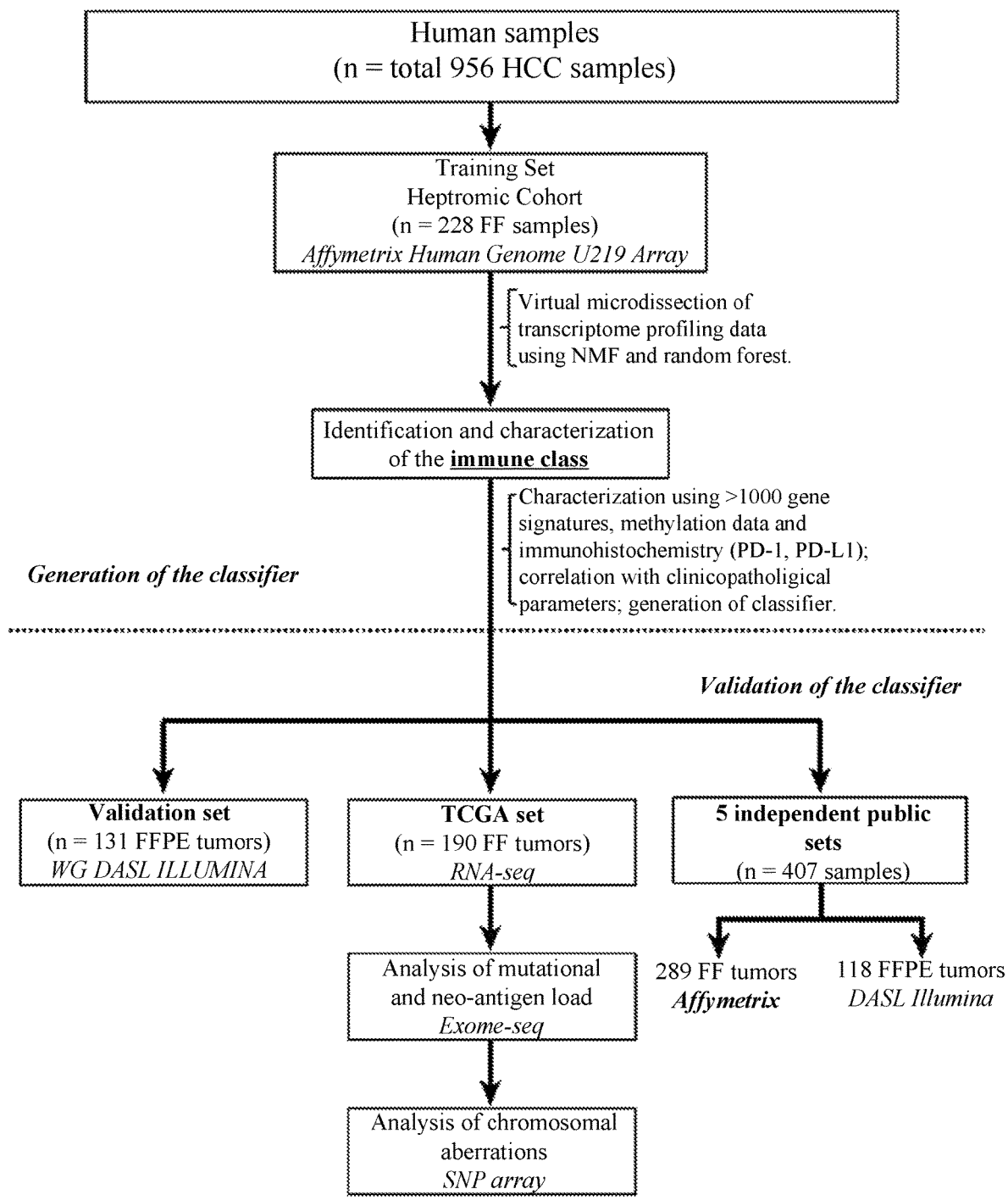
FIG. 1 depicts a flowchart of the study. A total of 956 HCC samples were used in this study. A training cohort (Heptromic) including 228 HCCs was virtually microdissected to identify an Immune class. Validation was then performed in 7 independent data sets.

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them.

Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

As used herein, the term "Hepatocellular carcinoma (HCC)" means a primary malignancy of the liver and occurs predominantly in patients with underlying chronic liver disease and cirrhosis. The cell(s) of origin are believed to be the hepatic stem cells, although this remains the subject of investigation. Tumors progress with local expansion, intrahepatic spread, and distant metastases.

As used herein, the term "subject" or "patient" as used herein refers to a mammal, preferably a human, for whom treatment can be provided.

The term "treatment" or "treating" as used herein refers to the administration of medicine or the performance of medical procedures with respect to a subject, for either prophylaxis (prevention) or to cure or reduce the extent of or likelihood of occurrence or recurrence of the infirmity or malady or condition or event in the instance where the subject or patient is afflicted. As related to the present disclosure, the term may also mean the administration of pharmacological substances or formulations, or the performance of non-pharmacological methods including, but not limited to, radiation therapy and surgery. Pharmacological substances as used herein may include, but are not limited to, chemotherapeutics that are established in the art, such as Gemcitabine (GEMZAR), 5-fluorouracil (5-FU), irinotecan (CAMPTOSAR), oxaliplatin (ELOXATIN), albumin-bound paclitaxel (ABRAXANE), capecitabine (XELODA), cisplatin, paclitaxel (TAXOL), docetaxel (TAXOTERE), and irinotecan liposome (ONIVYDE). Pharmacological substances may include substances used in immunotherapy, such as checkpoint inhibitors, may include, but are not limited to, ipilimumab, nivolumab, pembrolizumab, and atezolimumab. Treatment may include a multiplicity of pharmacological substances as well as radiation therapy and surgery.

The term "agent" as used herein means a substance that produces or is capable of producing an effect and would include, but is not limited to, chemicals, pharmaceuticals, biologics, small organic molecules, antibodies, nucleic acids, peptides, and proteins.

The phrase "therapeutically effective amount" is used herein to mean an amount sufficient to cause an improvement in a clinically significant condition in the subject, or delays or minimizes or mitigates one or more symptoms associated with the disease, or results in a desired beneficial change of physiology in the subject.

The terms "expression profile" or "gene expression profile" refers to any description or measurement of one or more of the genes that are expressed by a cell, tissue, or organism under or in response to a particular condition. Expression profiles can identify genes that are up-regulated, down-regulated, or unaffected under particular conditions. Gene expression can be detected at the nucleic acid level or at the protein level. The expression profiling at the nucleic acid level can be accomplished using any available technology to measure gene transcript levels. For example, the method could employ in situ hybridization, Northern hybridization or hybridization to a nucleic acid microarray, such as an oligonucleotide microarray, or a cDNA microarray. Alternatively, the method could employ reverse transcriptase-polymerase chain reaction (RT-PCR) such as fluorescent dye-based quantitative real time PCR (TaqMan® PCR). The expression profiling at the protein level can be accomplished using any available technology to measure protein levels, e.g., using peptide-specific capture agent arrays.

The terms "gene", "gene transcript", and "transcript" are used somewhat interchangeable in the application. The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. "Transcript" or "gene transcript" is a sequence of RNA produced by transcription of a particular gene. Thus, the expression of the gene can be measured via the transcript.

As used herein, the term "Immune class" refers patients having hepatocellular carcinoma showing significant enrichment of signatures identifying immune cells, i.e., T cells, cytotox tertiary lymphoid structures (TLS), and macrophages, immune metagenes, IFN gene signatures predictive of response to pembrolizumab in melanoma, and head and neck squamous cell carcinoma, and PD-1 signaling.

As used herein, the term "IFN" refers to interferon.

As used herein, the term "CTNNB1" refers to Catenin Beta 1.

As used herein, the term "NMF" refers to non-negative matrix factorization.

As used herein, the term "TLS" refers to tertiary lymphoid structure.

As used herein, the term "FDR" refers to false discovery rate.

As used herein, the term "CCL" refers to Chemokine (C-C motif) ligand.

As used herein, the term "CXCL" refers to chemokine (C—X—C motif) ligand.

As used herein, the term "JAK/STAT" refers to Janus Kinase/Signal Transducer and Activator of Transcription.

As used herein, the term "GSEA" refers to gene set enrichment analysis.

As used herein, the term "EMT" refers to epithelial mesenchymal transition.

As used herein, the term "NTP" refers to nearest template prediction.

As used herein, the term "TBRS" refers to TGF-beta response signature.

As used herein, the term "F-TBRS" refers to Fibroblasts-derived TGF-beta response signature.

As used herein, the term "T-TBRS" refers to T cells-derived TGF-beta response signature.

As used herein, the term "LGALS" refers to lectin, galactose binding, soluble 1. As used herein, the term "NKG2D" refers to natural killer group 2D.

As used herein, the term "TBX" refers to 1 T-box transcription factor.

As used herein, the term "FFPE" refers to formalin fixed paraffin embedded.

As used herein, the term "PMEPA1" refers to prostate transmembrane protein, androgen induced 1.

As used herein, the term "PTK2" refers to Protein Tyrosine Kinase 2.

As used herein, the term "AFP" refers to Alpha Fetoprotein.

As used herein, the term "RF" refers to random forest.

As used herein, the term "SCNA" refers to somatic copy number aberrations.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Molecular Biology

In accordance with the present invention, there may be numerous tools and techniques within the skill of the art, such as those commonly used in molecular immunology, cellular immunology, pharmacology, and microbiology. See, e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

Identification of an Immune Class of HCC and Sub-Classes, Active Immune Response and Exhausted Immune Response The current invention solves the problem of using PD-L1 expression as a biomarker for detecting immunotherapy responsiveness by using a set of gene expression biomarkers that accurately detect a phenotype of immunotherapy responsiveness in patients with HCC.

The biomarkers described herein provide not only a novel and unique way to definitively identify, detect, and predict a patient's response to immunotherapy, but also provide a number of markers for use in drug screening and basic research on HCC as well as other cancers.

Using non-negative matrix factorization (NMF), the embodiments described herein, the gene expression data of 956 human HCC samples were deconvoluted and isolated the signal released from the inflammatory infiltrates to characterize the immunological landscape of HCC. This has allowed the identification of a previously unnoticed robust, immune-specific class of HCC with specific biological traits, designated "Immune" class. Close to 25% of HCCs belong to the Immune class, whose molecular characteristics— including high infiltration of immune cells, expression of PD-1 and PD-L1, and active IFN-γ signaling—highly resemble those of cancers most responsive to immunotherapy (Ji, et al. 2012; Le, et al. 2015; Bald, et al. 2014). Further evaluation of this class using the expression of 112 genes (FIGS. 10-D) found a gene signature profile indicative of response to immunotherapies (Examples 2 and 5). The gene expression profile of this Immune class was compared to patients with HCC being treated with immunotherapy as well patients with other cancers who were responsive to HCC. In these cases, the gene expression profile of the Immune class correlated with immunotherapy responsiveness (Example 5; FIGS. 8 and 9).

Figure 15:
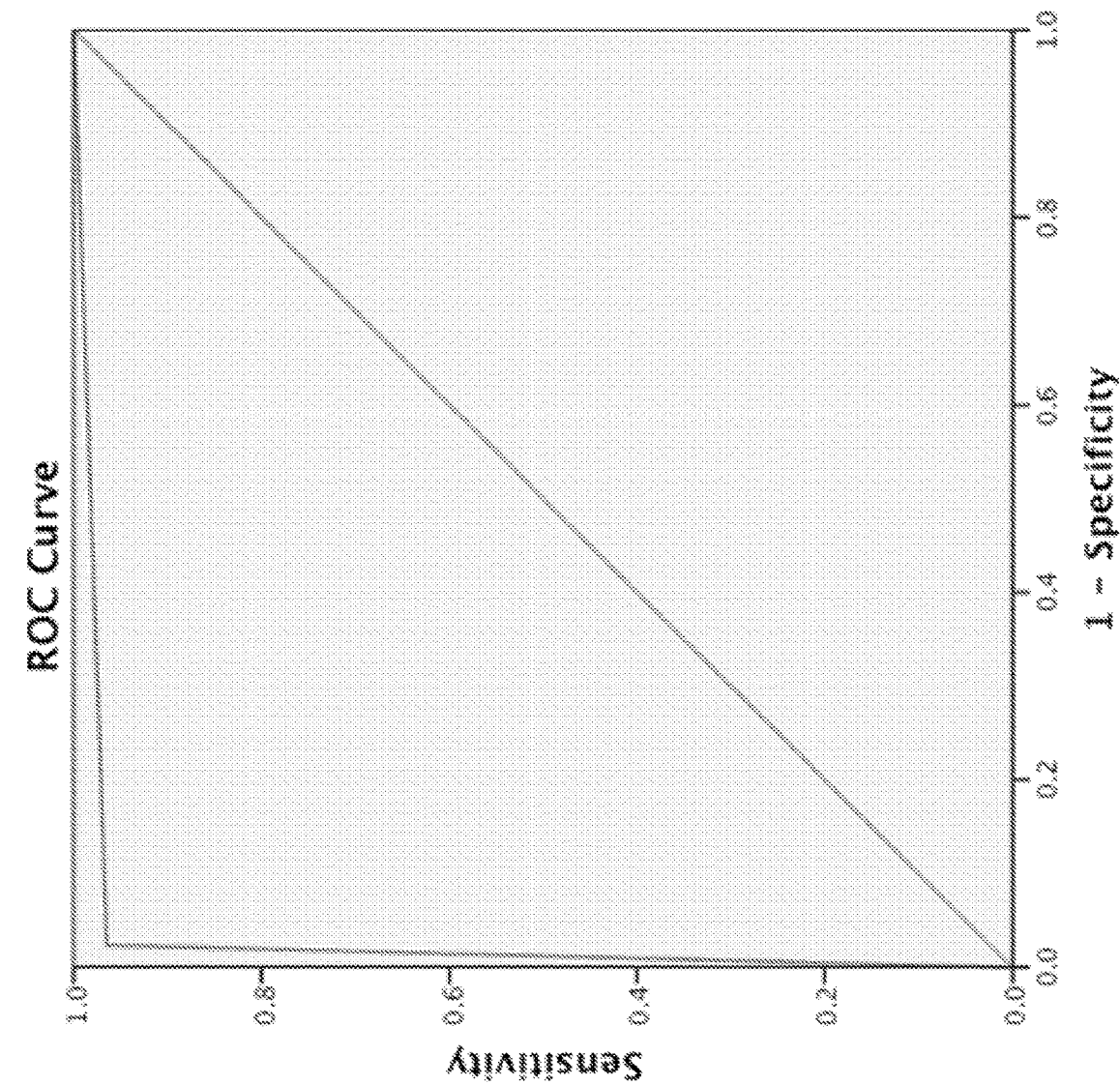
FIG. 15 is a Receiver Operating Characteristic (ROC) curve calculated in all patients analyzed (n=441). Standard error=0.011, confidence interval (0.949-0.993), Asymptotic significance=0.011.

The original 112-genes Immune classifier was successfully reduced to 56 genes selecting those genes with highest score (Table 3). The prediction capacity of the 56-genes Immune classifier has been tested and compared to the 112-genes original immune classifier in 3 datasets: TGCA, Validation cohort and HCC-I dataset. The 56-genes Immune classifier had a sensitivity of 97%, specificity of 98%, and an accuracy of 97% (Example 10; FIGS. 14 and 15). Thus, the use of the gene expression biomarkers provides for accurate detection of patients with HCC who will be responsive to immunotherapy.

PD-L1 staining was enriched in the Immune class, but failed to capture most of the cases, and thus represents a suboptimal marker (Example 3). As discussed above, this finding is consistent with the lack of predictive capacity observed for PD-L1 expression on tumor cells in the large phase II study with nivolumab for HCC patients (El-Khoueiry, et al. 2017), and shows the need for other biomarkers for the detection of those HCC patients who would benefit from immunotherapy.

While this immune phenotype of the Immune class can predict response to immunotherapies, since a favorable response to checkpoint inhibitors relies on the intricate and dynamic interactions between tumor cells, immune cells and other immunomodulators present in the microenvironment, which may either dampen or enhance the immune response, further analysis was performed. In this regard, virtual dissection of the gene expression profile of the Immune class allowed the elucidation of such interactions and identified two clear cut microenvironment-based clusters of samples: 1) Active Immune Response and 2) Exhausted Immune Response. Robustness of these subtypes was supported by their successful replication in seven independent datasets across different platforms, ranging from RNA-sequencing to microarray and using distinct types of samples (i.e., fresh frozen and paraffin-embedded tissue). While the Active Immune Response cluster showed anti-tumor immune features such as enrichment of IFN signatures, overexpression of adaptive immune response genes and better survival, the Exhausted Immune Response was characterized by tumor-promoting signals (e.g., activated stroma, T cell exhaustion and immunosuppressive components) (FIGS. 12A-G). In particular, activation of TGF-β, a potent immunoregulatory cytokine frequently overexpressed in aggressive cancers, was significantly enriched in the Exhausted Subtype. TGF-β regulates tumor-stroma interactions, angiogenesis, metastasis, and suppresses the host immune response via induction of T cell exhaustion (Park, et al. 2016; Stephen, et al. 2014) and promotion of M2-type macrophages (Flavell, et al. 2010) (Example 4).

Understanding the interactions between the immune response, oncogenic signaling and the tumor microenvironment is critical to improve the efficacy of current immunotherapies. For example, patients within the Exhausted Immune Response subtype could benefit from the combination of TGF-β inhibition plus immune checkpoint blockade. In this regard, a phase 1b/2 clinical trial testing the novel TGF-β inhibitor, galunisertib, in combination with nivolumab in advanced solid tumors, including HCC, is currently ongoing (NCT02423343), with no patient enrichment strategy. Similarly, dissection of the oncogenic mechanisms responsible for T cell exclusion could bring additional combination strategies in patients who otherwise would likely not respond. Recent molecular analyses have revealed a correlation between activation of the CTNNB1 signaling pathway and lower T cell infiltrates in melanoma and other tumors (Porta-Pardo and Godzik 2016). Consistent with these findings, HCC samples within the CTNNB1 class showed lower immune-cell signature scores. Interestingly, the CTNNB1 class also displayed over-expression of PTK2, another oncogenic signal recently reported to drive immune exclusion (Jiang, et al. 2016).

Genes Correlated to the Immune Class Predictive of Response to Immunotherapy

As fully discussed, the current biomarker for response to immunotherapy, expression of PD-L1, is not reliable and there is a need in the art for reliable biomarkers. The data herein show for the first time, biomarkers in the form of a set of genes, which correlate to a positive response to immunotherapy.

These biomarkers include 112 genes that are differentially expressed in the Immune class. These genes are listed in FIGS. 10A-D.

A set of 56 genes has been shown to be more sensitive and accurate in correlating a positive response to immunotherapy. These genes are listed in Table 3.

Additionally, the 108 genes listed in FIGS. 11A-D are upregulated in the Immune class.

By using these biomarkers, important predictions and determinations can be made regarding an HCC patient's response to immunotherapy. While tests for these biomarkers can be performed at any time after a diagnosis of HCC, preferably such tests would be performed as soon as possible after a positive diagnosis of HCC is made by a clinician. In that manner, the valuable insight into the disease can be utilized in choice of therapy.

Thus, one embodiment of the present invention, a test for the expression of one or more genes in FIGS. 10A-D could be done and a positive result would indicate that the subject is a candidate for immunotherapy.

A further embodiment of the present invention, a test for the expression of one or more genes in FIGS. 11A-D could be done and a positive result would indicate that the subject is a candidate for immunotherapy.

A further embodiment of the present invention, a test for the expression of one or more genes in Table 3 could be done and a positive result would indicate that the subject is a candidate for immunotherapy.

As also fully discussed, the data herein also show two distinct sub-classes that also predict the response to treatment by a patient with HCC. These sub-classes, termed Active Immune Response and Exhausted Immune Response can also be identified by the expression of a set of gene pathways found in FIGS. 12A-G.

Thus, in a further embodiment of the invention, a test for the expression of one or more genes in the pathways listed in FIGS. 12A-G can be done and a positive result would indicate that the patient while a candidate for immunotherapy, the immunotherapy should be combined with another agent, such as a TGF-β inhibitor.

In order to detect any of these transcripts or genes, a sample of tumor from a subject who has been positively diagnosed with HCC is obtained and prepared and analyzed for the presence of the biomarkers, i.e, gene expression, in Table 3, FIGS. 10A-D, 11A-D, and/or 12A-G. This can be achieved in numerous ways, by a diagnostic laboratory, and/or a health care provider.

Alternatively, nucleic acid can be obtained from any biological tissue including but not limited to liver, whole blood, and plasma, and from any biological fluid including, but not limited to, plasma.

The nucleic acid is extracted, isolated and purified from the cells of the tumor, tissue or fluid by methods known in the art.

If required, a nucleic acid sample having the gene sequence(s) are prepared using known techniques. For example, the sample can be treated to lyse the cells, using known lysis buffers, sonication, electroporation, with purification and amplification occurring as needed, as will be understood by those in the skilled in the art. In addition, the reactions can be accomplished in a variety of ways. Components of the reaction may be added simultaneously, or sequentially, in any order. In addition, the reaction can include a variety of other reagents which can be useful in the methods and assays and would include but is not limited to salts, buffers, neutral proteins, such albumin, and detergents, which may be used to facilitate optimal hybridization and detection, and/or reduce non-specific or background interactions. Also reagents that otherwise improve the efficiency of the assay, such as protease inhibitors, nuclease inhibitors, and anti-microbial agents, can be used, depending on the sample preparation methods and purity.

Once prepared, mRNA or other nucleic acids are analyzed by methods known to those of skill in the art. In addition, when nucleic acids are to be detected preferred methods utilize cutting or shearing techniques to cut the nucleic acid sample containing the target sequence into a size that will facilitate handling and hybridization to the target. This can be accomplished by shearing the nucleic acid through mechanical forces, such as sonication, or by cleaving the nucleic acid using restriction endonucleases, or any other methods known in the art. However, in most cases, the natural degradation that occurs during archiving results in "short" oligonucleotides. In general, the methods and assays of the invention can be done on oligonucleotides as short as 20-100 base pairs, with from 20 to 50 being preferred, and between 40 and 50, including 44, 45, 46, 47, 48 and 49 being the most preferred.

Methods for examining gene expression, are often hybridization based, and include, Southern blots; Northern blots; dot blots; primer extension; nuclease protection; subtractive hybridization and isolation of non-duplexed molecules using, for example, hydroxyapatite; solution hybridization; filter hybridization; amplification techniques such as RT-PCR and other PCR-related techniques such as PCR with melting curve analysis, and PCR with mass spectrometry; fingerprinting, such as with restriction endonucleases; and the use of structure specific endonucleases. mRNA expression can also be analyzed using mass spectrometry techniques (e.g., MALDI or SELDI), liquid chromatography, and capillary gel electrophoresis. Any additional method known in the art can be used to detect the presence or absence of the transcripts.

For a general description of these techniques, see also Sambrook et al. 1989; Kriegler 1990; and Ausebel et al. 1990.

A preferred method for the detection of gene expression is the use of arrays or microarrays. These terms are used interchangeably and refer to any ordered arrangement on a surface or substrate of different molecules, referred to herein as "probes." Each different probe of any array is capable of specifically recognizing and/or binding to a particular molecule, which is referred to herein as its "target" in the context of arrays. Examples of typical target molecules that can be detected using microarrays include mRNA transcripts, cRNA molecules, cDNA, PCR products, and proteins.

Microarrays are useful for simultaneously detecting the presence, absence and quantity of a plurality of different target molecules in a sample. The presence and quantity, or absence, of the probe's target molecule in a sample may be readily determined by analyzing whether and how much of a target has bound to a probe at a particular location on the surface or substrate.

In a preferred embodiment, arrays used in the present invention are "addressable arrays" where each different probe is associated with a particular "address."

The arrays used in the present invention are preferable nucleic acid arrays that comprise a plurality of nucleic acid probes immobilized on a surface or substrate. The different nucleic acid probes are complementary to, and therefore can hybridize to, different target nucleic acid molecules in a sample. Thus, each probe can be used to simultaneously detect the presence and quantity of a plurality of different genes, e.g., the presence and abundance of different mRNA molecules, or of nucleic acid molecules derived therefrom (for example, cDNA or cRNA).

The arrays are preferably reproducible, allowing multiple copies of a given array to be produced and the results from each easily compared to one another. Preferably microarrays are small, and made from materials that are stable under binding conditions. A given binding site or unique set of binding sites in the microarray will specifically bind to the target. It will be appreciated that when cDNA complementary to the RNA of a cell is made and hybridized to a microarray under suitable conditions, the level or degree of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding a nucleic acid product of the gene) that is not transcribed in the cell will have little or no signal, while a gene for which mRNA is highly prevalent will have a relatively strong signal.

By way of example, GeneChip® (Affymetrix, Santa Clara, Calif.), generates data for the assessment of gene expression profiles and other biological assays. Oligonucleotide expression arrays simultaneously and quantitatively "interrogate" thousands of mRNA transcripts. Each transcript can be represented on a probe array by multiple probe pairs to differentiate among closely related members of gene families. Each probe contains millions of copies of a specific oligonucleotide probe, permitting the accurate and sensitive detection of even low-intensity mRNA hybridization patterns. After hybridization data is captured, using a scanner or optical detection systems, software can be used to automatically calculate the intensity values for each probe cell. Probe cell intensities can be used to calculate an average intensity for each gene, which correlates with mRNA abundance levels. Expression data can be quickly sorted based on any analysis parameter and displayed in a variety of graphical formats for any selected subset of genes.

Further examples of microarrays that can be used in the assays and methods of the invention are microarrays synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752 and 6,482,591.

Other exemplary arrays that are useful for use in the invention include, but are not limited to, Sentrix® Array or Sentrix® BeadChip Array available from Illumina®, Inc. (San Diego, Calif.) or others including beads in wells such as those described in U.S. Pat. Nos. 6,266,459; 6,355,431; 6,770,441; and 6,859,570. Arrays that have particle on the surface can also be used and include those described in U.S. Pat. Nos. 6,489,606; 7,106,513; 7,126,755; and 7,164,533.

An array of beads in a fluid format, such as a fluid stream of a flow cytometer or similar device, can also be used in methods for the invention. Exemplary formats that can be used in the invention to distinguish beads in a fluid sample using microfluidic devices are described, for example, in U.S. Pat. No. 6,524,793. Commercially available fluid formats for distinguishing beads include, for example, those used in XMAP™ technologies from Luminex or MPSS™ methods from Lynx Therapeutics.

A spotted microarray can also be used in a method of the invention. An exemplary spotted microarray is a CodeLink™ Array available from Amersham Biosciences.

Another microarray that is useful in the invention is one that is manufactured using inkjet printing methods such as SurePrint™ Technology available from Agilent Technologies. Other microarrays that can be used in the invention include, without limitation, those described in U.S. Pat. Nos. 5,429,807; 5,436,327; 5,561,071; 5,583,211; 5,658,734; 5,837,858; 5,919,523; 6,287,768; 6,287,776; 6,288,220; 6,297,006; 6,291,193; and 6,514,751.

Screening and diagnostic method of the current invention may involve the amplification of the target loci. A preferred method for target amplification of nucleic acid sequences is using polymerases, in particular polymerase chain reaction (PCR). PCR or other polymerase-driven amplification methods obtain millions of copies of the relevant nucleic acid sequences which then can be used as substrates for probes or sequenced or used in other assays.

Amplification using polymerase chain reaction is particularly useful in the embodiments of the current invention. PCR is a rapid and versatile in vitro method for amplifying defined target DNA sequences present within a source of DNA. Usually, the method is designed to permit selective amplification of a specific target DNA sequence(s) within a heterogeneous collection of DNA sequences (e.g. total genomic DNA or a complex cDNA population). To permit such selective amplification, some prior DNA sequence information from the target sequences is required. This information is used to design two oligonucleotide primers (amplimers) which are specific for the target sequence and which are often about 15-25 nucleotides long.

Treatment with Immune Checkpoint Inhibitors

Immune checkpoints regulate T cell function in the immune system. T cells play a central role in cell-mediated immunity. Checkpoint proteins interact with specific ligands which send a signal to the T cell and essentially turn off or inhibit T cell function. Cancer cells take advantage of this system by driving high levels of expression of checkpoint proteins on their surface which results in control of the T cells expressing checkpoint proteins on the surface of T cells that enter the tumor microenvironment, thus suppressing the anticancer immune response. As such, inhibition of checkpoint proteins results in complete or partial restoration of T cell function and an immune response to the cancer cells. Examples of checkpoint proteins include, but are not limited to CTLA-4, PD-L1, PD-L2, PD-1, B7-H3, B7-H4, BTLA, HVEM, TIM3, GAL9, LAG3, VISTA, KIR, 2B4 (belongs to the CD2 family of molecules and is expressed on all NK, $\gamma\delta$, and memory CD8+($\alpha\beta$) T cells), CD 160 (also referred to as BY55), CGEN-15049, CHK 1 and CHK2 kinases, A2aR and various B-7 family ligands.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PD-L1, PD-L2, PD-1, B7-H3, B7-H4, BTLA, HVEM, GAL9, LAG3, TIM3, VISTA, KIR, 2B4 (belongs to the CD2 family of molecules and is expressed on all NK, $\gamma\delta$, and memory CD8+ ($\alpha\beta$) T cells), CD160 (also referred to as BY55), CGEN-15049, CHK 1 and CHK2 kinases, A2aR and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics or small molecules, that bind to and block or inhibit the activity of one or more of CTLA-4, PD-L1, PD-L2, PD-1, BTLA, HVEM, TIM3, GALS, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor).

Checkpoint protein ligands include, but are not limited to PD-L1, PD-L2, B7-H3, B7-H4, CD28, CD86 and TIM-3.

Programmed cell death protein 1 (PD-1) is a 288 amino acid cell surface protein molecule expressed on T cells and pro-B cells and plays a role in their fate/differentiation. PD-1 has two ligands, PD-L1 and PD-L2, which are members of the B7 family. PD-1 plays a role in tumor-specific escape from immune surveillance. PD-1 is up-regulated in melanoma infiltrating T lymphocytes (TILs) (Dotti (2009) Blood 114 (8): 1457-58). Tumors have been found to express the PD-1 ligand (PDL-1 and PDL-2) which, when combined with the up-regulation of PD-1 in CTLs, may be a contributory factor in the loss in T cell functionality and the inability of CTLs to mediate an effective anti-tumor response.

Clinical trials in melanoma have shown robust anti-tumor responses with anti-PD-1 blockade. Significant benefit with PD-1 inhibition in cases of advanced melanoma, ovarian cancer, non-small-cell lung, prostate, renal-cell, and colorectal cancer have also been described. Studies in murine models have applied this evidence to glioma therapy. Anti-PD-1 blockade adjuvant to radiation promoted cytotoxic T cell population and an associated long-term survival benefit in mice with glioma tumor.

One aspect of the present disclosure provides checkpoint inhibitors which are antibodies that can act as inhibitors of PD-1, thereby modulating immune responses regulated by PD-1. In one embodiment, the anti-PD-1 antibodies can be antigen-binding fragments. Anti-PD-1 antibodies disclosed herein are able to bind to human PD-1 and agonize the activity of PD-1, thereby inhibiting the function of immune cells expressing PD-1. Examples of PD-1 and PD-L1 blockers are described in U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699.

There are several PD-1 inhibitors currently being tested in clinical trials. CT-011 is a humanized IgG1 monoclonal antibody against PD-1. A phase II clinical trial in subjects with diffuse large B-cell lymphoma (DLBCL) who have undergone autologous stem cell transplantation was recently completed. Preliminary results demonstrated that 70% of subjects were progression-free at the end of the follow-up period, compared with 47% in the control group, and 82% of subjects were alive, compared with 62% in the control group. This trial determined that CT-011 not only blocks PD-1 function, but it also augments the activity of natural killer cells, thus intensifying the antitumor immune response.

BMS 936558 is a fully human IgG4 monoclonal antibody targeting PD-1. In a phase I trial, biweekly administration of BMS-936558 in subjects with advanced, treatment-refractory malignancies showed durable partial or complete regressions. The most significant response rate was observed in subjects with melanoma (28%) and renal cell carcinoma (27%), but substantial clinical activity was also observed in subjects with non-small cell lung cancer (NSCLC), and some responses persisted for more than a year.

BMS 936559 is a fully human IgG4 monoclonal antibody that targets the PD-1 ligand PD-L1. Phase I results showed that biweekly administration of this drug led to durable responses, especially in subjects with melanoma. Objective response rates ranged from 6% to 17%) depending on the cancer type in subjects with advanced-stage NSCLC, melanoma, RCC, or ovarian cancer, with some subjects experiencing responses lasting a year or longer.

MK 3475 is a humanized IgG4 anti-PD-1 monoclonal antibody in Phase III study alone or in combination with chemotherapy versus chemotherapy alone as first-line therapy for advanced gastric or gastroesophageal junction (GEJ) adenocarcinoma. MK 3475 is currently undergoing numerous global Phase III clinical trials.

MPDL 3280A (atezolizumab) is a monoclonal antibody, which also targets PD-L1. MPDL 3280A received Breakthrough Therapy Designation from the U.S. Food and Drug Administration (FDA) for the treatment of people whose NSCLC expresses PD-L1 and who progressed during or after standard treatments.

AMP 224 is a fusion protein of the extracellular domain of the second PD-1 ligand, PD-L2, and IgG1, which has the potential to block the PD-L2/PD-1 interaction. AMP-224 is currently undergoing phase I testing as monotherapy in subjects with advanced cancer.

Medi 4736 is an anti-PD-L1 antibody that has demonstrated an acceptable safety profile and durable clinical activity in this dose-escalation study. Expansion in multiple cancers and development of MEDI4736 as monotherapy and in combination is ongoing.

Thus, in certain embodiments, the PD-1 blockers include anti-PD-1 antibodies and similar binding proteins such as nivolumab (MDX 1106, BMS 936558, ONO 4538), a fully human IgG4 antibody that binds to and blocks the activation of PD-1 by its ligands PD-L1 and PD-L2; pembrolizumab/lambrolizumab (MK-3475 or SCH 900475), a humanized monoclonal IgG4 antibody against PD-1; CT-011 a humanized antibody that binds PD-1; AMP-224 is a fusion protein of B7-DC; an antibody Fc portion; BMS-936559 (MDX-1105-01) for PD-L1 (B7-H1) blockade. Other immune-checkpoint inhibitors include lymphocyte activation gene-3 (LAG-3) inhibitors, such as IMP321, a soluble Ig fusion protein (Brignone, et al., 2007, J. Immunol. 179:4202-4211). Other immune-checkpoint inhibitors include B7 inhibitors, such as B7-H3 and B7-H4 inhibitors. In particular, the anti-B7-H3 antibody MGA271 (Loo, et al., 2012, *Clin. Cancer Res.* July 15 (18) 3834). Also included are TIM3 (T-cell immunoglobulin domain and mucin domain 3) inhibitors (Fourcade, et al., 2010, *J. Exp. Med.* 207:2175-86 and Sakuishi, et al., 2010, J. Exp. Med. 207:2187-94).

The precise effective amount for any particular medicine administered to a subject will depend upon their size and health, the nature and extent of their condition, and the therapeutics or combination of therapeutics selected for administration. The effective amount for a given patient is determined by routine experimentation and is within the judgment of a clinician. Therapeutically effective amounts of the present antibody compounds can also comprise an amount in the range of from about 0.1 mg/kg to about 150 mg/kg, from about 0.1 mg/kg to about 100 mg/kg, from about 0.1 mg/kg to about 50 mg/kg, or from about 0.05 mg/kg to about 10 mg/kg per single dose administered to a harvested organ or to a patient. Known antibody-based pharmaceuticals provide guidance in this respect. For example, Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m$^2$; for example.

A therapeutically effective amount for any individual patient can be determined by the health care provider by monitoring the effect of the antibody compounds on tumor regression, circulating tumor cells, tumor stem cells or anti-tumor responses. Analysis of the data obtained by these methods permits modification of the treatment regimen during therapy so that optimal amounts of antibody compounds of the present disclosure, whether employed alone or in combination with one another, or in combination with another therapeutic agent, or both, are administered, and so that the duration of treatment can be determined as well. In this way, the dosing/treatment regimen can be modified over the course of therapy so that the lowest amounts of antibody compounds used alone or in combination that exhibit satisfactory efficacy are administered, and so that administration of such compounds is continued only so long as is necessary to successfully treat the patient. Known antibody-based pharmaceuticals provide guidance relating to frequency of administration e.g., whether a pharmaceutical should be delivered daily, weekly, monthly, etc. Frequency and dosage may also depend on the severity of symptoms.

In some embodiments, antibody compounds of the present disclosure can be used as medicaments in humans, administered by a variety of routes including, but not limited to, oral, intravenous, intramuscular, intra-arterial, intramedullary, intraperitoneal, intrathecal, intraventricular, transdermal, transcutaneous, topical, subcutaneous, intratumoral, intranasal, enteral, sublingual, intravaginal, intravesicular or rectal routes. The compositions can also be administered directly into a lesion such as a tumor. Dosage treatment may be a single dose schedule or a multiple dose schedule. Typically, the therapeutic compositions can be prepared as injectables, either as liquid solutions or suspensions. Solid forms suitable for solution in, or suspension in, liquid vehicles prior to injection can also be prepared.

The current method of treatment of HCC is unique in that it uses a gene expression profile to determine that the subject would respond to immunotherapy. To date, this combination of obtaining a genetic profile of the subject's tumor with the use of immunotherapy has not been used in HCC treatment nor the treatment of other cancers with immunotherapy. This nonconventional way of treating HCC will result in better patient outcomes.

Kits

It is contemplated that all of the methods and assays disclosed herein can be in kit form for use by a health care provider and/or a diagnostic laboratory.

Assays for the detection and quantitation of one or more of the gene biomarkers can be incorporated into kits. Such kits would include probes for one or more of the genes listed in Table 3, FIGS. 10, 11, and/or 12, reagents for isolating and purifying nucleic acids from biological tissue or bodily fluid, reagents for performing assays on the isolated and purified nucleic acid, instructions for use, and reference values or the means for obtaining reference values in a control sample for the included genes.

A preferred embodiment of these kits would have the probes attached to a solid state. A most preferred embodiment would have the probes in a microarray format wherein nucleic acid probes for one or more of the genes from Table 3, FIGS. 10, 11, and/or 12 would be in an ordered arrangement on a surface or substrate.

EXAMPLES

The following examples are included to demonstrate embodiments of the disclosure. The following examples are presented only by way of illustration and to assist one of ordinary skill in using the disclosure. The examples are not intended in any way to otherwise limit the scope of the disclosure. Those of ordinary skill in the art should, in light of the present disclosure, appreciate that many changes can be made in the specific embodiments which are disclosed and still obtain a like or similar result without departing from the spirit and scope of the disclosure.

Example 1—Materials and Methods for Examples 2-10 Patients and Samples

For the purpose of the study, the gene expression profile from a total of 956 HCC human samples was analyzed (FIG. 1), including a training cohort of 228 surgically resected fresh frozen (FF) samples (Heptromic dataset, GSE63898). All samples of the training set were previously obtained from two institutions of the HCC Genomic Consortium upon IRB approval: IRCCS Istituto Nazionale Tumori (Milan, Italy) and Hospital Clínic (Barcelona, Spain). RNA profiling and methylation data were available for all 228 HCC samples and 168 non-tumor liver adjacent cirrhotic tissues and are published elsewhere (Villanueva, et al. 2015). Additional 728 HCC samples of patients with mixed etiology from 7 independent datasets were used for external validation (FIG. 1). Additional 728 HCC samples of patients with mixed etiology from 7 independent datasets were used for external validation (FIG. 1).

One of these datasets, the Validation set, included 131 FFPE tissue samples previously collected by the inventors and profiled with DASL (Illumina, Inc., San Diego, Calif.) technology (GSE20140, samples not overlapping with the training set) (Chiang, et al. 2008; Villaneuva, et al. 2011). Six additional publicly available datasets, including the TCGA cohort (n=190) profiled by RNA-sequencing on Illumina HiSeq 2000 platform and 5 additional microarray-profiled sets (Lee, et al. 2004; Chen, et al. 2002; Iizuka, et al. 2003; Boyault, et al. 2007; Hoshida, et al. 2009), were used for further validation. Clinico-pathological data and follow-up for patients included in the training and validation datasets (Validation and TCGA sets) are summarized in Table 1.

Clinicopathological parameters of the additional datasets have been reported elsewhere (Lachenmayer, et al. 2012).

TABLE 1

Clinical Characteristics of the Training (Heptromic) and Validation Cohorts (Validation and TCGA Sets)

| Variable[a] | Training set (n = 225) | Validation set (n = 131) | TCGA set (n = 190) |
|---|---|---|---|
| Median age (IQR) | 66 (61-72) | 66 (55-71) | 62 (52-70) |
| Gender, male (%) | 178 (79) | 96 (73) | 123 (65) |
| Etiology (%)[a] | | | |
| Hepatitis C | 101 (46) | 64 (50) | N/A |
| Hepatitis B | 48 (21) | 39 (30) | N/A |
| Alcohol | 33 (15) | 6 (5) | N/A |
| Others | 38 (17) | 19 (15) | |
| Child-Pugh score (%)[a] | | | |
| A | 220 (98) | 123 (98) | 86 (83) |
| B | 3 (1) | 2 (2) | 17 (17) |
| Tumor size, cm (%) | | | |
| <2 | 28 (12) | 17 (13) | N/A |
| Between 2 and 3 | 66 (30) | 31 (24) | N/A |
| >3 | 130 (58) | 81 (63) | N/A |
| Multiple nodules (%) | | | |
| Absent | 168 (75) | 117 (91) | N/A |
| Present | 56 (25) | 12 (9) | N/A |

TABLE 1-continued

Clinical Characteristics of the Training (Heptromic) and
Validation Cohorts (Validation and TCGA Sets)

| Variable[a] | Training set (n = 225) | Validation set (n = 131) | TCGA set (n = 190) |
|---|---|---|---|
| Vascular invasion (%) | | | |
| Absent | 144 (65) | 78 (62) | 104 (66) |
| Present | 78 (35) | 46 (38) | 54 (34) |
| Satellites (%) | | | |
| Absent | 164 (73) | 100 (80) | N/A |
| Present | 60 (27) | 25 (20) | N/A |
| BCLC early stage, 0-A (%) | 195 (87) | 120 (94) | N/A |
| Degree of tumor differentiation (%) | | | |
| Well | 33 (15) | 31 (26) | 31 (17) |
| Moderately | 106 (47) | 73 (61) | 96 (52) |
| Poor | 44 (20) | 16 (13) | 58 (31) |
| Bilirubin, >1 mg/dL (%) | 113 (50) | 34 (27) | 35 (25) |
| Albumin, <3.5 g/L | 26 (12) | 13 (11) | 42 (31) |
| Platelet count <100,000/mm$^3$ (%) | 41 (18) | 17 (13) | N/A |
| AFP, >100 mg/dL (%) | 51 (23) | 38 (31) | 43 (33) |
| Events (%) | | | |
| Recurrence | 150 (67) | 78 (60) | 88 (59) |
| Death | 133 (59) | 46 (35) | 84 (44) |
| Median follow-up, months | 49 | 51 | N/A |

AFP—alfa feto-protein; BCLC—Barcelona Clinic Liver Cancer; IQR—interquartile range; N/A—not available.
[a]Missing values Training set: etiology (n = 2);
Child-Pugh score (n = 2);
Multiple nodules (n = 1);
Vascular invasion (n = 3);
BCLC 0-A (n = 2);
Tumor differentiation (n = 42);
Bilirubin (n = 32);
AFP (n = 11);
Albumin and bilirubin (n = 4);
Platelet (n = 2);
Recurrence (n = 7).
Missing values Validtion set: etiology (n = 3);
Child-Pugh score (n = 6);
Tumor size (n = 2);
Multiple nodules (n = 2);
Vascular invasion (n = 6);
Satellites (n = 6);
BCLC 0-A (n = 4);
Tumor differentiation (n = 4);
Bilirubin (n = 6);
AFP (n = 10);
Albumin (n = 9);
Platelet (n = 5);
Recurrence (n = 1).
Missing values TCGA set: Child-Pugh score (n = 87);
Vascular invasion (n = 32);
Tumor differentiation (n = 5);
Bilirubin (n = 50);
AFP (n = 58);
Albumin (n = 55);
Inaccurate platelet count;
Recurrence (n = 40);
Etiology, tumor size and number, satellites, and updated follow-up information not available.

Identification of the Immune Expression Pattern and Unsupervised Clustering

Virtual microdissection of gene expression data was performed in the training set using unsupervised non-negative matrix factorization (NMF, Gene Pattern module) (Brunet, et al. 2004), as previously described (Moffitt, et al. 2015), with k=10 as the number of factors. An immune-related expression pattern was unveiled by integrating NMF-identified factors with the immune enrichment score (Yoshihara, et al. 2013) calculated by single sample Gene set enrichment analysis (ssGSEA, Gene Pattern module). Once the immune expression pattern was deconvoluted by NMF and characterized by integration with ssGSEA scores, the top-ranked genes (or exemplar genes) were listed according to their loadings. Exemplar genes of the immune expression pattern were further characterized by Ingenuity Pathway analysis (IPA). Unsupervised clustering on these exemplar genes was then performed using NMF consensus (Gene Pattern module). Robustness of the obtained class was evaluated using a conventional Random Forest procedure (Breiman 2001).

Molecular Characterization of the Immune Class

Enrichment of molecular pathways and gene expression signatures was evaluated using GSEA, ssGSEA, and Nearest Template Prediction (NTP) analyses (Gene Pattern modules) (Reich, et al. 2006). To this end, Molecular Signature Database gene sets and previously reported gene-expression signatures representing different states of inflammation or distinct immune cells were tested (Moffitt, et al. 2015; Yoshihara, et al. 2013; Cancer Genome 2015; Finkin, et al. 2015; Messina, et al. 2012; Quigley, et al. 2010; Spranger, et al. 2015; Coates, et al. 2008; Bindea, et al. 2013; Alistar, et al. 2014; Ribas, et al. 2015; Chow, et al. 2016; Calon, et al. 2012; Rooney, et al. 2015) (FIG. 2). Previously published HCC molecular classifications were also analyzed (Chiang, et al. 2008; Hoshida, et al. 2009; Coulouarn, et al. 2008; Hoshida, et al. 2008) (FIG. 2). Prediction of previously published HCC molecular classification was performed using NTP analysis (Gene Pattern). Genes over-expressed in the Immune class versus rest and in the Exhausted Immune Response Type versus the Active Immune Response Type were identified by comparative marker selection (CMS, Gene Pattern) with FDR<0.05 and fold change (FC) equal to or greater than 3. Exemplar genes were then characterized by David Functional Annotation. GSEA was applied to identify pathways enriched in each subgroup.

Immunohistochemistry and Evaluation of Immune Infiltration and Presence of Tertiary Lymphoid Structure Presence of immune infiltration and TLSs was analyzed by an expert pathologist (S. T.). Hematoxylin eosin (H&E) stained slides were evaluated and scored according to the amount of immune infiltration as: 0=absence of immune cell infiltration, 1=minimal, 2=mild infiltration, 3=moderate and 4=severe infiltration. Samples with staining between 0 and 2 were considered with low immune infiltration whereas 3 and 4 scores were classified as high immune infiltration. Presence of TLS was also quantified on H&E slides. TLSs were assessed as continuous variable as well as categorized as negative (<than 5 foci, 10x) or positive (greater or equal than 5 foci, 10x).

Immunohistochemistry for PD-1 and PD-L1 was performed in a subset of 100 patients belonging to the training cohort (within and outside the Immune class). Immunohistochemical staining was carried out on 3-μm-thick FFPE tissue sections after heat-induced antigen retrieval in microwave with 10 mM TRIS-EDTA (pH=9). The primary antibodies used were anti-PD1 (Abcam, clone NAT105), and anti-PD-L1 (Abcam, clone 28-8) Immunostaining positivity of PD-1 and PD-L1 was assessed by two expert pathologists (J. P. and S. T.) blinded to the expression profiling results. Positive staining for PD1 was measured semi-quantitatively (PD-1/high versus PD-1/low) as previously described (Calderaro, et al. 2016). Briefly, PD-1 was observed only in intra-tumoral foci of inflammatory cell clusters distributed throughout the tumor. The number of clusters was counted (20×) and samples were classified as PD-1/high if the number of clusters within the tumor was equal to or higher than the median of clusters. On the other end, PD-L1 expression was assessed only in neoplastic HCC cells as intratumoral inflammatory cells were largely negative.

As previously described in HCC and other cancers, the percentage of neoplastic cells displaying membranous staining was recorded and tumors with at least 1% of positive cells were classified as positive (Calderaro, et al. 2016; Robert, et al. 2015; Garon, et al. 2015; Borghaei, et al. 2015).

Analysis of Methylation Profile in the Immune Class

Methylation data for all patients included in the training cohort was already available and published elsewhere. Briefly, bisulfite-converted DNA (bs-DNA) was processed with the Infinium FFPE restoration process and then hybridized on Infinium HumanMethylation450 BeadChip array following the manufacturer's instructions (Illumina). Resulting raw intensity data (IDATs) were normalized by using the Illumina normalization method developed under the minfi R package (v 1.12.0). After the normalization step, probes related to Y chromosome were removed, as well as those probes whose 10 bases nearer the interrogated site contained a SNP, as annotated on the product description file. Moreover, CpG sites with associated p-value greater than 0.01 were discarded for the analysis. Finally, only CpG sites present in promoter regions were selected. For supervised heatmap representation of the three different groups analyzed (Exhausted Immune Response, Active Immune Response, Rest), CpG sites were selected by applying an ANOVA analysis to identify statistically significant CpG sites (FDR adjusted p-value<0.05) that were differentially methylated among the groups ($\Delta\beta$>0.2). Selected CpG sites were later clustered based on the Manhattan distances aggregated by Ward's linkage.

Generation of the Immune Classifier and Performance Validation in Independent Datasets The Immune gene signature classifier was generated using genes differentially expressed between HCC samples belonging or not to the Immune class (FDR<0.05, FC≥3) in the training set (Heptromic cohort, n=228). The ability of the signature to capture the Immune class was validated in our Validation set (GSE20140) and 6 publicly available datasets using NTP analysis (Gene Pattern). Two patients receiving nivolumab off-label were included in the study to assess the capacity of the immune classifier to predict response to immunotherapy. Upon patients' consent, RNA extraction and RNA profiling were performed on tumoral sections derived from available archived tissues collected any time before treatment (GSE93647) using the Affymetrix Human Genome U219 Array Plate (Affymetrix, Inc., Santa Clara, Calif.). Class mapping (SubMap) analysis (Gene Pattern), a bioinformatics method to quantitatively evaluate similarity of molecular classes between independent patient cohorts on the basis of their expression profiles (Chen, et al. 2016) was used to measure similarity between the gene expression profile of our Immune subtypes and melanoma patients treated with immunotherapies (Chen, et al. 2016; Roh, et al. 2017). In study and follow-up paper, biopsies were obtained prior to initiation of CTLA-4 blockade and on-treatment, prior to PD-1 treatment and on-treatment for those who did not respond to CTLA-4 blockade and after PD-1 therapy for those who did not respond to PD-1 therapy.

Responders were defined by radiographic evidence of absent/stable disease or decreased tumor volume for >6 months whereas non-responders were defined by tumor growth on serial CT scans after treatment initiation. Out of 56 patients included in this study, 32 had gene expression available (Custom Nanostring immune panel) and were compared to HCC patients included in our datasets.

Correlation of the Immune Class with Copy Number Aberrations, Mutations and Neoantigens in the TCGA Dataset Copy number data generated by GISTIC2 (Mermel, et al. 2011) for TCGA-LIHC samples was accessed from the Broad Institute GDAC FireBrowser. Broad values defined by each chromosome arm, which were analyzed independently. First, each of the 190 tumor samples were looked to as to whether each arm or focal region was deleted or amplified. Then, the distribution of the values was compared between the Immune class and the rest, and between the rest and the "Active Immune Response" and "Exhausted Immune Response" subtypes, using the Mann-Whitney test and the Kruskal-Wallis test, as appropriate. The differences in focal high-level amplifications (HLAs) or homozygous deletions (HDs) occurring in driver genes were then assessed as previously reported in HCC (Schulze, et al. 2015). In order to increase the confidence of this analysis, the HLA and HD thresholds were redefined as previously described (Weir, et al. 2007). Briefly, HLAs were called if copy number segments falling within gene boundaries (+/− 20 kb) had a log 2 ratio of >0.85, whereas HD were called if copy number segments had a log 2 ratio of <−0.74, which correspond to 3.6 and 1.2 copies, respectively. The significant HLAs and HD found by GISTIC2 and involving the driver genes reported are listed in FIG. 13. Significant differences were assessed by two-tailed Fisher's exact test. Values of $p<0.05$ were considered significant. Statistical analyses were performed using the R statistical software.

For the analysis of mutations and neo-antigens, the list of events per sample provided in the Table S4A of Rooney et al. Cell 2015 was used. This data had been obtained from the GDAC Firehose standard analysis pipeline. Briefly, POLYSOLVER-based mutation detection pipeline for characterizing HLA alleles and identifying HLA mutations was first applied. Then, Individual-specific HLA-binding peptides were identified by a neo-antigen prediction pipeline previously reported. Binding affinities of all possible 9 and 10-mer mutant peptides to the corresponding POLYSOLVER-inferred HLA alleles were predicted using NetMHCpan (v2.4) (Nielsen, et al. 2007).

Statistical Analysis

All analyses were performed using SPSS software version 22. Correlations between molecular classes, histological markers and clinico-pathological variables were analyzed by Fisher's exact test and Wilcoxon rank-sum test for categorical and continuous data, respectively. All signatures used in the study were previously reported (FIG. 2).

Kaplan-Meier estimates, log-rank test, and Cox regression modeling were performed to analyze the association of molecular and clinical variables with overall survival and tumor recurrence. Multivariate analysis in the TCGA set was not performed due to absence of key variables known to be associated with outcome (i.e., tumor size and number, satellites, etc.).

Example 2—Identification of an Immune Class of HCC

In order to isolate immune-related genomic signals from bulk gene expression data in HCC tumors, NMF analysis of 228 resected HCC samples was performed (training cohort, FIG. 1). Clinical characteristics of the training cohort are summarized in Table 1. Among the distinct expression patterns identified by NMF, one was attributed to the presence of inflammatory response and immune cells through integration with a previously reported immune enrichment score. Analysis of the top-ranked genes (named exemplar genes) that defined this expression pattern further confirmed immune-related functions and signaling. Consensus clustering on exemplar genes identified a new molecular subgroup accounting for 24% of the cohort (55/228), referred herein as the "Immune class" (FIG. 3).

Figures 3, 3A:
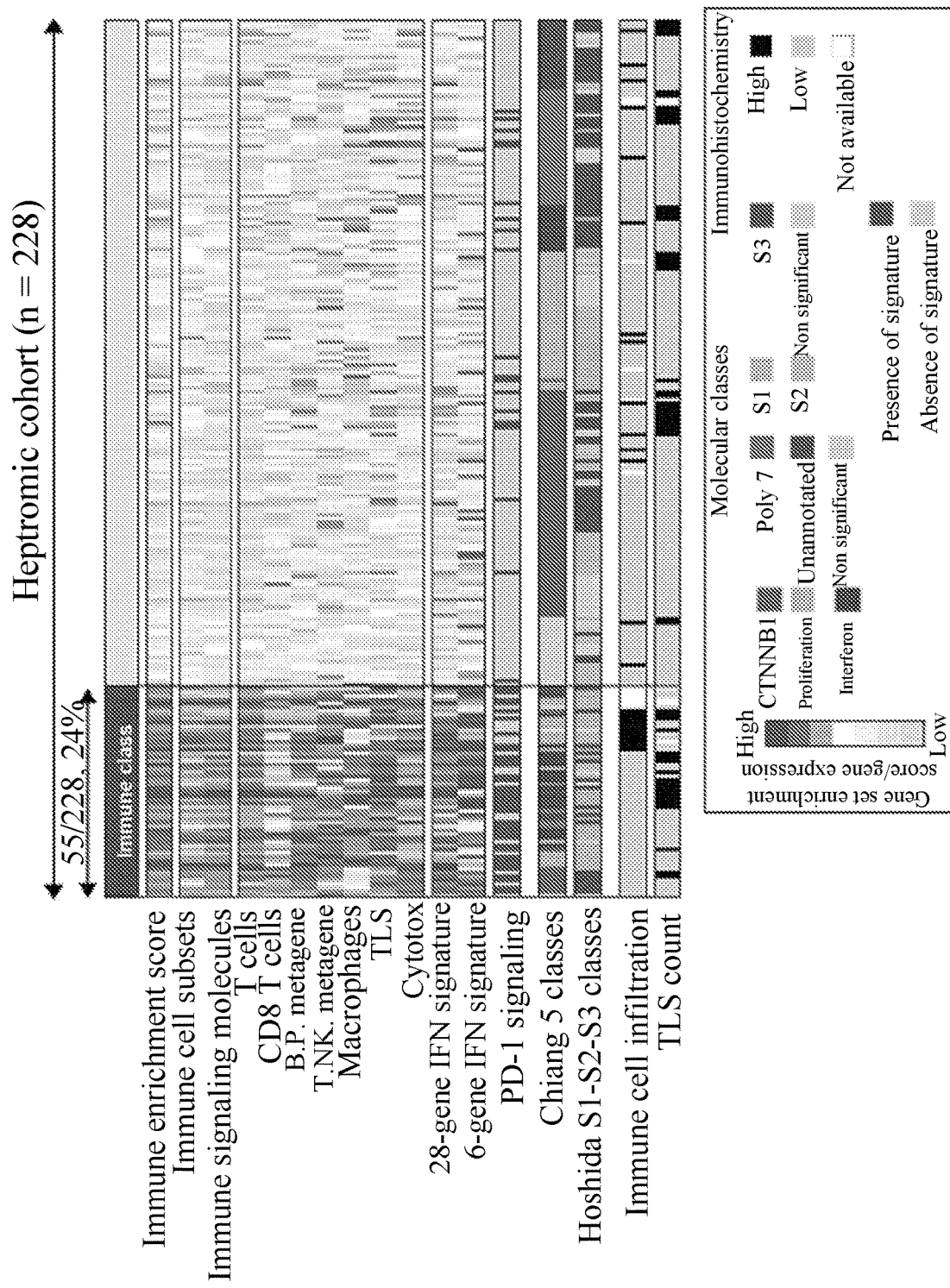
FIG. 3 shows the identification of the Immune class of HCC.
FIG. 3A shows consensus-clustered heatmap of HCC samples (training dataset, n=228) using exemplar genes of the immune expression pattern and refined by Random Forest. In the heatmap, high and low gene set enrichment scores are represented in red and blue, respectively. Positive prediction of signatures is indicated in red and absence in grey. Similar results were obtained with both signatures.

Patients belonging to the Immune class showed significant enrichment of signatures identifying immune cells (i.e. T cells, cytotox, tertiary lymphoid structures (TLS), and macrophages (p<0.001), immune metagenes, IFN gene signatures predictive of response to pembrolizumab in melanoma (28-genes, p<0.001)) and head and neck squamous cell carcinoma (6-genes, p<0.001), and PD-1 signaling (36/55 vs19/173, p<0.001) (FIG. 3A).

Class comparison between the Immune class and remaining samples identified 112 genes significantly deregulated (Immune Classifier, FIGS. 10-D), including 108 overexpressed immune-related genes such as T cell Receptor components and chemo-attractants for Natural Killer (NK) and T cells (CCL5, CXCL9 and CXCL10, p<0.001) (FIGS. 11A-D). Similarly, GSEA identified enrichment of IFN alpha and gamma signaling, inflammatory response (i.e. lymphocyte activation, T helper 1-cytotoxic module, NK-mediated toxicity, etc.), TGF-β and JAK/STAT signaling (FDR<0.001) (results not shown).

It was next sought to integrate the Immune class with previously reported HCC molecular classifications. This revealed an enrichment of the IFN-related (18/55 vs 12/173, p=0.0001) and S1 classes (TGF-β/WNT activation) (32/55 vs 15/173, p=0.0001), as well as a significant exclusion of S2 (2/55 vs 46/173, p=0.0001) and CTNNB1 classes (8/55 vs 59/173, p<0.001, FIG. 3A).

All together, these data showed the identification of an immune-related class of HCC enriched with signatures capturing the presence of immune cells, signatures of response to immune checkpoint therapy, and IFN signaling.

Example 3—Immune Class Immuno-Phenotype Shows Enrichment of PD-1/PD-L1 Signaling Immunophenotyping was performed to gain further biological insight into the immunological nature of the Immune class. As predicted, patients belonging to this class had significantly higher rates of immune cell infiltration (11/49 vs 14/167, p=0.01, FIGS. 3A and 3B) and density of TLS (≥5 foci, 19/51 vs 34/170, p=0.01, FIGS. 3A and 3C) as revealed by the examination of hematoxylin and eosin-stained sections.

PD-1 and PD-L1 protein expression by immunohistochemistry was then assessed in a subset of samples of the training cohort (within the Immune class and outside, FIG. 3B). Overall, PD-L1 tumoral expression was observed in 16% (16/99) of HCC in accordance with recent reports. PD-1 protein expression was observed in 10% of the cohort (10/99), but no significant correlation was found between high PD-1 and PD-L1 expression, likely due to the small sample size. Nonetheless, tumors with high PD-1 (8/48 within the Immune class vs 2/51 in the rest, p=0.4) and PD-L1 (12/48 within in the Immune class vs 4/51 in the rest, p=0.03) protein expression were significantly enriched in the Immune class. No difference was observed between the Immune class and the rest of the cohort in terms of other clinico-pathological variables (data not shown, p>0.05).

In summary, pathological examination revealed that patients belonging to the Immune class showed a high degree of immune infiltration, higher immunohistochemical expression of PD-1/PD-L1, and presence of TLS. These data underscore the performance of the Immune Classifier to capture molecular signals deriving from infiltrating immune cells in HCC.

Figures 4, 4A:
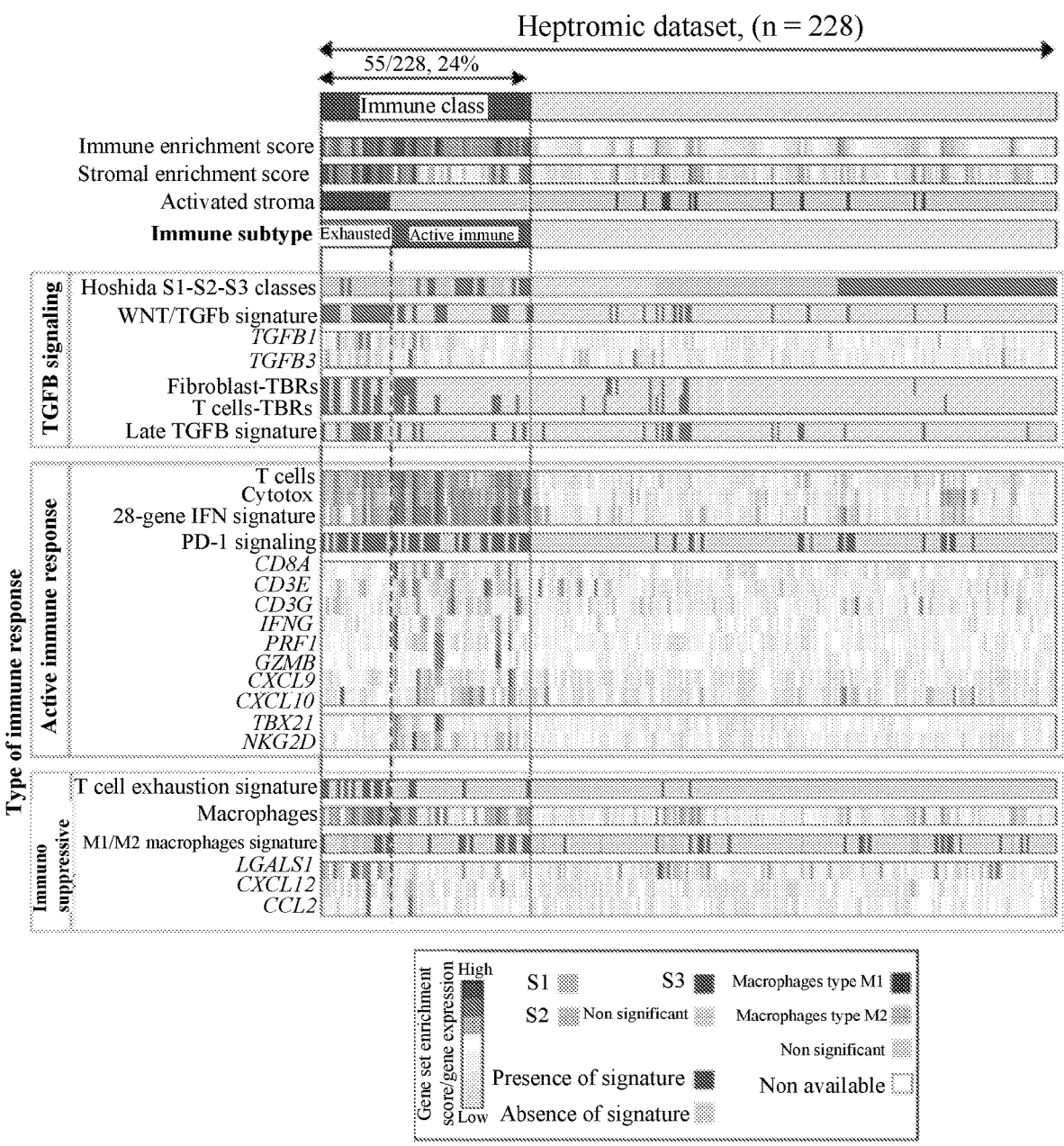
FIG. 4 shows that the Immune class contains two distinct microenvironment-based subtypes.
FIG. 4A is NTP analysis of whole-tumor gene expression data using a molecular signature able to capture activated inflammatory stromal response identified two distinct subtypes of Immune class— the Active (blue color bar) and the Exhausted (green color bar) Immune Response Subtypes. In the heatmap, high and low gene set enrichment scores are represented in red and blue, respectively; same representation is used for high and low gene expression. Positive prediction of signatures as calculated by NTP is indicated in red and absence in grey.

Example 4—the Immune Class Captures Two Distinct Components of the Tumor Microenvironment: Active and Exhausted Subtypes The immune system can exert both anti- and pro-tumor activities. Indeed, cross-talk between cancer cells and the tumor microenvironment triggers immune responses which favor cancer progression by supplying growth factors that sustain proliferation and facilitate epithelial mesenchymal transition (EMT), invasion, and metastasis. To further explore this concept in HCC, immune modulation occurring in response to the tumor microenvironment in patients within the Immune class was analyzed. As depicted in FIG. 4A, 33% of the Immune class (18/55) was characterized by "activated stroma" whereas the remaining patients (37/55, 67%) showed lack of such activation, as predicted by nearest template prediction (NTP) analysis using a previously published molecular signature that captures activated inflammatory stromal response. Interestingly, patients with normal or non-active stroma (37/55, 67%) showed significant enrichment of T cells and IFN signatures, including overexpression of adaptive immune response genes (i.e., T Cell Receptor G, CD8A, IFN-γ, GZMB, etc.) and IFN signatures predictive of response to pembrolizumab (p<0.001). Thus, this cluster was named Active Immune Response.

Figure 4B:
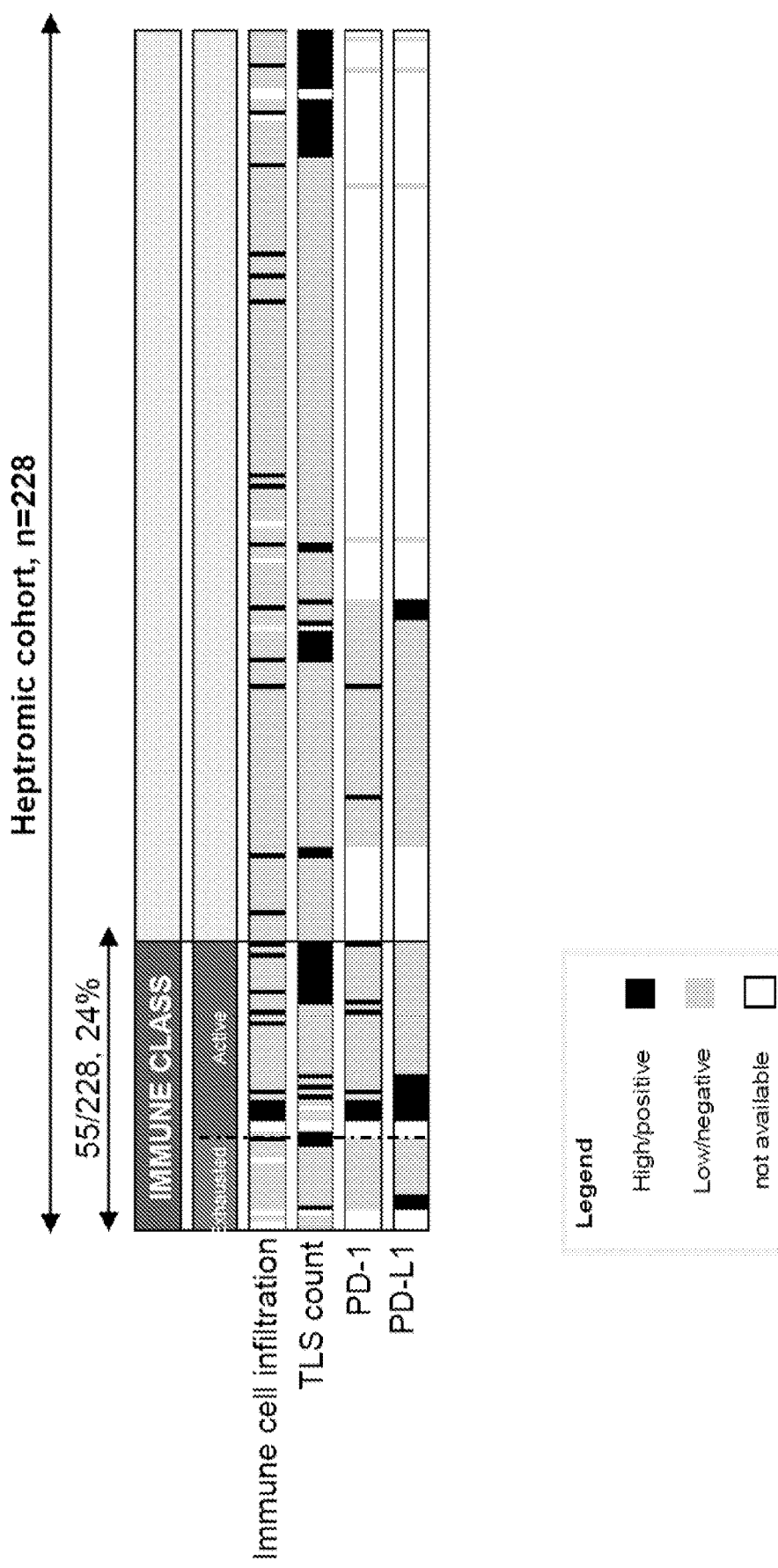
FIG. 4B is a heatmap representation of the distribution of immune cell infiltration (high vs low), TLS [positive (≥5 foci) vs negative (<5 foci)], PD-1 and PD-L1 positive staining in the Immune class versus the rest of the cohort and between the two Immune subtypes. No significant difference was observed between the Active and Exhausted Immune subtype in term of immune infiltration (10/35 vs 1/14, p=0.14), TLS count (≥5 foci, 15/34 vs 4/17, p=0.22), PD-L1 (9/34 vs 3/14, p=1.00) and PD-1 expression (8/34 vs 0/14, p=0.08).
Figure 4C:
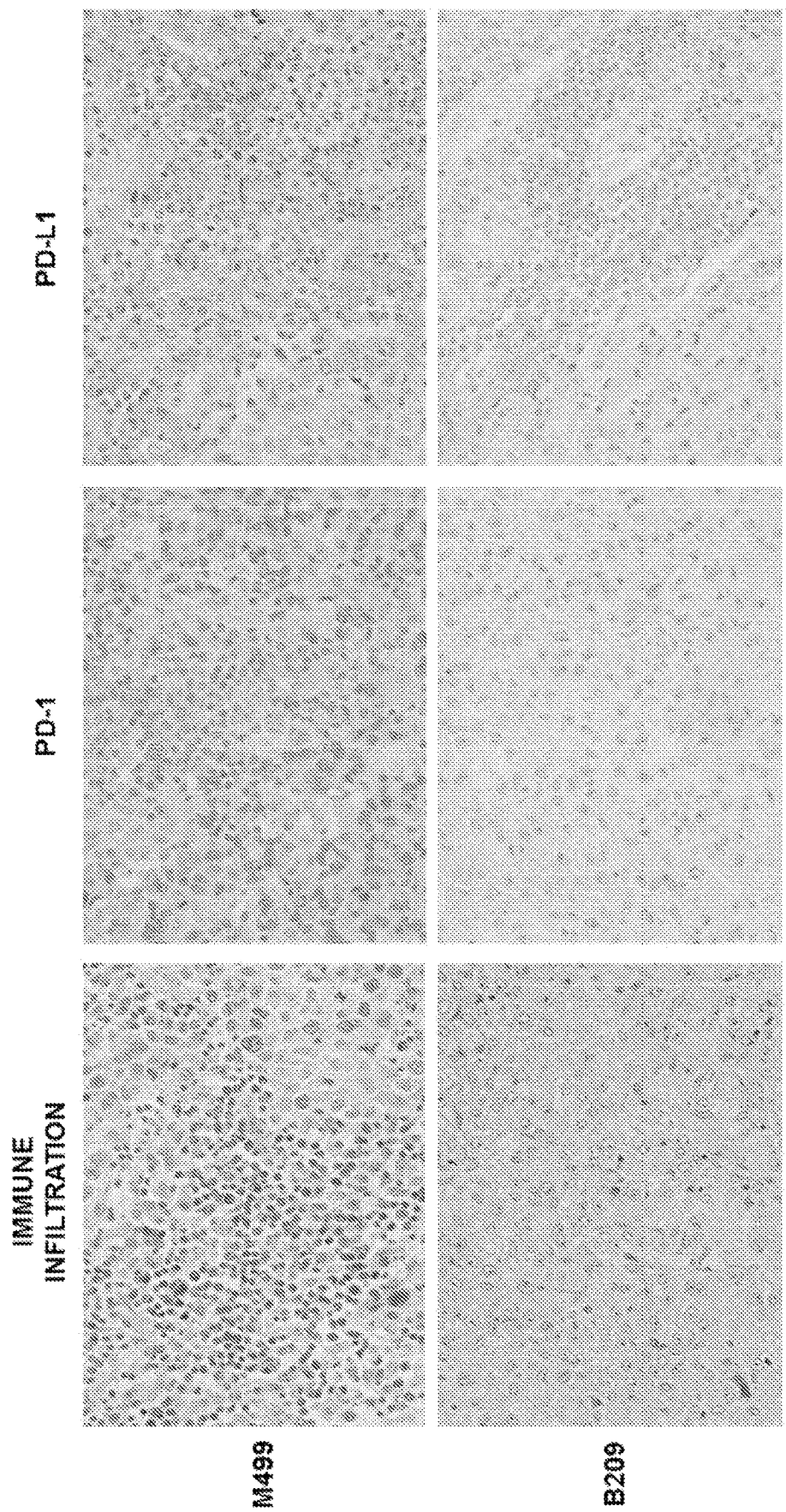
FIG. 4C are representative images of immune cell infiltration, PD-1 and PD-L1 staining in a patient of the Active Immune subtype (M499) and a patient of the Exhausted Immune subtype (B209). Images were captured with 40×.

Conversely, the presence of activated stroma was significantly associated with a T cell exhaustion signature (10/18 vs 4/37, p<0.001), and with immunosuppressive components, such as TGF-ß signaling and M2 macrophages (8/18 vs 1/37, p=0.0003). In particular, overexpression of TGF-ß-1 and -3 along with enrichment of several signatures reflecting activation of TGF-ß pathway, such as late TGF-ß signature (9/18 vs 6/37, p=0.02), S1/TGF-ß signature (16/18 vs 16/37, p=0.001), WNT/TGF-ß signaling (15/18 vs 12/37, p<0.001), and TGF-beta response signatures (TBRS) of fibroblasts (F-TBRS) (9/18 vs 6/37, p=0.02) and T cells (T23TBRS) (10/18 vs 9/37, p=0.03), were observed in this subgroup (FIG. 4A). T cell exhaustion and impaired cytotoxic activity in this cluster was supported by the up-regulation of immunosuppressive factors (i.e. LGALS1, CXCL12) and myeloid chemo-attractants (CCL2). Other essential NK cell activators such as Granzyme B (GZMB) IFN-γ, NKG2D and TBX21 receptors (Hanahan and Weinberg 2011; Slavulijica, et al. 2011), were strongly downregulated (FIG. 4A). Based on these features, this cluster was named Exhausted Immune Response. Gene set enrichment analysis comparing both clusters confirmed the driver role of TGF-ß in the Exhausted Immune Response, and enrichment of pathways related to metastasis, EMT, angiogenesis and liver cancer recurrence, suggesting a more aggressive phenotype (FIGS. 12A-G). Interestingly, no significant difference between the Active and Exhausted Immune subtype in terms of immune infiltration, TLS count, PD-L1 and PD-1 expression were observed (FIGS. 3C, 4B and 4C). It was further explored the potential prognostic implications of the type of immune response by correlating these clusters with clinico-pathological parameters.

Figure 5C:
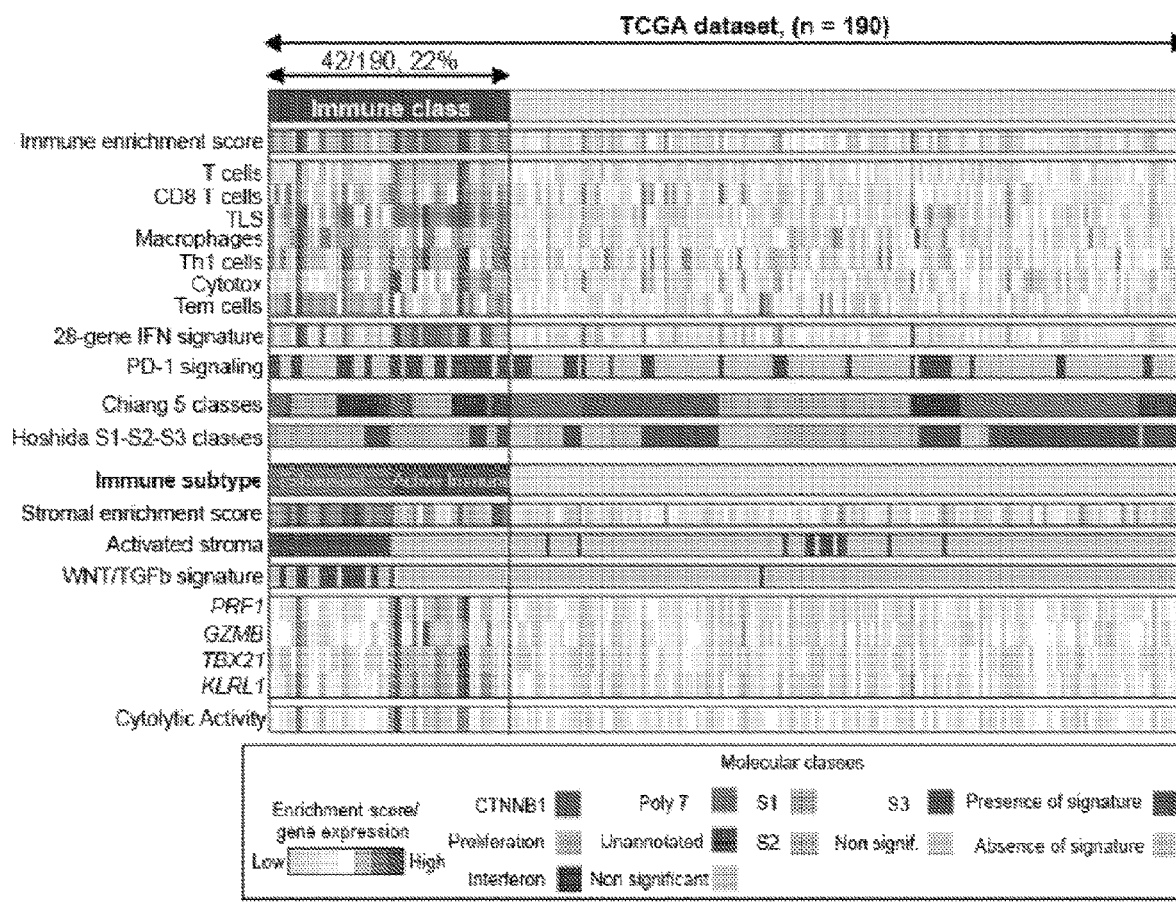
FIG. 5C shows external validation of the Immune class was conducted in the publicly available TCGA dataset.
Figures 5D, 5E:
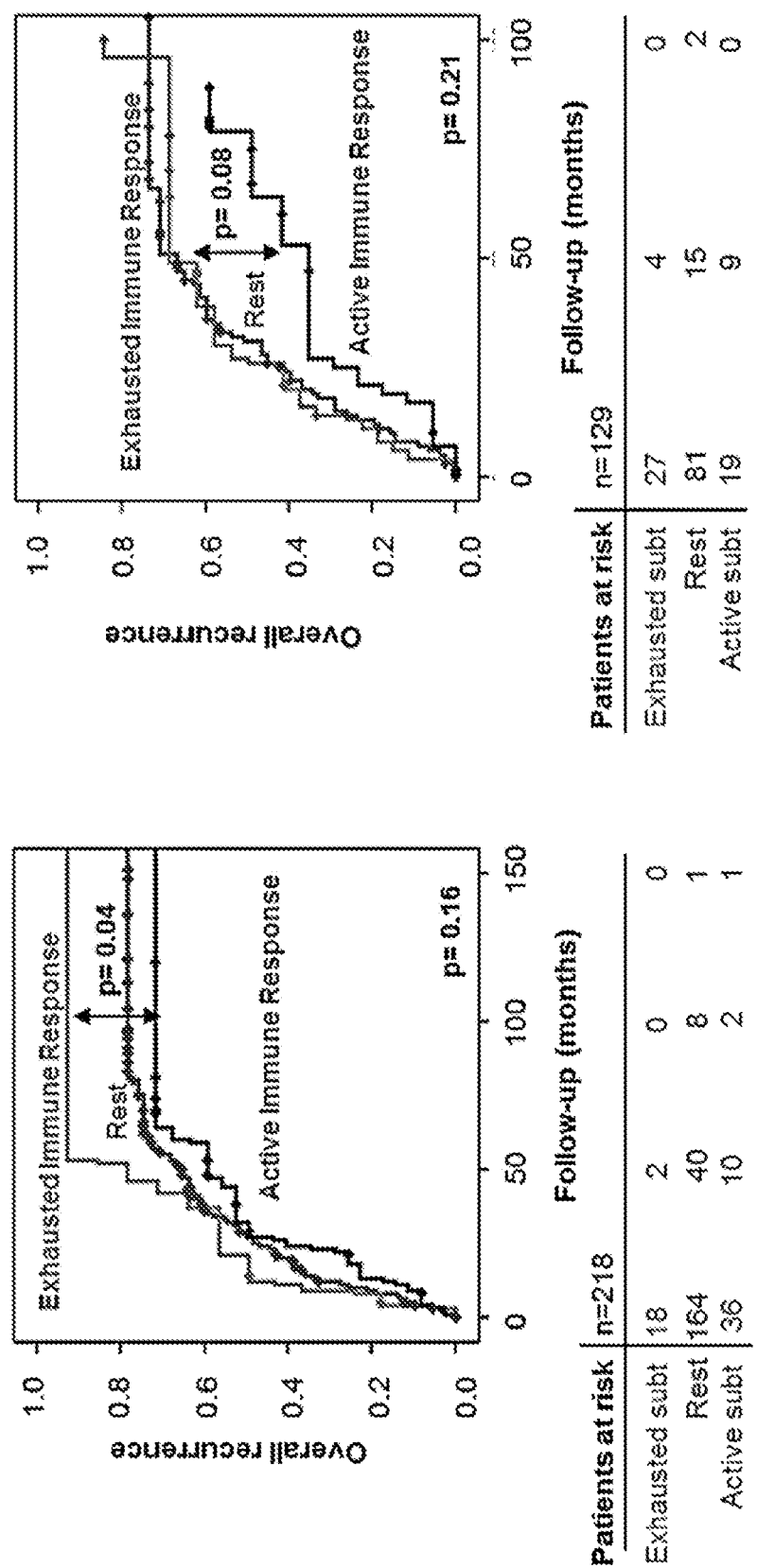
FIG. 5D shows the Kaplan-Meier estimates of overall recurrence according to the microenvironment-based immune subtypes in training cohort. In the training set (Heptromic), patients within the Active Immune Response cluster showed lower rates of tumor recurrence compared to the Exhausted cluster (p=0.04). Non-significant differences were observed between the Active Immune Response cluster and the rest of the cohort (p=0.32), and between the Exhausted Immune Response cluster and the rest (p=0.15).
FIG. 5E shows the Kaplan-Meier estimates of overall recurrence according to the microenvironment-based immune subtypes in the Validation dataset. In the Validation set, only a non-significant trend was observed with a median of 79 months in the Active Immune Response Subtype versus 27 months in the Exhausted Immune Response Subtype (p=0.14) and 31 months in the rest of the cohort (p=0.08).

Interestingly, patients within the Active Immune Response cluster showed lower rates of tumor recurrence after resection compared to the Exhausted Immune Response cluster (median time to recurrence 32 versus 21 months, p=0.0, FIGS. 5D and 5E). A trend towards better survival was also observed (median survival time of 88 months in the Active Immune vs 63 months in remaining patients, p=0.07) (FIG. 5A). No differences in other clinic-pathological variables, including HBV and HCV infection, were found between the distinct Immune subtypes (results not shown). Notably, the Active Immune subtype was retained as independent prognostic factor of overall survival (HR=0.58, CI 0.34-0.98, p=0.04) along with vascular invasion, multi nodularity, platelets count, and HCV infection.

Altogether, these data divided the Immune class in two distinct microenvironment-based components: a) Active Immune Response Subtype (~65%) characterized by over-expression of adaptive immune response genes (FIG. 4), and b) Exhausted Immune Response Subtype (~35%) characterized by the presence of immunosuppressive signals (i.e. TGF-β, M2 macrophages).

Example 5—the Immune Class is Validated Across Datasets

The presence of the Immune class was further evaluated in 7 additional datasets (n=728HCCs, FIG. 1) using the 112 gene-expression based Immune Classifier (FIGS. 10A-D). Firstly, the Immune Classifier was applied to the TCGA dataset, the largest data set publicly available [n=190 fresh frozen (FF) samples] profiled by RNA-sequencing]. Similar to the training cohort, 42/190 (22%) HCC samples were successfully predicted within the Immune class. Molecular characterization of the Immune class confirmed a significant enrichment of signatures identifying immune cells (i.e. T cells, cytotox, TLS and macrophages, p<0.001), signatures predictive of response to immune checkpoint therapy (p<0.001) and PD-1 signaling (24/42 vs 31/148, p<0.001) (FIG. 5C). Compared to known HCC molecular classes, the enrichment of the IFN-related (13/42 vs 11/148 in the rest, p<0.001) and S1 classes (28/42 vs 20/148 in the rest of cohort, p<0.001) was confirmed, and the significant exclusion of the CTNNB1 class (2/42 vs 30/148 in the rest of the cohort, p<0.001) as previously observed in the training cohort. In addition, half of the TCGA-Immune class showed lack of the activated stroma signature along with over-expression of adaptive immune response genes, recapitulating the Active Immune Response Subtype (FIG. 5C).

On the other end, the remaining half of patients showed activated stroma which was associated with TGF-ß signaling (11/21 vs 1/21 in the rest of the Immune class, p=0.01) and down-regulation of NKG2D and TBX21 Receptors (p<0.01), main characteristics of the Exhausted Immune Response subtype. Correlation with clinical outcomes confirmed that patients within the Active Immune Response subtype had a better survival (median survival time of 107 months in the Active Immune cluster vs 33 months in the remaining patients, p=0.03) (FIG. 5B).

Next the Validation cohort previously collected by our group [n=131 formalin fixed paraffin embedded (FFPE) HCCs] and 5 additional datasets including 4 testing FF tissues (n=289) and 1 of FFPE samples (n=118) were interrogated (FIG. 1). The percentage of patients allocated to the Immune class was consistent across all FF datasets with an average of 27% of the samples predicted to this class (range 22-28). In the two FFPE datasets (Validation and HCC-V), 37% (48/131) and 30% (35/118) of patients were allocated to the Immune class, respectively (results not shown). The higher percentage could be due to the different genomic platform used [DASL (Illumina) versus Affymetrix] or a different type of tissue material (FFPE versus FF samples). Nonetheless, molecular characteristics of the Immune class and the presence of the two microenvironment-based subtypes were successfully recapitulated in all datasets tested regardless of the platform and type of samples used.

Finally, the capacity of the Immune class to predict response to immunotherapy was tested. The tumoral gene expression derived from two HCC patients treated with nivolumab was analyzed for the presence of the immune classifier rendering a positive result for patient #1 (FDR=0.001) who showed a partial response but not for patient #2 (FDR=0.23) who presented with stable disease. FIG. 8.

Considering that checkpoint inhibitors are not yet approved for HCC management by regulatory agencies the gene expression profile of the Immune class was compared with the expression profiles of melanoma patients responding to immunotherapy using a recently published dataset of 32 patients. SubClass mapping analysis revealed that the Immune class, and in particular the Active Immune subtype, shows similarity to the group of melanoma patients who respond to PD-1 checkpoint inhibitors. FIG. 9.

Example 6—Immune Class Tumors Show Lower Burden of Chromosomal Aberrations but No Differences in the Expression of Neo-Antigens or Tumoral Mutational Burden Recent analyses have linked the tumoral genomic landscape with anti-tumor immunity (Le, et al. 2015; Rooney, et al. 2015; McGranahan, et al. 2016). In particular, it has been proposed that presence of neo-antigens and overall mutational load might drive T cell responses whereas tumor aneuploidy correlates with markers of immune evasion and reduced response to immunotherapy (Roh, et al. 2017; Davoli, et al. 2017). In order to verify if the burden of somatic copy number aberrations (SCNAs) and mutated neo-antigens may influence local immune infiltrates in HCC, the TCGA dataset was used. In a recent analysis, the local immune cytolytic activity of several tumors showed strong correlation with cytotoxic T cells and interferon stimulated chemokines that attract T cells (Rooney, et al. 2015). Interestingly, in HCC patients a strong correlation was observed between the cytolytic activity score and the Immune class (p<0.0001, FIG. 5C). In terms of SCNAs, patients within the Immune class showed lower burden of gains and losses, both broad and focal (FIGS. 6A and 6B) with a median of broad gains (range 0-16) and 3.5 broad losses (range 0-20) in the Immune class versus broad gains (range 0-22) and 9 broad losses (range 0-26) in the rest of the cohort (p=0.046 and p=0.01, respectively). Similarly, a median of 5 focal gains (range 0-18) and 9 focal losses (range 0-25) was identified in the Immune class versus 8.5 focal gains (range 0-20) and 13 focal losses (range 0-27) in the rest of the cohort (p=0.03 for both comparisons). When analyzing the regions associated with recurrent SCNAs in patients outside the Immune class (low immune infiltrates based on immune signatures), recurrent copy number gain in chromosome 1q and recurrent losses in chromosomes 3p, 17p, and 18p were observed at arm level. In terms of focal high-level amplifications and homozygous deletions, the analysis was restricted to focal structural aberrations involving driver genes previously reported in HCC (Schulze, et al. 2015). A significant difference was found for the high-level amplification of the locus 11q13 (CCND1, FGF19, etc.), which was significantly enriched in the Immune class, and particularly in the Active Immune subtype. No significant differences were found regarding loci involving MYC, TERT and PTEN.

Figure 6C:
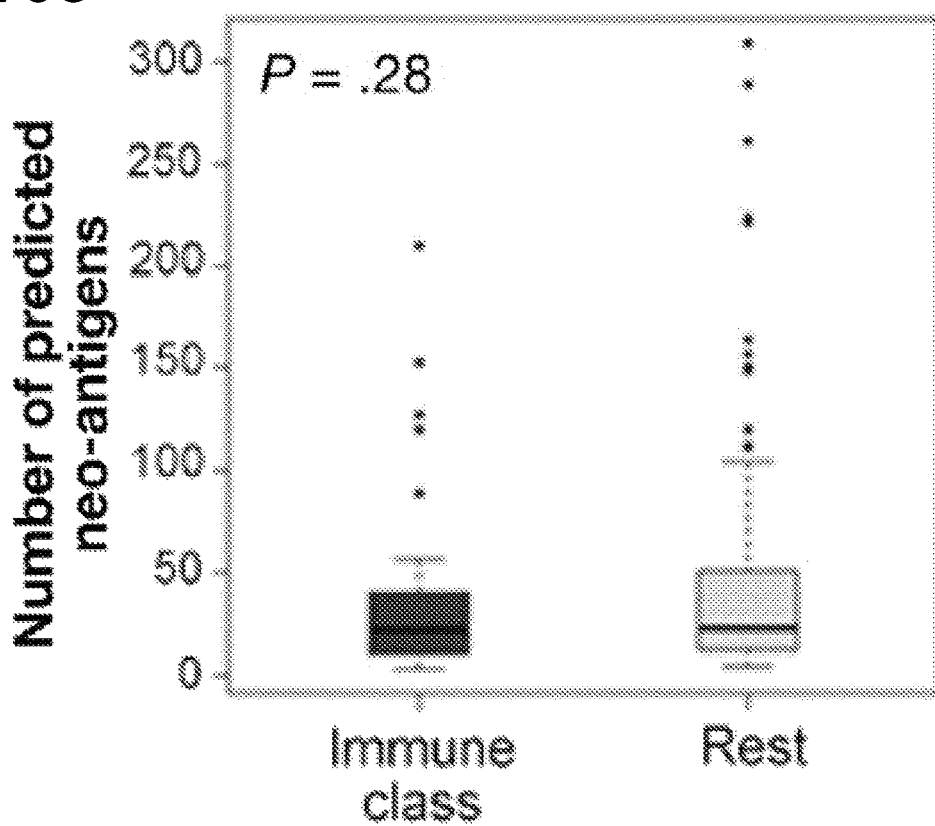
FIG. 6C is a graph showing the rate of mutations predicted to yield a neo-antigen was similar between the Immune class and the rest of the cohort.
Figure 6D:
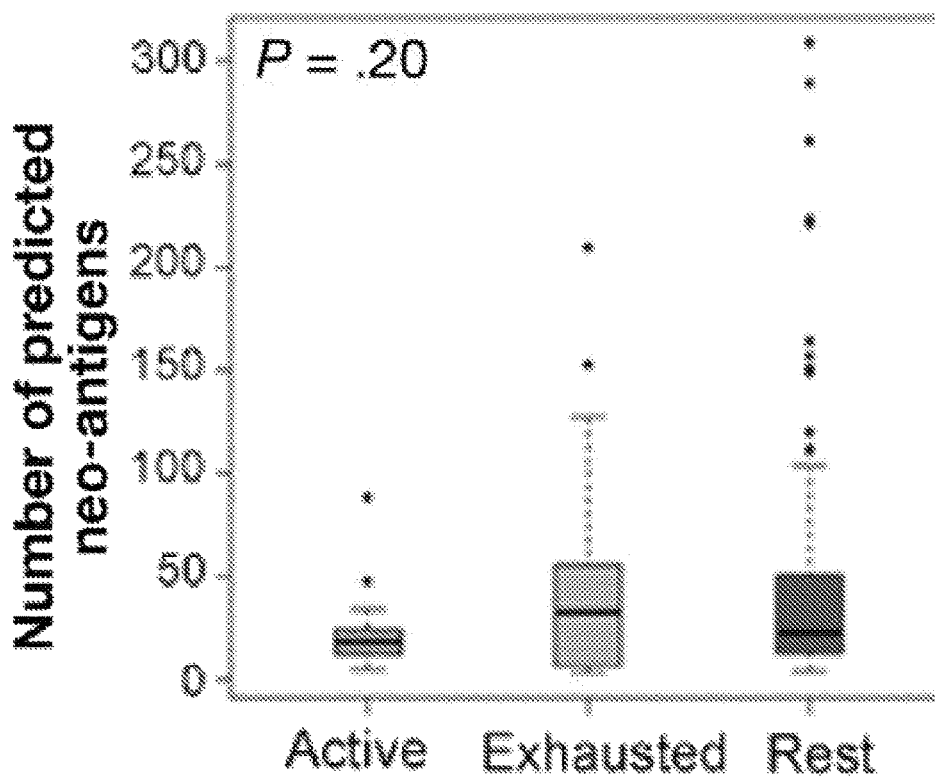
FIG. 6D is a graph showing the rate of mutations predicted to yield a neo-antigen between the two microenvironment-based subtypes and the rest of the cohort.
Figure 6F:
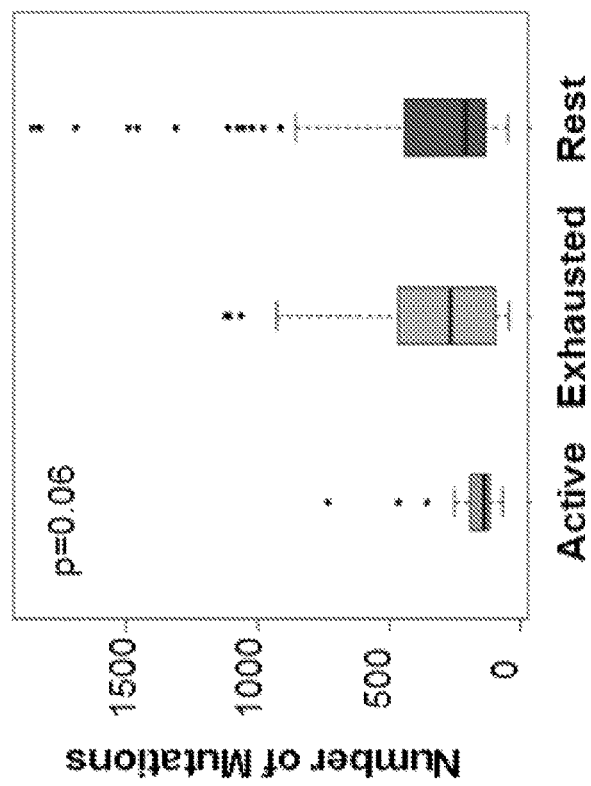
FIG. 6F is a graph of the rate of mutation between the distinct Immune subtypes and the rest of the cohort.
Figure 6E:
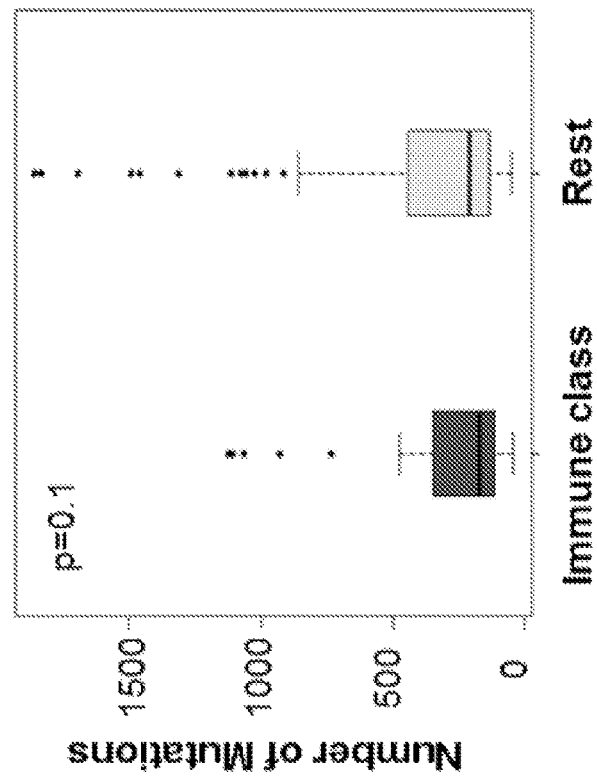
FIG. 6E is a graph of the comparison of the rate of mutations between the Immune class and the rest of the cohort.

Then the Immune class was correlated with the overall rate of mutations and rate of predicted neo-antigens, as per previous analysis of the TCGA dataset (Rooney, et al. 2015). There was no association between the Immune class and both features (FIGS. 6C and 6E). In particular, the median number of mutations for Immune class compared among the remaining patients was 175 vs 212, respectively (p=0.1, FIG. 6E). Similarly, the rate of neo-antigens was not statistically different between the two groups (21 vs 23, respectively, p=0.28, FIG. 6C). Nonetheless, when both parameters were analyzed according to the microenvironment-based subtype, the Active Immune subtype showed a trend towards lower neo-epitopes rate (median of 18 versus 33 in Exhausted versus 23 in rest of cohort, p=0.20, FIG. 6D) and mutations (median of 140 versus 269 in Exhausted subtype versus 212 in rest of cohort, p=0.06, FIG. 6F)).

Figure 6G:
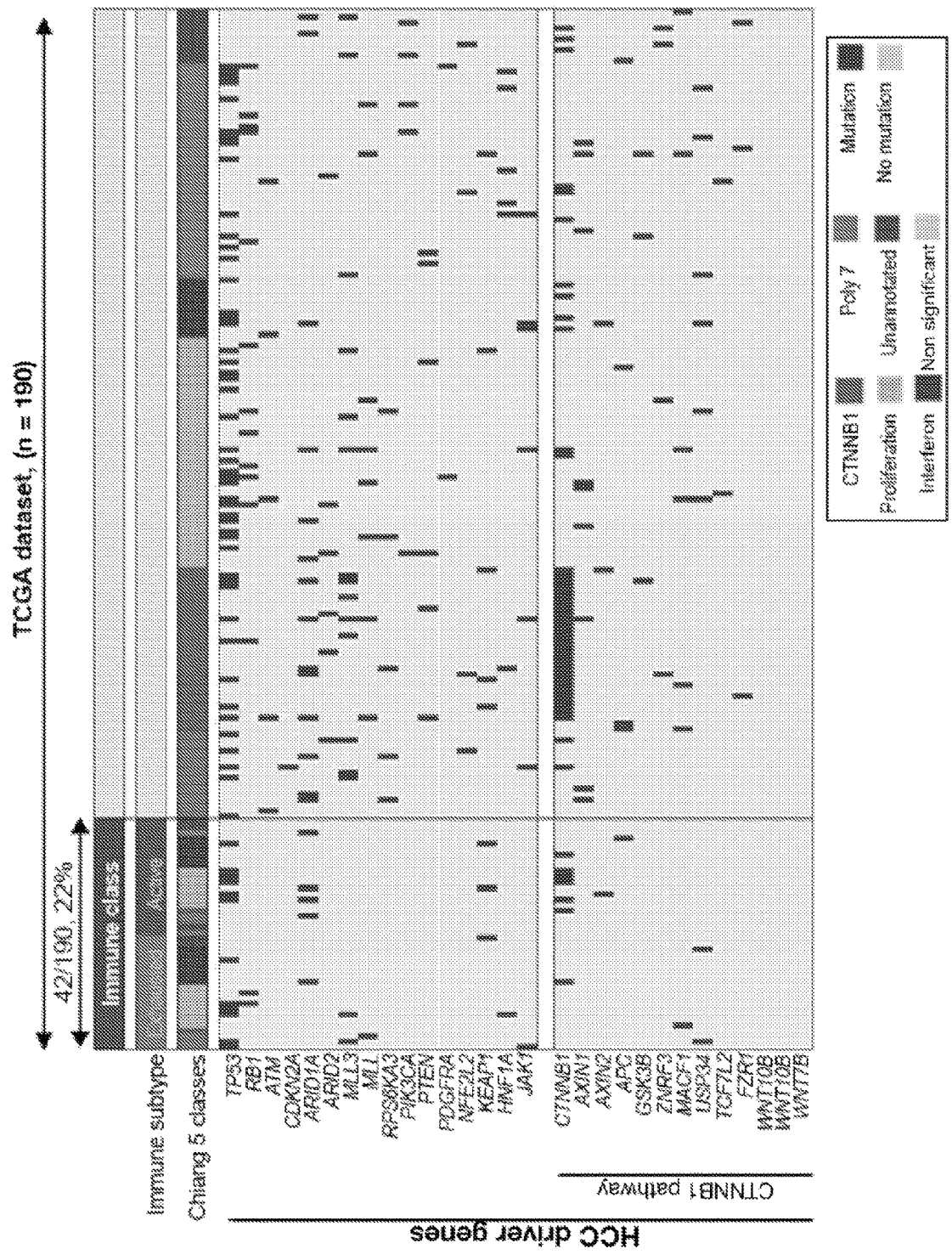
FIG. 6G is a heatmap representation of the distribution of mutations in known driver genes between patients of the Immune class and rest of TGCA cohort.

Finally, the Immune class was correlated with mutations in known driver genes. With the exception of mutations in the CTNNB1 pathway (12/42 vs 81/148, p=0.003), no other mutations showed differential distribution (FIG. 6G).

All these data showed no correlation between neo-antigen load and T cell response, which indicates that additional mechanisms, such as aneuploidy and mutations in specific oncogenic pathways, may impair immune cell recruitment in highly immunogenic tumors.

Example 7—the Immune Class has a Unique DNA Methylation Signature

Figure 6H:
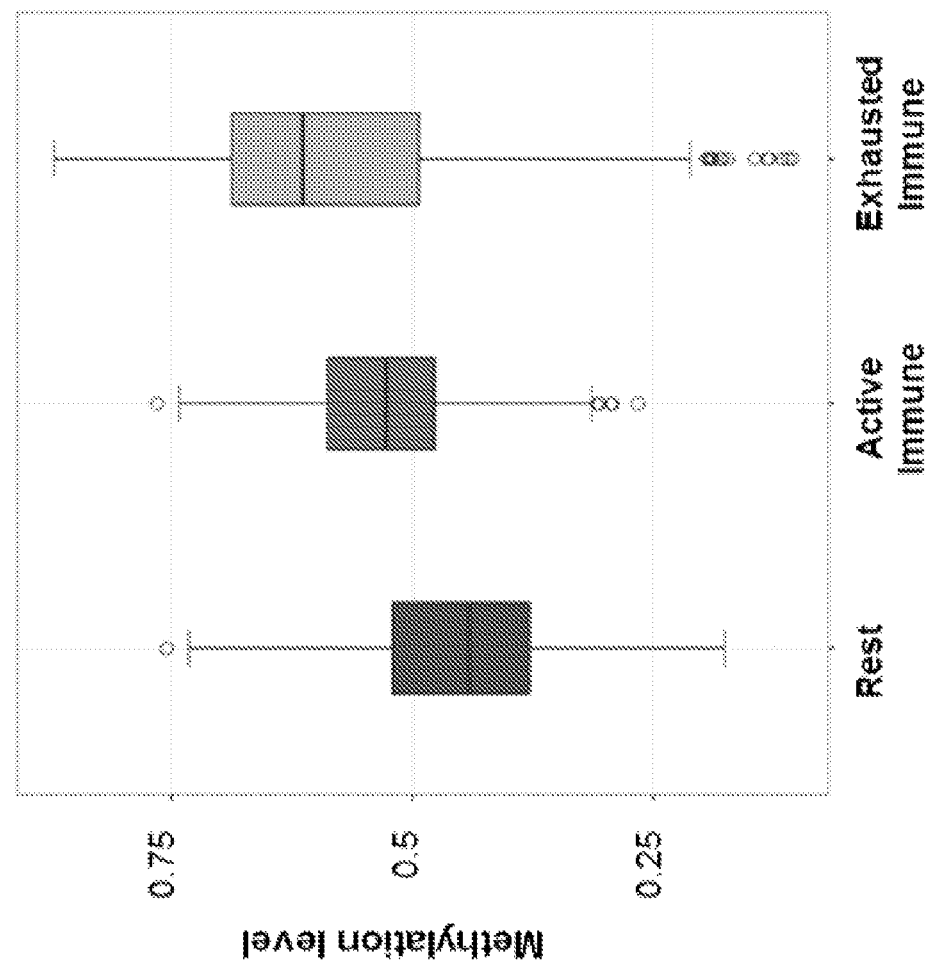
FIG. 6H is a graph of the difference in the methylation levels of 363 CpG sites in 192 immune related promoter genes among 3 groups is represented as box plot. Exact p values according to Tukey test are: between Active vs rest: p=3.57E-13; Exhausted vs rest: p=1.93E-13; Exhausted vs Active: p=3.42E-7.

Considering the profound up-regulation of immune-related genes in the Immune class, it was considered whether such deregulation could mirror epigenetic alterations in these tumors. Supervised analysis of whole genome methylation data revealed that 363 CpG sites in 192 immune response gene promoters were differentially methylated in the Immune class compared to the rest of the cohort (FDR<0.05, FIG. 6H). Furthermore, among the 192 genes showing differentially methylated CpG sites, 115 showed a significant correlation with gene expression.

In particular, the immunosuppressive molecule LGALS3, which may play a role in immune escape during tumor progression through the induction of apoptosis of cancer-infiltrating T cells (Fukimori et al. 2003) and the regulator of the TGF-β signaling, PMEPA1, were significantly over-expressed in the 2 Immune subtypes (p<0.001, FIG. 6I).

Overall, these data indicated that the Immune class was characterized by a unique methylation profile. In particular, differential methylation was observed in 192 immune related genes and, in most instances, was associated with altered gene expression.

Figures 6J, 6K:
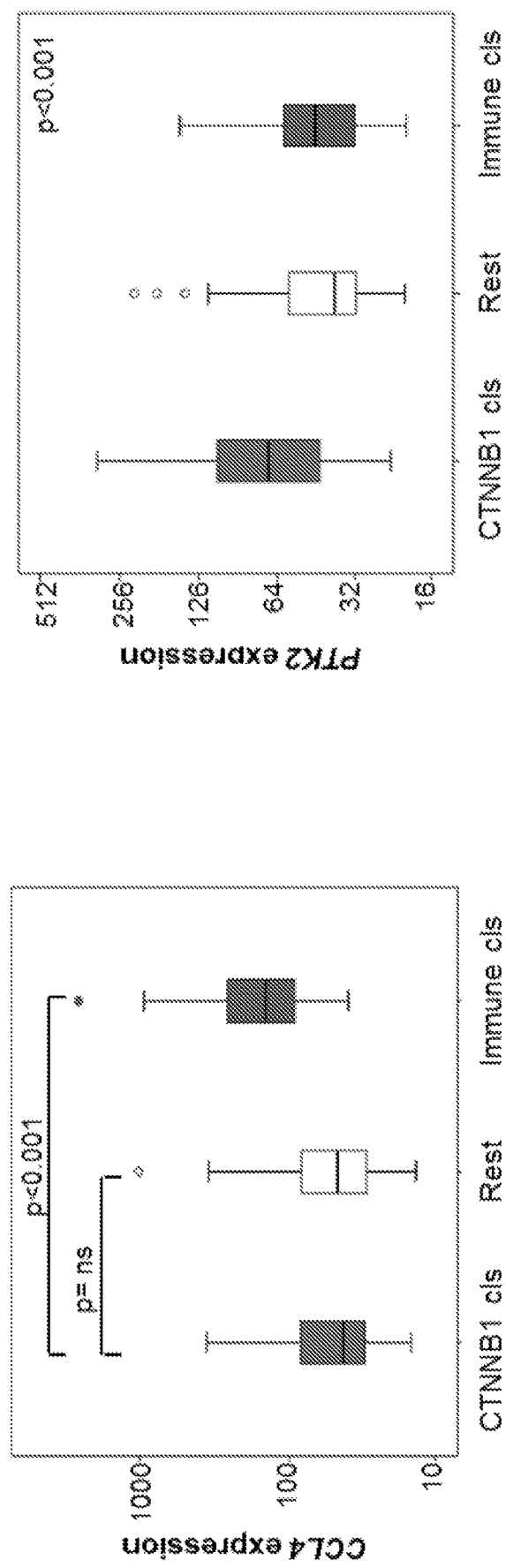
FIG. 6J is a box-plot representation of CCL4 expression in patients of the CTNNB1 class compared to Immune class and rest of cohort.
FIG. 6K is a box-plot representation of normalized PTK2 expression (microarray data) in patients of the CTNNB1 class compared to patients of the Immune class and rest of the cohort. PTK2 expression is expressed in log 2.
Figure 6M:
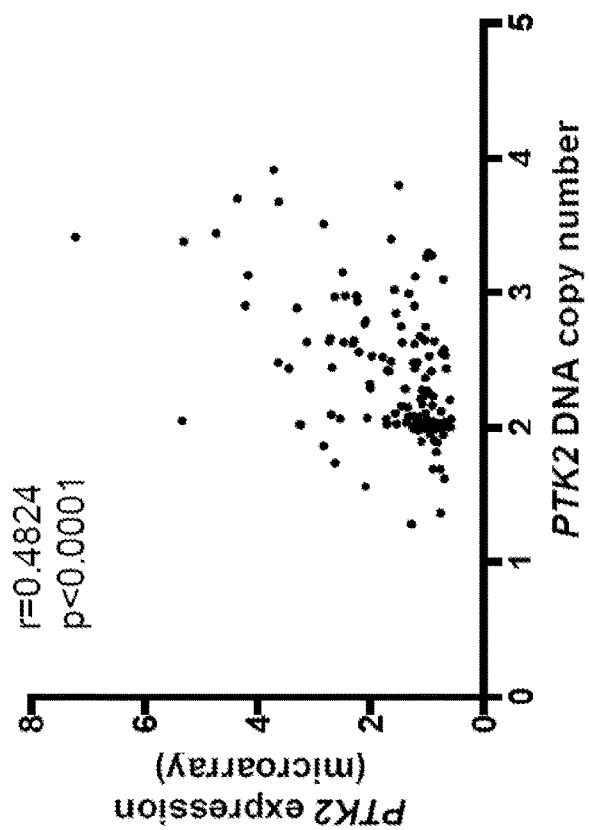
FIG. 6M is a graph of the correlation of normalized gene expression levels detected by microarray and copy number in HCC samples of the Heptromic cohort (Spearman's rank correlation coefficient).
Figure 6L:
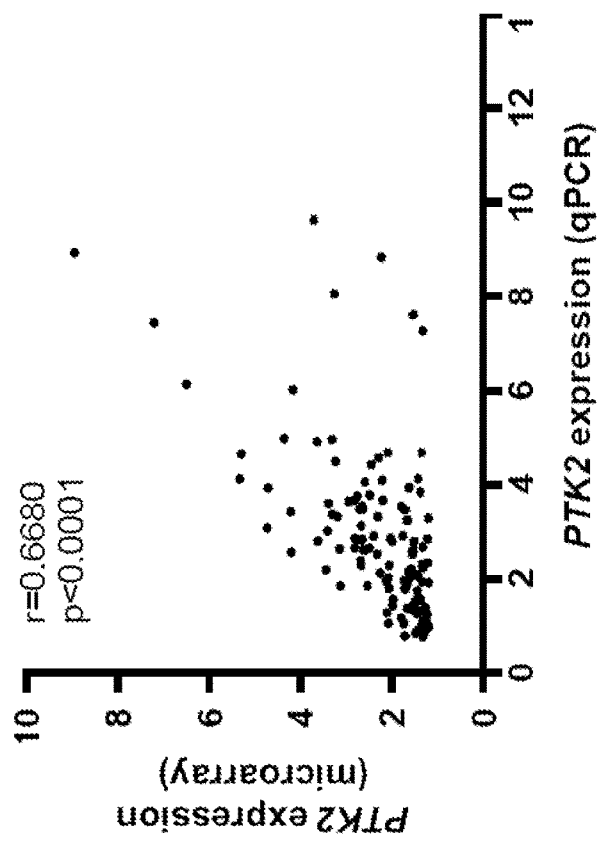
FIG. 6L shows a graph of the correlation of normalized PTK2 gene expression levels detected by microarray and qRT-PCR in HCC samples of the Heptromic cohort.

Example 8—Specific Oncogenic Signaling Pathways could Cooperate to Reduce T Cell Infiltration in the CTNNB1 Class of HCC The integration of the Immune class with previously reported molecular classifications revealed a significant exclusion of the CTNNB1 class in all datasets tested (FIGS. 3A and 5C). The CTNNB1 class of HCC was characterized by over-expression of liver-related Wnt-target-genes, enrichment in nuclear β-catenin staining and CTNNB1-mutations (Chiang, et al. 2008). Exclusion of the CTNNB1 class supports recent reports in melanoma where activation of the pathway is associated with T cell exclusion, through the repression of CCL4 and subsequent failure of T cell priming (Spranger, et al. 2015). In the cohorts, HCC samples within the CTNNB1 class showed significantly lower enrichment score for several immune signatures, in particular T cells, compared to patients within the Immune class or the remaining patients (p<0.001, FIGS. 6J and 6K). In addition, in accordance with data in melanoma, patients within the CTNNB1 class showed down-regulation of CCL4 (p<0.001). Further oncogenic pathways have been associated with T cell exclusion, including PTEN (Peng, et al. 2016) and PTK2 (Jiang et al. 2016). Interestingly, PTK2 was significantly over-expressed in the CTNNB1 class, suggesting a possible cooperation between PTK2 and CTNNB1 pathways to induce immune cells exclusion in this subgroup. In addition, DNA copy number and expression of PTK2 were highly correlated (p<0.0001) (FIGS. 6L and 6M).

These data suggest that HCC samples within the CTNNB1 class showed lower expression of immune signatures compared to patients of the Immune class and the remaining tumors. Activation of specific oncogenic signaling, such as CTNNB1 and PTK2 signaling—through activating mutations or additional mechanisms—may play a seminal role in influencing the immunological profile of this subgroup.

Figures 7, 7A:
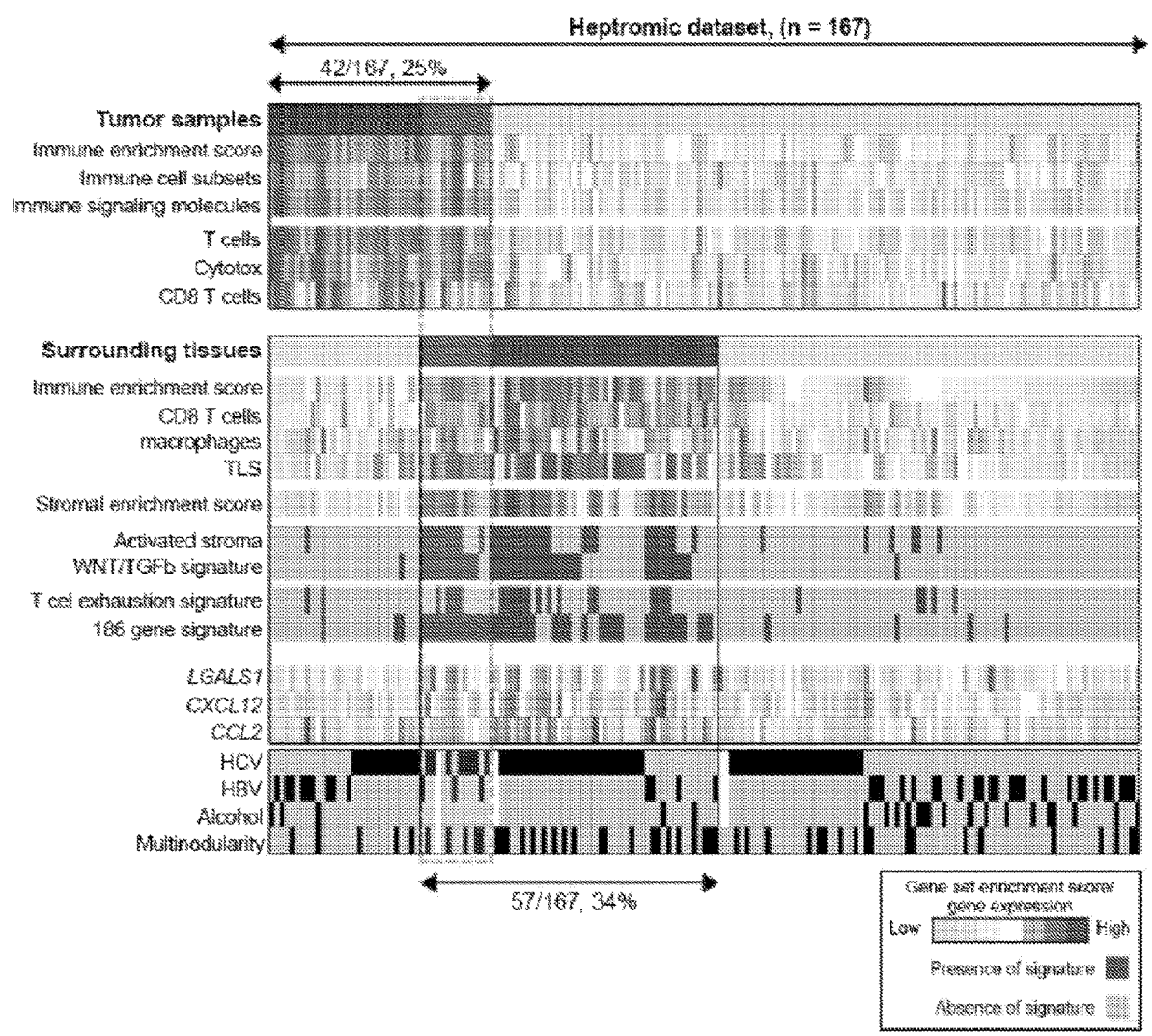
FIG. 7 shows the intratumoral immune profile does not correspond to the immune infiltration of the surrounding non-tumoral liver.
FIG. 7A shows gene expression of the tumor (upper panel) and matched surrounding non-tumoral liver (lower panel) was available for 167 patients of the Heptromic cohort (training dataset). Heatmap represents enrichment scores for immune signatures in the tumors (upper panel) and corresponding surrounding tissues (bottom panel). Multi-nodularity was more frequent in patients which are positive for the immune classifier [25/55 (45%) vs24/110 (22%), p=0.01].
Figure 7B:
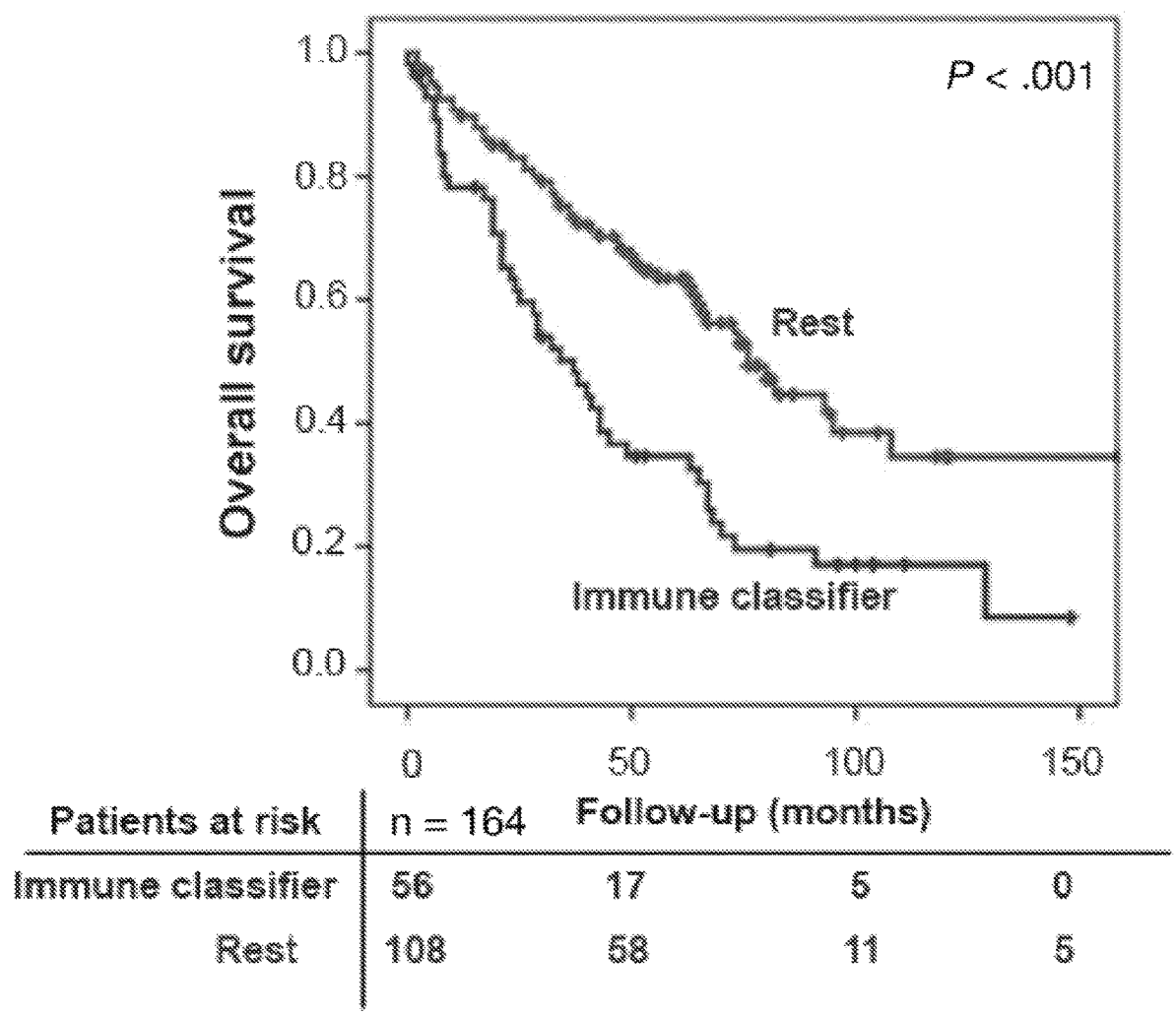
FIG. 7B shows Kaplan-Meyer estimates of overall survival according to the presence of the Immune Classifier in the surrounding liver.

Example 9—Compartmentalization of Immune Signals: Immune Infiltration in the Surrounding Tissue does not Reflect its Tumor Counterpart Finally, in order to assess whether the type of intra-tumoral immune cell infiltrates mirrors its peritumoral counterpart, the intra-tumoral immune infiltration correlated with the surrounding liver tissue. To do so, a sub-analysis in 167 patients of the training cohort was performed for whom gene expression data were available for both tumor and matched surrounding nontumoral tissue. Among the 167 cases, 25% (42/167) were positively classified within the Immune class based on the expression profile of the tumor (FIG. 7A). Interestingly, only a minority of these patients (13/42, 31%) showed a combined positive prediction in both tumor and matched surrounding liver, suggesting that the intra-tumoral immune infiltration does not reflect the profile of the surrounding tissue. Given these observations, it was further explored the type of immune infiltration occurring in the non-tumoral liver. Interestingly, patients positively predicted by the Immune Classifier based on the profile of the surrounding tissue showed a strong enrichment of signatures capturing the presence of immune cells (CD8, macrophages, p<0.001), activated stroma [31/57 (54%) vs 7/110, (6%), p=0.0001], TGF-β signaling [38/57, (67%) vs 2/110, (2%), p=p=0.0001] and additional immunosuppressive components (LGALS1, CXCL12, p<0.001). In addition, exhausted T cells [19/57, (33%) vs 7/110 (6%), p=0.0001], and a prognostic 186-gene signature derived from the surrounding liver [43/57 (75%) vs 7/110 (6%), p=0.0001] were also enriched in this subgroup. In addition, it was observed that METAVIRF3-F4 stages [42/45 (93%) vs 66/87 (76%) in rest of cohort, p=0.02] and HCV infection [36/54 (67%) vs 39/108 (36%) in rest, p<0.001] were significantly associated to a positive Immune Classifier in the surrounding liver. On the other end, HBV infection [7/54 (13%) vs 34/108 (31%), p=0.01] and alcohol abuse [2/54 (4%) vs 20/108 (19%), p=0.008] were more frequent in patients negative for the immune classifier (FIG. 7A). Finally, patients which are positive for the Immune Classifier showed significant worse prognosis with a median survival time of 37 vs 76 months in the rest of the cohort (p<0.001, FIG. 7B).

In essence, these data suggested that the immune profile of the surrounding liver tumor does not reflect the intratumoral profile and is mostly characterized by immunosuppressive components associated with survival of HCC patients.

Example 10—Identification of a 56-Gene Classifier of the Immune Class

The original 112-genes Immune classifier (FIG. 10A-D) has been successfully reduced to 56 genes selecting those genes with highest score (Table 3). The prediction capacity of the 56-genes Immune classifier has been tested and compared to the 112-genes original immune classifier in 3 datasets: TGCA (n=190 samples, FIG. 14A), Validation cohort (n=132, FIG. 14B) and HCC-I dataset (n=90, FIG. 14C).

As indicated below, the 56-genes Immune classifier had a sensitivity of 97% (range 95-100% when analyzed in the 3 cohorts separately), specificity of 98% (range 96-99% when analyzed in the 3 cohorts separately) and an accuracy of 97% (range 96-98% when analyzed in the 3 cohorts separately), (Table 2).

In addition the Receiver Operating Characteristic (ROC) curve was calculated for the 56-genes Immune classifier in all patients from the 3 cohorts (n=411, FIG. 15). ROC curves are a useful way to interpret sensitivity and specificity levels. ROC curves are a generalization of the set of potential combinations of sensitivity and specificity possible for predictors and provide a natural common scale for comparing different predictors, in this case the original 112-genes Immune classifier and the reduced 56-genes Immune classifier. AUC values closer to 1 indicate that screening measure reliably distinguishes among patients with satisfactory performance. In the case of the 56-genes Immune classifier, when tested in all patients the area under the curve was 0.971 (FIG. 15).

TABLE 2:

Sensitivity, specificity, positive predictive value, negative predictive value and accuracy of the 56-genes Immune classifier

|  | Value | 95% CI |
|---|---|---|
| Statistic in all 3 cohorts | | |
| Sensitivity | 97% | 91.41% to 99.05% |
| Specificity | 98% | 95.20% to 99.05% |
| Positive Predictive Value | 94% | 88.49% to 97.08% |
| Negative Predictive Value | 99% | 96.51% to 99.48% |
| Accuracy | 97% | 95.28% to 98.66 |
| Statistic, TCGA cohort (n = 190) | | |
| Sensitivity | 95% | 83.84% to 99.42% |
| Specificity | 99% | 95.20% to 99.84% |
| Positive Predictive Value | 95% | 83.45% to 98.76% |
| Negative Predictive Value | 99% | 94.97% to 99.65% |
| Accuracy | 98% | 94.70% to 99.42% |
| Statistic, Validation cohort (n = 132) | | |
| Sensitivity | 100% | 92.60% to 100.00% |
| Specificity | 96% | 89.80% to 99.25% |
| Positive Predictive Value | 94% | 84.05% to 97.98% |
| Negative Predictive Value | 100% | |
| Accuracy | 98% | 93.45% to 99.53% |
| Statistic, HCC-I cohort (n = 90) | | |
| Sensitivity | 92% | 73.00% to 98.97% |
| Specificity | 97% | 89.48% to 99.63% |

TABLE 2:-continued

Sensitivity, specificity, positive predictive value, negative predictive value and accuracy of the 56-genes Immune classifier

|  | Value | 95% CI |
|---|---|---|
| Positive Predictive Value | 92% | 73.65% to 97.74% |
| Negative Predictive Value | 97% | 89.46% to 99.18% |
| Accuracy | 96% | 89.01% to 98.78% |

TABLE 3

56-genes Immune classifier

| Gene ID | Class |
|---|---|
| LCP2 | Immune class |
| PTPRC | Immune class |
| CCL5 | Immune class |
| LAPTM5 | Immune class |
| GZMA | Immune class |
| SLA | Immune class |
| FYB | Immune class |
| CD53 | Immune class |
| CD3D | Immune class |
| GZMK | Immune class |
| CD48 | Immune class |
| CD2 | Immune class |
| CD52 | Immune class |
| S100A4 | Immune class |
| ITGB2 | Immune class |
| RAC2 | Immune class |
| CORO1A | Immune class |
| IL7R | Immune class |
| CYTIP | Immune class |
| SRGN | Immune class |
| SAMSN1 | Immune class |
| FAM26F | Immune class |
| GPR171 | Immune class |
| CD27 | Immune class |
| MTHFD2 | Immune class |
| CXCR4 | Immune class |
| TIMP1 | Immune class |
| C16orf54 | Immune class |
| CD8A | Immune class |
| LUM | Immune class |
| DUSP2 | Immune class |
| POU2AF1 | Immune class |
| EFEMP1 | Immune class |
| CXCL9 | Immune class |
| PMP22 | Immune class |
| IGHM | Immune class |
| LXN | Immune class |
| DCN | Immune class |
| RGS1 | Immune class |
| THBS2 | Immune class |
| PTGIS | Immune class |
| SMOC2 | Immune class |
| MMP9 | Immune class |
| GZMH | Immune class |
| AEBP1 | Immune class |
| COL6A3 | Immune class |
| GEM | Immune class |
| CTGF | Immune class |
| CCL19 | Immune class |
| MGP | Immune class |
| PAGE4 | Rest |
| UGT2B17 | Rest |
| C1QTNF3 | Rest |
| DHRS2 | Rest |
| FAM133A | Rest |
| ASCL1 | Rest |

REFERENCES

Alistar, et al. (2014) *Genome Med* 6:80.
Bald, et al. (2014) *Cancer Discov* 4:674-87.

Balli, et al. (2016) *Clin Cancer Res* 23(12):3129-38.
Bindea, et al. (2013) *Immunity* 39:782-95.
Borghaei, et al. (2015 *N Engl J Med* 373:1627-39.
Boyault, et al. (2007) *Hepatology* 45:42-52.
Brunnstrom et al. (2017) *Modern Pathology* 30(10):1411-21.
Breiman (2001) *Machine Learning,* 45(1):5-32.
Brunet, et al. (2004) *Proc Natl Acad Sci USA* 101:4164-9.
Calderaro, et al. (2016) *Hepatology* 64:2038-2046.
Calon, et al. (2012) *Cancer Cell* 22:571-84.
Cancer Genome Atlas N. Genomic Classification of Cutaneous Melanoma. (2015) *Cell* 161:1681-96.
Charoentong, et al. (2017) *Cell Rep* 18:248-262.
Chen, et al. (2016) *Cancer Discov* 6:827-37.
Chen, et al. (2002) *Mol Biol Cell* 13:1929-39.
Chiang, et al. (2008) *Cancer Res* 68:6779-88.
Chow, et al. (2016) *J Clin Oncol* 34, (suppl; abstr 6010).
Coates, et al. (2008) *Cancer Res* 68:450-6.
Coulouar, et al. (2008) *Hepatology* 47:2059-67.
Davoli, et al. (2017) *Science* 355(6322).
Deng et al. (2014) *J. Clin. Invest.* 124(2):687-695
El-Khoueiry, et al. (2017) *Lancet* 389:2492-2502.
Finkin, et al. (2015) *Nat Immunol* 16:1235-44.
Flavell, et al. (2010) *Nat Rev Immunol* 10:554-67.
Fukumori, et al. (2003) *Cancer Res* 63:8302-11.
Garon, et al. (2015) *N Engl J Med* 372:2018-28.
Hanahan and Weinberg (2011) *Cell* 144:646-74.
Herbst, et al. (2016) *Lancet* 387:1540-50.
Hoshida, et al. (2009) *Cancer Res* 69:7385-92.
Hoshida, et al. (2008) *N Engl J Med* 359:1995-2004.
Hoshida, et al. (2007) *PLoS One* 2:e1195.
Hoshida, et al. (2013) *Gastroenterology* 144(5):1024-30.
Iizuka, et al. (2003) *Lancet* 361:923-9.
Ji, et al. (2012) *Cancer Immunol Immunother* 61:1019-31.
Jiang, et al. (2016) *Nat Med* 22:851-60.
Khalil, et al. (2016) *Nat Rev Clin Oncol* 13:394.
Lachenmayer, et al. (2012) *Clin Cancer Res* 18:4997-5007.
Le, et al. (2015) *N Engl J Med* 372:2509-20.
Lee, et al. (2004) *Nat Genet* 36:1306-11.
Llovet, et al. (2008) *N Engl J Med* 359:378-90.
Llovet, et al. (2015) *Nat Rev Clin Oncol* 12:408-24.
Llovet, et al. (2016) *Nat Rev Dis Primers* 2:16018.
McGranahan, et al. (2016) *Science* 351:1463-9.
Mermel, et al. (2011) *Genome Biol* 12:R41.
Messina, et al. (2012) *Sci Rep* 2:765.
Moffitt, et al. (2015) *Nat Genet* 47:1168-78.
Murray, et al. (2012) *Lancet* 380:2197-223.
Nielsen, et al. (2007) *PLoS One* 2:e796.
Park, et al. (2016) *Cancer Discov* 6:1366-81.
Peng, et al. (2016) *Cancer Discov* 6:202-16.
Porta-Pardo and Godzik (2016) *Cancer Immunol Res* 4:789-98.
Powles, et al. (2014) *Nature* 515:558-62.
Quigley, et al. (2010) *Nat Med* 16:1147-51.
Rajasagi, et al. (2014) *Blood* 124:453-62.
Reich, et al. (2006) *Nat Genet* 38:500-1.
Ribas, et al. (2015) *J Clin Oncol* 33, (suppl; abstr 3001).
Robert, et al. (2015) *N Engl J Med* 372:2521-32.
Roh, et al. (2017) *Sci Transl Med* 9.
Rooney, et al. (2015) *Cell* 60:48-61.
Schulze, et al. (2015) *Nat Genet* 47:505-11.
Slavuljica, et al. (2011) *Front Immunol* 2:85.
Spranger, et al. (2015) *Nature* 523:231-5.
Stephen, et al. (2014) *Immunity* 41:427-39.
Topalian, et al. (2012) *N Engl J Med* 366:2443-54.
Viel, et al. (2016) *Sci Signal* 9:ra19.
Villanueva, et al. (2015) *Hepatology* 61:1945-56.
Villanueva, et al. (2011) *Gastroenterology* 140:1501-12 e2.
Wang et al. 2016 *OncoTargets and Therapy* 9:5023-39
Weir, et al. (2007) *Nature* 450:893-8.
Yoshihara, et al. (2013) *Nat Commun* 4:2612.
Zou et al. (2016) *Sci Transl. Med* 8:328rv4.
Zucman-Rossi, et al. (2015) *Gastroenterology* 149:1226-1239 e4.

The invention claimed is:

1. A method of treating a subject with hepatocellular carcinoma, comprising
 a. assaying gene expression levels of LCP2, PRPTC, CCL5, LAPTM5, GZMA, SLA, FYB, CD53, CD3D, GZMK, CD48, CD2, CD52, S100A4, ITGB2, RAC2, CORO1A, IL7R, CYTIP, SRGN, SAMSN1, FAM26F, GRP171, CD27, MTHFD2, CXCR4, TIMP1, C16orf54, CD8A, LUM, DUSP2, POU2AF1, EFEMP1, CXCL9, PMP22, IGHM, LXX, DCN, RGS1, THBS2, PTGIS, SMOC2, MMP9, GZMH, AEBP1, COL6A3, GEM, CTGF, CCL19, MGP, PAGE4, UGT2B17, C1QTNF3, DHRS2, FAM133A, and ASCL1 in a sample from the subject with hepatocellular carcinoma to obtain a test expression profile;
 b. comparing the test expression profile of the genes with a reference expression profile, wherein the reference expression profile comprises a reference expression level of the same genes in a sample from a control and is indicative of immunotherapy responsive phenotype;
 c. detecting the gene expression levels of one or more genes in the test expression profile are the same as compared to expression level of the same genes in the reference expression profile that is indicative of immunotherapy responsive phenotype and further detecting that the subject would be responsive to immunotherapy; and
 d. treating the subject with immunotherapy.

2. The method of claim 1, wherein the subject has recently been diagnosed with hepatocellular carcinoma (HCC).

3. The method of claim 1, wherein the sample from the subject with hepatocellular carcinoma is from a hepatocellular carcinoma tumor.

4. The method of claim 1, wherein the control is selected from the group consisting of a subject with hepatocellular carcinoma who has responded favorably to immunotherapy and a subject with another form of cancer who has responded favorably to immunotherapy.

5. The method of claim 4, wherein the cancer is lung cancer or melanoma.

6. The method of claim 1, wherein the immunotherapy is selected from the group consisting of monoclonal antibodies directed against the cytotoxic T-lymphocyte protein (CTLA-4), the programmed cell death protein 1 (PD-1) and its ligand PD-L1, and combinations thereof.

7. A method of treating a subject with hepatocellular carcinoma, comprising
 a. assaying gene expression levels of LCP2, PRPTC, CCL5, LAPTM5, GZMA, SLA, FYB, CD53, CD3D, GZMK, CD48, CD2, CD52, S100A4, ITGB2, RAC2, CORO1A, IL7R, CYTIP, SRGN, SAMSN1, FAM26F, GRP171, CD27, MTHFD2, CXCR4, TIMP1, C16orf54, CD8A, LUM, DUSP2, POU2AF1, EFEMP1, CXCL9, PMP22, IGHM, LXX, DCN, RGS1, THBS2, PTGIS, SMOC2, MMP9, GZMH, AEBP1, COL6A3, GEM, CTGF, CCL19, MGP, PAGE4, UGT2B17, C1QTNF3, DHRS2, FAM133A, and ASCL1 in a sample from the subject with hepatocellular carcinoma to obtain a first test expression profile;

b. comparing the first test expression profile of the genes with a first reference expression profile, wherein the first reference expression profile comprises a reference expression level of the same genes, used in the first test expression profile, from a first sample from a first control and is indicative of immunotherapy responsive phenotype;

c. detecting the gene expression levels of one or more genes in the first test expression profile are the same as compared to expression level of the same genes in the first reference expression profile that is indicative of immunotherapy responsive phenotype and further detecting that the subject would be responsive to immunotherapy;

d. assaying the gene expression levels of one or more genes selected from the group consisting of PMEPA1, LGALS1, LGALS3, TGF-β, CCL4, PTK2 and combinations thereof in the sample from the subject with hepatocellular carcinoma to obtain a second test expression profile;

e. comparing the second expression profile of the one or more genes selected from the group consisting of PMEPA1, LGALS1, LGALS3, TGF-β, CCL4, PTK2 and combinations thereof with a second reference expression profile, wherein the second reference expression profile comprises a reference expression level of the same genes, used in the second test expression profile, from a sample from the first or a second control and is indicative of the Exhausted Immune Response class;

f. detecting the gene expression levels of one or more genes in the second test expression profile are the same as compared to expression level of the same genes in the second reference expression profile that is indicative of the Exhausted Immune Response class; and g. treating the subject with immunotherapy.

8. The method of claim 7, wherein the subject has recently been diagnosed with hepatocellular carcinoma (HCC).

9. The method of claim 7, wherein the sample from the subject with hepatocellular carcinoma is from a hepatocellular carcinoma tumor.

10. The method of claim 7, wherein the first control is selected from the group consisting of a subject with hepatocellular carcinoma who has responded favorably to immunotherapy and a subject with another form of cancer who has responded favorably to immunotherapy.

11. The method of claim 10, wherein the cancer is lung cancer or melanoma.

12. The method of claim 7, wherein the immunotherapy is selected from the group consisting of monoclonal antibodies directed against the cytotoxic T-lymphocyte protein (CTLA-4), the programmed cell death protein 1 (PD-1), and its ligand PD-L1, and combinations thereof.

* * * * *